(12) United States Patent
Kwon et al.

(10) Patent No.: US 9,353,144 B2
(45) Date of Patent: May 31, 2016

(54) VASCULAR LEAKAGE INHIBITOR

(71) Applicant: INDUSTRY-ACADEMIC COOPERATION FOUNDATION, YONSEI UNIVERSITY, Seoul (KR)

(72) Inventors: Young-Gune Kwon, Seoul (KR); Young-Ger Suh, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/375,847

(22) PCT Filed: Dec. 28, 2012

(86) PCT No.: PCT/KR2012/011771
§ 371 (c)(1),
(2) Date: Jul. 31, 2014

(87) PCT Pub. No.: WO2013/100712
PCT Pub. Date: Jul. 4, 2013

(65) Prior Publication Data
US 2014/0378399 A1    Dec. 25, 2014

(30) Foreign Application Priority Data
Dec. 29, 2011    (KR) .................. 10-2011-0145988

(51) Int. Cl.
*C07J 17/00*    (2006.01)
*C07J 43/00*    (2006.01)
*A61K 31/56*    (2006.01)
*C07J 41/00*    (2006.01)

(52) U.S. Cl.
CPC .............. *C07J 17/005* (2013.01); *A61K 31/56* (2013.01); *C07J 17/00* (2013.01); *C07J 41/005* (2013.01); *C07J 43/003* (2013.01)

(58) Field of Classification Search
None
See application file for complete search history.

(56) References Cited

U.S. PATENT DOCUMENTS

| 6,133,280 A * | 10/2000 | Brodie ............... C07J 73/00 514/176 |
| 6,218,367 B1 * | 4/2001 | Jacob ............... C07H 15/26 514/25 |
| 2006/0149045 A1 * | 7/2006 | Braekman ........... A61K 31/57 536/6.1 |

FOREIGN PATENT DOCUMENTS

| KR | 10-2005-0117787 A | 12/2005 |
| KR | 10-2006-0100883 A | 9/2006 |
| KR | 10-2007-00032435 A | 3/2007 |
| KR | 10-2011-0047170 A | 5/2011 |

OTHER PUBLICATIONS

Merck Manual, Overview of Stroke, internet article, Nov. 2007.*
Merck Manual, Overview of Inflammatory Bowel Disease, internet article, Aug. 2006.*
Merck Manual, Cancer Treatment Principles, internet article, downloaded from the internet Jun. 7, 2013.*
Merck Manual, Glaucoma, internet article, Aug. 2008.*
Merck Manual, Diabetes Mellitus, internet article, Jun. 2008.*
Lucas, Journal of the American Chemical Society (1960), 82, 5688-93.*
Mičková, Collection Czechoslov. Chem. Commun./vol. 34/(1969).*
Written Opinion of the International Search Authority, Apr. 29, 2013.
International Preliminary Report on Patentability Chapter I, Apr. 29, 2013.
International Search Report, Apr. 29, 2013.

* cited by examiner

*Primary Examiner* — Layla Berry
(74) *Attorney, Agent, or Firm* — Harness, Dickey & Pierce, P.L.C.

(57) ABSTRACT

The present disclosure relates to a novel vascular leakage inhibitor. The novel vascular leakage inhibitor of the present invention inhibits the apoptosis of vascular endothelial cells, inhibits the formation of actin stress fibers induced by VEGF, and enhances the cortical actin ring structure, thereby inhibiting vascular leakage. Accordingly, the vascular leakage inhibitor of the present invention can prevent or treat various diseases caused by vascular leakage. Since the vascular leakage inhibitor of the present invention is synthesized from commercially available or easily synthesizable pregnenolones, it has remarkably superior feasibility of commercial synthesis.

12 Claims, 9 Drawing Sheets

Fig. 4

VASCULAR LEAKAGE INHIBITOR

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/011771, filed 28 Dec. 2012, which claims priority to Korean Patent Application No. 10-2011-0145988, filed 29 Dec. 2011, entire contents of which are incorporated herein by reference.

BACKGROUND OF THE INVENTION

1. Field of the Invention

The present disclosure relates to a novel vascular leakage inhibitor.

2. Description of the Related Art

The disruption of endothelial barrier integrity leading to increased vascular permeability contributes to many pathological processes, including various inflammatory diseases, acute lung injury, and diabetic retinopathy. Endothelial permeability is tightly controlled by cell-cell junctions, including adherens junctions (AJs) and tight junctions (TJs), between neighboring endothelial cells. TJs consist of a number of proteins, including occludin, claudins, junctional adhesion molecules (JAMs), and zonula occludens (ZOs). Occludin, claudins, and JAMs are major integral transmembrane proteins with adhesive properties, and are believed to be responsible for the formation of a tight seal between two opposing endothelial membranes of adjacent cells (*Int J Biochem Cell Biol.* 2004 July; 36(7):1206-37). Occludin and claudins form homodimeric bridges, and ZOs and cingulin connect these integral transmembrane proteins to actin filaments (*J Cell Biol.* 1999 Dec. 27; 147(7):1569-82). Dynamic regulation of perijunctional actin has been suggested to control paracellular permeability by affecting the stability of TJs closely connected to the actin cytoskeleton, either directly or indirectly (*Anna Rev Physiol.* 1998; 60:143-59). In fact, there are ample ultrastructural evidences to implicate the temporal expression, dynamic organization, and spatial distribution of the actin cytoskeleton in the alteration of TJ complexes under various conditions (*Physiol Rev.* 2006 January; 86(1):279-367). Therefore, actin is likely to play a critical role in modulating the integrity of TJs, and thus, endothelial permeability.

The reorganization of the actin cytoskeleton into the cortical actin ring and the concomitant redistribution of TJ proteins to the cell periphery is an inevitable event in endothelial barrier enhancement. Several molecules have been suggested to be important for the formation of the cortical actin ring. Phosphorylated myosin light chain (p-MLC), and its kinase, myosin light chain kinase (MLCK), were observed to be distributed in the cortical region during EC barrier enhancement induced by sphingosine-1-phosphate (S1P), suggesting a potential role for spatially defined MLCK activation in regulating endothelial barrier function. MLC phosphorylation at the cortical region may promote the interaction of actin filaments and myosin, stabilizing the cortical actin ring structures, and thereby increasing the stability of TJ protein complexes in the cell periphery (*J Cell Biochem.* 2004 Aug. 15; 92(6):1075-85). Cortactin, an F-actin binding protein, has also been implicated in cortical actin rearrangement. Cortactin tyrosine phosphorylation and its translocation to the cortical actin have been associated with enhanced endothelial barrier function (*J Biol Chem.* 2004 Jun. 4; 279(23):24692-700). Furthermore, phosphorylated cortactin binds to MLCK via its SH3-domain in the cortical ring, implicating that cort-actin-MLCK interaction at the site of cortical actin polymerization enhances barrier function by localizing the acto-myosin interaction at an optimal location.

Diabetic retinopathy (DR) is one of the most common vascular retinopathies and a leading cause of legal blindness in working-age adults. The earliest sign of DR is leakage from retinal vessels due to breakdown of the blood-retinal barrier (BRB), which is followed by retinal edema and finally endothelial cell proliferation (*N Engl J Med.* 2004 Jan. 1; 350(1): 48-58). The BRB is a selective endothelial barrier of well-differentiated microvessels of the eye. The disruption of the BRB occurs during the earliest period of vascular retinopathy, which can be recovered before the irreversible angiogenesis characteristic of proliferative vascular retinopathy (*Nature.* 2005 Dec. 15; 438(7070):960-6). VEGF is known to play an important role in BRB breakdown by altering tight junction integrity and the cytoskeleton organization of endothelial cells, leading to increased permeability during the pathogenesis of DR (*Ophthalmic Res.* 1995; 27(1):48-52; *Nature.* 2005 Sep. 22; 437(7058):497-504). Therapies targeting this early and reversible stage of BRB breakdown remain to be developed.

Throughout this application, various publications and patents are referred and citations are provided in parentheses. The disclosures of these publications and patents in their entities are hereby incorporated by references into this application in order to fully describe the present disclosure and the state of the art to which this disclosure pertains.

SUMMARY

The inventors of the present disclosure have studied and made efforts to develop substances capable of preventing or treating diseases caused by vascular leakage owing to damaged vascular integrity. As a result, they have synthesized substances having a molecular skeleton similar to that of a ginsenoside Rk1, and identified that these substances can prevent or treat diseases associated with vascular leakage by inhibiting apoptosis of vascular endothelial cells, inhibiting formation of actin stress fibers induced by VEGF, and enhancing the cortical actin ring structure.

The present disclosure is directed to providing a novel ginsenoside Rk1 analog.

The present disclosure is also directed to providing a pharmaceutical composition for preventing or treating diseases associated with vascular leakage.

The present disclosure is also directed to providing a food composition for preventing or treating diseases associated with vascular leakage.

The present disclosure is also directed to providing a method for preventing or treating diseases associated with vascular leakage.

Other features and aspects will be apparent from the following detailed description, drawings and claims.

BRIEF DESCRIPTION OF THE DRAWINGS

FIGS. 2a-2c shows the result of observing cell morphologies. Con is indicative of cells treated with DMSO.

FIGS. 4 and 5 show that the Rk1 analogs Sac-1009, Sac-1104 and Sac-1019 inhibit the formation of actin stress fibers induced by VEGF. Confluent HRECs were pretreated with the compounds (10 μg/mL) for 60 minutes before treating with 20 ng/mL VEGF. The cells were then stained with rhodamine phalloidin.

DETAILED DESCRIPTION OF THIS INVENTION

Figure 1A:
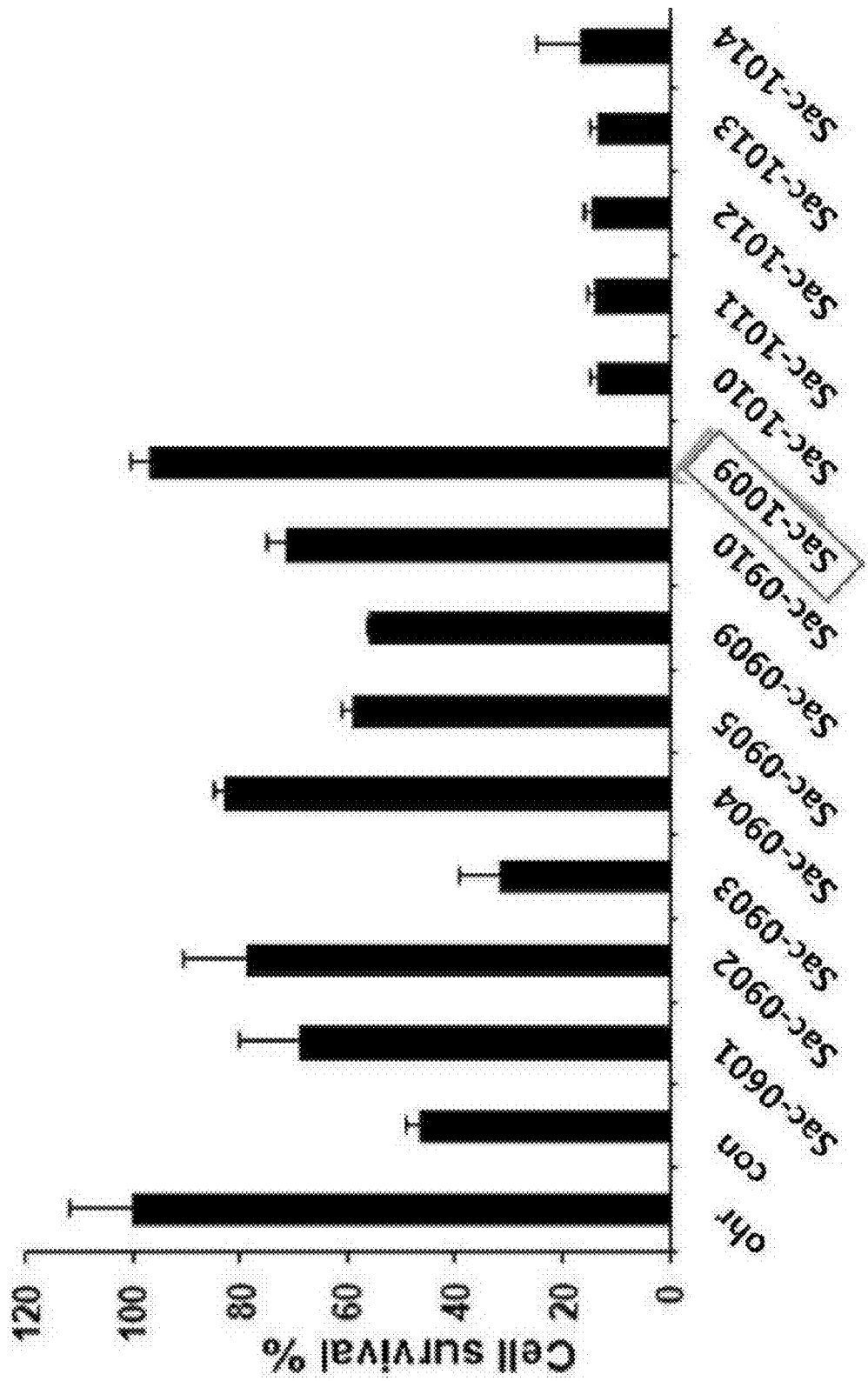
FIGS. 1a-1c and FIGS. 2a-2c show the result of screening Rk1 analogs that protect HRECs (Human Retinal Endothelial Cells) from serum depletion-induced apoptosis. HRECs ($3 \times 10^5$ cells/well) were seeded on a 24-well plate in EGM9 medium containing 20% fetal bovine serum. The next day, the cells were transferred to a medium containing 10 µg/mL of the synthesized compound. Cell viability was determined by MTT assay 48 hours later.

In one general aspect, the present disclosure provides a compound represented by Chemical Formula 1 as a ginsenoside Rk1 analog or a pharmaceutically acceptable salt thereof:

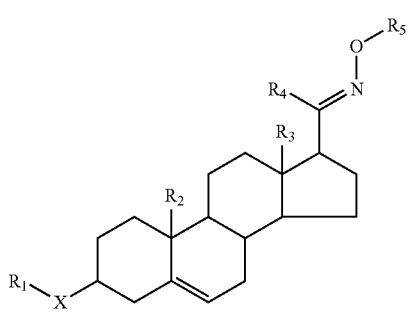

Chemical Formula 1 wherein X is oxygen or sulfur; $R_1$ is hydrogen, halo, $C_{3-10}$ cycloalkyl, $C_{3-10}$ cycloalkenyl, $C_{2-10}$ heterocycloalkyl containing oxygen, sulfur or nitrogen as a heteroatom, $C_{3-15}$ heterocycloalkylalkyl containing oxygen, sulfur or nitrogen as a heteroatom, $C_{3-10}$ heterocycloalkenyl containing oxygen, sulfur or nitrogen as a heteroatom, $C_{6-10}$ aryl, $C_{6-15}$ aralkyl, $C_{6-15}$ alkaryl or $C_{3-15}$ heteroaryl containing oxygen, sulfur or nitrogen as a heteroatom; $R_2$ and $R_3$ are independently hydrogen or $C_{1-10}$ alkyl; $R_4$ is hydrogen, hydroxy or $C_{1-10}$ alkyl; $R_5$ is hydrogen, hydroxyl, $C_{1-30}$ alkyl, $C_{3-10}$ cycloalkyl, $C_{2-30}$ alkenyl, $C_{3-10}$ cycloalkenyl, $C_{2-30}$ alkynyl, $C_{2-10}$ heterocycloalkyl containing oxygen, sulfur or nitrogen as a heteroatom, $C_{3-15}$ heterocycloalkylalkyl containing oxygen, sulfur or nitrogen as a heteroatom, $C_{2-30}$ alkoxyalkyl, $C_{3-30}$ alkoxyalkoxyalkyl, $C_{3-10}$ heterocycloalkenyl containing oxygen, sulfur or nitrogen as a heteroatom, $C_{1-20}$ alcohol, $C_{1-20}$ alkenol, $C_{2-30}$ acyl, $C_{1-10}$ amide, $C_{1-10}$ amine, $C_{2-15}$ ester, sulfate, carboxyl, $C_{3-20}$ carboxyalkyl, $C_{3-20}$ carboxyalkenyl, $C_{3-20}$ alkylcarboxyl, $C_{3-20}$ alkenylcarboxyl, $C_{3-20}$ alkylcarboxyalkyl, $C_{3-20}$ alkylcarboxyalkenyl, $C_{3-20}$ alkenylcarboxyalkyl, $C_{4-20}$ alkenylcarboxyalkenyl, $C_{6-30}$ aryl, $C_{6-30}$ aralkyl, $C_{6-30}$ alkaryl, $C_{3-30}$ heteroaryl containing oxygen, sulfur or nitrogen as a heteroatom or $C_{6-30}$ arylcarbonyl.

In one embodiment of the present disclosure, the ginsenoside Rk1 analog of the present invention is a compound represented by Chemical Formula 2 or a pharmaceutically acceptable salt thereof.

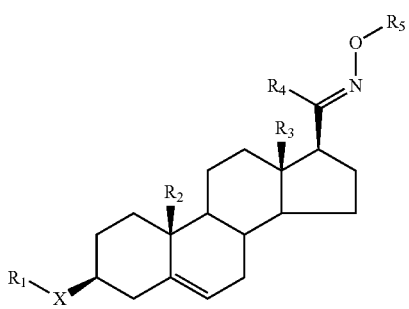

Chemical Formula 2 wherein X, $R_1$, $R_2$, $R_3$, $R_4$ and $R_5$ are the same as defined in Chemical Formula 1.

In another general aspect, the present disclosure provides a pharmaceutical composition for preventing or treating diseases associated with vascular leakage comprising: (a) a pharmaceutically effective amount of the ginsenoside Rk1 analog; and (b) a pharmaceutically acceptable carrier.

In another general aspect, the present disclosure provides a food composition for preventing or treating diseases associated with vascular leakage comprising the ginsenoside Rk1 analog as an active ingredient.

In another general aspect, the present disclosure provides a method for preventing or treating diseases associated with vascular leakage comprising administering the pharmaceutical composition to a subject in need thereof.

The inventors of the present disclosure have studied and made efforts to develop substances capable of preventing or treating diseases caused by vascular leakage owing to damaged vascular integrity. As a result, they have synthesized substances having a molecular skeleton similar to that of a ginsenoside Rk1, and identified that these substances can prevent or treat diseases associated with vascular leakage by inhibiting apoptosis of vascular endothelial cells, inhibiting formation of actin stress fibers induced by VEGF, and enhancing the cortical actin ring structure.

The compound of the present disclosure represented by Chemical Formula 1 is chemically synthesized by mimicking the structure of ginsenosides Rk1, which have already been demonstrated to prevent vascular endothelial cell damage by the inventors of the present disclosure. Since ginsenoside Rk1 is extracted and isolated from expensive ginseng, it is not easily available. Thus, the inventors have made efforts to solve this problem and develop substances exhibiting improved physiological activity and pharmacological profile over ginsenoside Rk1, As a result, they have designed and synthesized the compound of the present disclosure.

The inventors have selected cholesterol, which has a molecular skeleton similar to that of ginsenoside Rk1, is easily commercially available and allows good synthetic approach, as a parent molecule and designed and synthesized various derivatives therefrom.

As used herein, the term "halo" refers to a halogen element and includes, for example, fluoro, chloro, bromo and iodo.

The term "alkyl" refers to a linear or branched, unsubstituted or substituted, saturated hydrocarbon group and includes, for example, methyl, ethyl, propyl, isobutyl, pentyl, hexyl, heptyl, octyl, nonyl, decyl, undecyl, tridecyl, pentadecyl, heptadecyl, etc, $C_{1-3}$ alkyl means an alkyl group having an alkyl unit of 1 to 30 carbons, excluding the number of carbons of a substituent when the $C_{1-30}$ alkyl is substituted, According to one embodiment, in Chemical Formula 1, the $C_{1-10}$ alkyl at $R_2$, $R_3$ and $R_4$ may be specifically $C_{1-5}$ alkyl. According to one embodiment, in Chemical Formula 1, the $C_{1-30}$ alkyl at $R_5$ may be specifically $C_{1-20}$ alkyl, more specifically $C_{1-15}$ alkyl, further more specifically $C_{1-10}$ alkyl, further more specifically $C_{1-6}$ alkyl.

The term "cycloalkyl" refers to a cyclic hydrocarbon radical and includes cyclopropyl, cyclobutyl and cyclopentyl. $C_{3-10}$ cycloalkyl means cycloalkyl having 3-10 cyclic carbon atoms, excluding the number of carbons of a substituent when the $C_{3-10}$ cycloalkyl is substituted. In Chemical Formula 1, the cycloalkyl at $R_1$ may be specifically $C_{3-10}$ cycloalkyl, more specifically $C_{3-8}$ cycloalkyl. According to one embodiment, in Chemical Formula 1, the cycloalkyl at $R_1$ may be specifically $C_{3-10}$ cycloalkyl, more specifically $C_{3-8}$ cycloalkyl. According to one embodiment, in Chemical Formula 1, the cycloalkyl at $R_5$ may be specifically $C_{3-10}$ cycloalkyl, more specifically $C_{6-8}$ cycloalkyl.

The term "alkenyl" refers to linear or branched, unsubstituted or substituted, unsaturated hydrocarbon group having given number of carbons and includes, for example, for example, ethenyl, vinyl, propenyl, allyl, isopropenyl, butenyl, isobutenyl, t-butenyl, n-pentenyl and n-hexenyl. $C_{2-30}$ alkenyl means an alkenyl group having an alkenyl unit of 1 to 30 carbons, excluding the number of carbons of a substituent when the $C_{2-30}$ alkenyl is substituted. According to one embodiment, in Chemical Formula 1, the $C_{2-30}$ alkenyl at $R_5$ may be specifically $C_{2-15}$ alkenyl, more specifically $C_{4-6}$ alkenyl.

The term "cycloalkenyl" refers to a cyclic hydrocarbon group having at least one double bond and includes, for example, for example cyclopentene, cyclohexene and cyclohexadiene, $C_{3-10}$ cycloalkenyl means cycloalkenyl having 3-10 cyclic carbon atoms, excluding the number of carbons of a substituent when the $C_{3-10}$ cycloalkenyl is substituted. According to one embodiment, in Chemical Formula 1, the $C_{3-10}$ cycloalkenyl at $R_1$ may be specifically $C_{3-8}$ cycloalkenyl, more specifically $C_{3-5}$ cycloalkenyl. According to one embodiment, in Chemical Formula 1, the $C_{3-10}$ cycloalkenyl at $R_5$ may be specifically $C_{4-3}$ cycloalkenyl.

The term "alkynyl" refers to a linear or branched, unsubstituted or substituted, unsaturated hydrocarbon group containing designated carbon atoms and includes, for example, ethynyl, propynyl, propagyl, $C_{2-30}$ alkynyl means an alkynyl group having an alkynyl unit of 2 to 30 carbons, excluding the number of carbons of a substituent when the $C_{2-30}$ alkynyl is substituted. According to one embodiment, in Chemical Formula 1, the $C_{2-30}$ alkynyl at $R_5$ may be specifically $C_{2-20}$ alkynyl, more specifically $C_{2-15}$ alkynyl, further more specifically $C_{2-10}$ alkynyl, further more specifically $C_{2-5}$ alkynyl.

The term "heterocycloalkyl containing oxygen, sulfur or nitrogen as a heteroatom" refers to a non-aromatic cyclic hydrocarbon group containing carbon, hydrogen and at least one heteroatom (oxygen, sulfur or nitrogen). The heteroatom may be specifically oxygen or sulfur, more specifically oxygen. According to one embodiment, the number of the heteroatom may be specifically 1-4, more specifically 1-3, further more specifically 1-2, further more specifically 1. $C_{2-15}$ heterocycloalkyl means heterocycloalkyl having 2-15 cyclic carbon atoms. According to one embodiment, in Chemical Formula 1, the heterocycloalkyl at $R_1$ may be specifically $C_{2-40}$ heterocycloalkyl, more specifically $C_{2-8}$ heterocycloalkyl, According to one embodiment, in Chemical Formula 1, the $C_{2-10}$ heterocycloalkyl at $R_5$ may be specifically $C_{2-8}$ heterocycloalkyl.

The term "$C_{3-10}$ heterocycloalkylalkyl containing oxygen, sulfur or nitrogen as a heteroatom" refers to a non-aromatic cyclic hydrocarbon group containing carbon, hydrogen and at least one heteroatom (oxygen, sulfur or nitrogen). The heteroatom may be specifically oxygen or sulfur, more specifically oxygen. According to one embodiment, the number of the heteroatom may be specifically 1-4, more specifically 1-3, further more specifically 1-2, further more specifically 1. $C_{3-15}$ heterocycloalkylalkyl means heterocycloalkylalkyl having 345 cyclic and acyclic carbon atoms. According to one embodiment, it may have 1-5 acyclic carbon atoms. According to one embodiment, in Chemical Formula 1, the heterocycloalkylalkyl at $R_1$ may be specifically $C_{3-15}$ heterocycloalkylalkyl, more specifically $C_{3-10}$ heterocycloalkylalkyl. According to one embodiment, in Chemical Formula 1, the $C_{3-15}$ heterocycloalkylalkyl at $R_5$ may be specifically $C_{3-10}$ heterocycloalkylalkyl, more specifically $C_{5-8}$ heterocycloalkylalkyl.

The term "alkoxyalkyl" refers to an alkyl group substituted with an alkoxy group. $C_{2-30}$ alkoxyalkyl means an alkoxyalkyl group having an alkoxyalkyl unit of 2-30 carbons, excluding the number of carbons of a substituent when the $C_{2-30}$ alkoxyalkyl is substituted. According to one embodiment, in Chemical Formula 1, the $C_{2-30}$ alkoxyalkyl at $R_5$ may be specifically $C_{2-20}$ alkoxyalkyl, more specifically $C_{2-10}$ alkoxyalkyl.

The term "alkoxyalkoxyalkyl" refers to an alkyl group substituted with an alkoxyalkoxy group (alkoxy-alkoxyalkyl-). $C_{3-30}$ alkoxyalkoxyalkyl means an alkoxyalkoxyalkyl group having an alkoxyalkoxyalkyl unit of 3-30 carbons, excluding the number of carbons of a substituent when the $C_{3-30}$ alkoxyalkyl is substituted. According to one embodiment, in Chemical Formula 1, the $C_{3-30}$ alkoxyalkoxyalkyl at $R_5$ may be specifically $C_{3-20}$ alkoxyalkoxyalkyl, more specifically $C_{3-10}$ alkoxyalkoxyalkyl.

The term "heterocycloalkenyl containing oxygen, sulfur or nitrogen as a heteroatom" refers to non-aromatic cyclic hydrocarbon group containing carbon, hydrogen, at least one heteroatom (oxygen, sulfur or nitrogen) and at least one double bond. The heteroatom may be specifically oxygen or sulfur, more specifically oxygen. According to one embodiment, the number of the heteroatoms may be specifically 1-4, more specifically 1-3, further more specifically 1-2, further more specifically 1. $C_{3-10}$ heterocycloalkenyl means heterocycloalkenyl having 3-10 cyclic carbon atoms. According to one embodiment, in Chemical Formula 1, the $C_{3-10}$ heterocycloalkenyl at $R_1$ may be specifically $C_{3-9}$ heterocycloalkenyl, more specifically $C_{3-8}$ heterocycloalkenyl, According to one embodiment, in Chemical Formula 1, the $C_{3-10}$ heterocycloalkenyl at $R_5$ may be specifically $C_{3-9}$ heterocycloalkenyl, more specifically $C_{3-8}$ heterocycloalkenyl.

The term "alcohol" refers to a compound in which a hydroxyl group is bound to the carbon atom of alkyl or a substituted alkyl group. $C_{1-20}$ alcohol means an alcohol compound having an alcohol unit of 1-20 carbons, excluding the number of carbons of a substituent when the $C_{1-20}$ alcohol is substituted, According to one embodiment, in Chemical Formula 1, the $C_{1-20}$ alcohol at $R_5$ may be specifically $C_{3-15}$ alcohol, more specifically $C_{3-10}$ alcohol, further more specifically $C_{5-8}$ alcohol.

The term "alkenol" refers to a compound in which a hydroxyl group is bound to the carbon atom of alkenyl or a substituted alkenyl group. $C_{1-20}$ alkenol means an alkenol compound having an alkenol unit of 1-10 carbons, excluding the number of carbons of a substituent when the $C_{1-20}$ alkenol is substituted. According to one embodiment, in Chemical Formula 1, the $C_{1-20}$ alkenol at $R_5$ may be specifically $C_{3-15}$ alkenol more specifically $C_{3-10}$ alkenol, further more specifically $C_{5-8}$ alkenol.

The term "acyl" refers to a radical derived by the removal of a hydroxyl group from a carboxylic acid. $C_{2-30}$ acyl means an acyl group having an acyl unit of 2-30 carbons, excluding the number of carbons of a substituent when the $C_{2-30}$ acyl is substituted. According to one embodiment, in Chemical Formula 1, the $C_{2-30}$ acyl at $R_5$ may be specifically $C_{2-20}$ acyl, more specifically $C_{2-10}$ acyl.

The term "amide" refers to a functional group comprising an acyl group bound to a nitrogen atom. $C_{1-10}$ amide means an amide group having an amide unit of 1-10 carbons, excluding the number of carbons of a substituent when the $C_{1-10}$ amide is substituted. According to one embodiment, in Chemical Formula 1, the $C_{1-10}$ amide at $R_5$ may be specifically $C_{1-5}$ amide.

The term "amine" refers to a functional group containing a basic nitrogen atom with a one pair. $C_{1-10}$ amine means an amine group having an amine unit of 1-10 carbons, excluding the number of carbons of a substituent when the $C_{1-10}$ amine is substituted. According to one embodiment, in Chemical Formula 1, the $C_{1-10}$ amine at $R_5$ at may be specifically $C_{1-5}$ amine.

The term "ester" refers to a functional group represented by RCOO— (R is alkyl or aryl). $C_{2-15}$ ester means an ester group having an ester unit of 2-15 carbons, excluding the number of carbons of a substituent when the $C_{2-15}$ ester is substituted, According to one embodiment, in Chemical Formula 1, the $C_{2-15}$ ester at $R_5$ may be specifically $C_{2-10}$ ester.

The term "sulfate" refers to a functional group represented by —$SO_4$.

The term "carboxyl" refers to a functional group represented by —COOH.

The term "carboxyalkyl" refers to an alkyl group to which carboxyl is bound. $C_{3-20}$ carboxyalkyl means a carboxyalkyl group having a carboxyalkyl unit of 3-20 carbons, excluding the number of carbons of a substituent when the $C_{3-20}$ carboxyalkyl is substituted. $C_{3-20}$ carboxyalkyl means a carboxyalkyl group having a carboxyalkyl unit of 3-20 carbons, excluding the number of carbons of a substituent when the $C_{3-20}$ carboxyalkyl is substituted. According to one embodiment, in Chemical Formula 1, the $C_{2-30}$ carboxyalkyl at $R_5$ may be specifically $C_{3-15}$ carboxyalkyl, more specifically $C_{4-10}$ carboxyalkyl.

The term "carboxyalkenyl" refers to an alkenyl group to which carboxyl is bound. $C_{3-20}$ carboxyalkenyl means a carboxyalkenyl group having a carboxyalkenyl unit of 3-20 carbons, excluding the number of carbons of a substituent when the $C_{3-20}$ carboxyalkenyl is substituted. According to one embodiment, in Chemical Formula 1, the $C_{3-20}$ carboxyalkenyl at $R_5$ may be specifically $C_{3-10}$ carboxyalkenyl, more specifically $C_{3-6}$ carboxyalkenyl.

The term "alkylcarboxyl" refers to a carboxyl group to which alkyl is bound. $C_{3-20}$ aikylcarboxyl means an alkylcarboxyl group having an alkylcarboxyl unit of 3-20 carbons, excluding the number of carbons of a substituent when the $C_{3-20}$ aikylcarboxyl is substituted. According to one embodiment, in Chemical Formula 1, the $C_{3-20}$ alkylcarboxyl at $R_5$ may be specifically $C_{3-10}$ alkylcarboxyl more specifically $C_{3-6}$ alkylcarboxyl.

The term "alkenylcarboxy" refers to a carboxyl group to which alkenyl is bound. $C_{3-20}$ alkenylcarboxyl means an alkenylcarboxyl group having an alkenylcarboxyl unit of 3-20 carbons, excluding the number of carbons of a substituent when the $C_{3-20}$ alkenylcarboxyl is substituted. According to one embodiment, in Chemical Formula 1, the $C_{3-20}$ alkenylcarboxyl at $R_5$ may be specifically $C_{3-10}$ alkenylcarboxyl more specifically $C_{3-6}$ alkenylcarboxyl.

The term "alkylcarboxyalkyl" refers to an alkyl-C(O)—O-alkyl group. $C_{3-20}$ alkylcarboxyalkyl means an alkylcarboxyalkyl group having an alkylcarboxyalkyl unit of 3-20 carbons, excluding the number of carbons of a substituent when the $C_{3-20}$ alkylcarboxyalkyl is substituted. According to one embodiment, in Chemical Formula 1, the $C_{3-20}$ alkylcarboxyalkyl at $R_5$ may be specifically $C_{3-10}$ alkylcarboxyalkyl.

The term "alkylcarboxyalkenyl" refers to an alkyl-O—C(O)-alkenyl group. $C_{3-20}$ alkylcarboxyalkenyl means an alkylcarboxyalkenyl group having an alkylcarboxyalkenyl unit of 3-20 carbons, excluding the number of carbons of a substituent when the $C_{3-20}$ alkylcarboxyalkenyl is substituted. According to one embodiment, in Chemical Formula 1, the $C_{3-20}$ alkylcarboxyalkenyl at $R_5$ may be specifically $C_{3-10}$ alkylcarboxyalkenyl, more specifically $C_{3-6}$ alkylcarboxyalkenyl.

The term "alkenylcarboxyalkyl" refers to an alkenyl-O—C(O)-alkyl group. $C_{3-20}$ alkenylcarboxyalkyl means an alkenylcarboxyalkyl group having an alkenylcarboxyalkyl unit of 3-20 carbons, excluding the number of carbons of a substituent when the $C_{3-20}$ alkenylcarboxyalkyl is substituted. According to one embodiment, in Chemical Formula 1, the alkenylcarboxyalkyl at $R_5$ may be specifically $C_{3-10}$ alkenylcarboxyalkyl, more specifically $C_{3-6}$ alkenylcarboxyalkyl.

The term "alkenylcarboxyalkenyl" refers to an alkenyl-O—C(O)-alkenyl group. $C_{4-20}$ alkenylcarboxyalkenyl means an alkenylcarboxyalkenyl group having an alkenylcarboxyalkenyl unit of 4-20 carbons, excluding the number of carbons of a substituent when the $C_{4-20}$ alkenylcarboxyalkenyl is substituted, According to one embodiment, in Chemical Formula 1, the $C_{4-20}$ alkenylcarboxyalkenyl at $R_5$ may be specifically $C_{1-10}$ alkenylcarboxyalkenyl.

The term "aryl" refers to a substituted or unsubstituted, monocyclic or polycyclic carbon ring which is entirely or partially unsaturated. $C_{6-30}$ aryl means an aryl group having 6-30 cyclic carbon atoms, excluding the number of carbons of a substituent when the $C_{5-30}$ aryl is substituted. According to one embodiment, the aryl may be monoaryl or biaryl. According to one embodiment, the monoaryl may have 5-6 carbons, and the biaryl may have 9-10 carbons, According to one embodiment, the aryl may be substituted or unsubstituted phenyl. When the monoaryl, e.g. phenyl, is substituted, it may have various substituents at various positions. For example, it may be substituted with halo, hydroxy, nitro, cyano, $C_1$-$C_4$ substituted or unsubstituted, linear or branched alkyl, alkylcarboxylnitro or a combination thereof.

The term "aralkyl" refers to an alkyl group substituted with an aryl group. $C_{6-30}$ aralkyl means aralkyl having an aralkyl unit of 6-30 carbons, excluding the number of carbons of a substituent when the $C_{6-30}$ aralkyl is substituted. In the aralkyl the aryl may be specifically monoaryl or biaryl, and the alkyl may be specifically $C_{1-3}$ alkyl, more specifically $C_1$ alkyl. In the aralkyl, the aryl may have various substituents at various positions. For example, it may be substituted with halo, hydroxy, nitro, cyano, $C_1$-$C_4$ substituted or unsubstituted, linear or branched alkyl, $C_1$-$C_4$ linear or branched alkoxy, alkylcarboxylnitro or a combination thereof.

The term "alkaryl" refers to an aryl group substituted with an alkyl group. $C_{6-30}$ alkaryl means alkaryl having an alkaryl unit of 6-30 carbons, excluding the number of carbons of a substituent when the $C_{6-30}$ alkaryl is substituted. In the alkaryl, the aryl may be specifically monoaryl or biaryl, and the alkyl may be specifically $C_{1-10}$ alkyl, more specifically $C_{1-5}$ alkyl. In the alkaryl, the aryl may have various substituents at various positions. For example, it may be substituted with halo, hydroxy, nitro, cyano, $C_1$-$C_4$ substituted or unsubstituted, linear or branched alkyl, or $C_1$-$C_4$ linear or branched alkoxy, alkylcarboxylnitro or a combination thereof.

The term "heteroaryl containing oxygen, sulfur or nitrogen as a heteroatom" refers to a heterocyclic aromatic group which contains O, S or N as a heteroatom. $C_{3-30}$ heteroaryl means a heteroaryl group having a cyclic carbon atom of 3-30 carbons, excluding the number of carbons of a substituent when the $C_{3-30}$ heteroaryl is substituted. The number of the heteroatoms may be 1-4, specifically 1-2. In the heteroaryl, the aryl may be specifically monoaryl or biaryl, most specifically monoaryl. The heteroaryl may have various substituents at various positions. For example, it may be substituted with halo, hydroxy, nitro, cyano, $C_4$ substituted or unsubstituted, linear or branched alkyl, $C_1$-$C_4$ linear or branched alkoxy, alkylcarboxylnitro or a combination thereof.

In a specific embodiment, the aryl or heteroaryl includes, but is not limited to, phenyl, benzyl, naphthyl, pyroil, pyrrolidinyl, pyridinyl, pyrimidinyl, purinyl, quinolinyl, isoquinolinyl, puryl, thiophenyl imidazolyl, oxazolyl, thiazolyl, pyrazolyl and thienyl.

The term "arylcarbonyl" refers to "aryl-C(O)—". $C_{6-30}$ arylcarbonyl means arylcarbonyl having an arylcarbonyl unit of 6-30 carbons, excluding the number of carbons of a substituent when the $C_{6-30}$ arylcarbonyl is substituted. In the arylcarbonyl, the aryl may be specifically monoaryl or biaryl, more specifically monoaryl. In the arylcarbonyl, the aryl may have various substituents at various positions. For example, it may be substituted with halo, hydroxy, nitro, cyano, $C_1$-$C_4$ substituted or unsubstituted, linear or branched alkyl, $C_1$-$C_4$ linear or branched alkoxy, alkylcarboxylnitro or a combination thereof.

In one embodiment of the present disclosure, $R_1$ is hydrogen, halo, $C_{3-8}$ cycloalkyl, $C_{3-8}$ cycloalkenyl, $C_{2-8}$ heterocycloalkyl containing oxygen, sulfur or nitrogen as a heteroatom, $C_{3-10}$ heterocycloalkylalkyl containing oxygen, sulfur or nitrogen as a heteroatom, $C_{3-8}$ heterocycloalkenyl containing oxygen, sulfur or nitrogen as a heteroatom, $C_{6-10}$ aryl, $C_{6-15}$ aralkyl, $C_{6-15}$ alkaryl or $C_{3-15}$ heteroaryl containing oxygen, sulfur or nitrogen as a heteroatom. In a specific embodiment, $R_1$ is $C_{5-8}$ heterocycloalkenyl containing oxygen, sulfur or nitrogen as a heteroatom.

As demonstrated through our prior experimentation results (Korean Patent Publication No, 2010-0047170), when $R_1$ is heterocycloalkyl and heterocycloalkenyl, the effect of preventing or treating vascular leakage is very superior. In a specific embodiment, when $R_1$ is heterocycloalkyl, it may not unsubstituted. In a specific embodiment, when $R_1$ is heterocycloalkenyl, it may be substituted with $C_{2-8}$ alkylcarboxyl (for example, $CH_3CO$—O—) and/or $C_{3-8}$ alkylcarboxylalkyl (for example, ($CH_3CO$—O—$CH_2$—).

In an another embodiment of the present disclosure, $R_5$ is hydrogen, $C_{1-10}$ alkyl, $C_{3-8}$ cycloalkyl, $C_{2-10}$ alkenyl, $C_{3-8}$ cycloalkenyl, $C_{2-10}$ alkynyl, $C_{2-8}$ heterocycloalkyl containing oxygen, sulfur or nitrogen as a heteroatom, $C_{3-10}$ heterocycloalkylalkyl containing oxygen, sulfur or nitrogen as a heteroatom, $C_{2-20}$ alkoxyalkyl, $C_{3-20}$ alkoxyalkoxyalkyl, $C_{3-8}$ heterocycloalkenyl containing oxygen, sulfur or nitrogen as a heteroatom, $C_{1-10}$ alcohol, $C_{3-10}$ alkenol, $C_{2-20}$ acyl, $C_{1-5}$ amide, $C_{1-5}$ amine, $C_{2-10}$ ester, sulfate, carboxyl, $C_{3-10}$ carboxyalkyl, $C_{3-10}$ carboxyalkenyl, $C_{3-10}$ alkylcarboxyl, $C_{3-10}$ alkenylcarboxyl, $C_{3-10}$ alkylcarboxyalkyl, $C_{3-10}$ alkylcarboxyalkenyl, $C_{3-10}$ alkenylcarboxyalkyl, $C_{1-10}$ alkenylcarboxyalkenyl, $C_{6-20}$ aryl, $C_{6-20}$ aralkyl, $C_{6-20}$ alkaryl, $C_{3-20}$ heteroaryl containing oxygen, sulfur or nitrogen as a heteroatom or $C_{6-20}$ arylcarbonyl.

In a specific embodiment, $R_5$ is $C_{1-6}$ alkyl, $C_{6-8}$ cycloalkyl, $C_{4-6}$ alkenyl, $C_{4-8}$ cycloalkenyl, $C_{2-5}$ alkynyl, $C_{6-15}$ aryl, $C_{6-15}$ aralkyl or $C_{3-15}$ heteroaryl containing oxygen, sulfur or nitrogen as a heteroatom.

In one embodiment of the present disclosure, in $R_5$, the cycloalkyl or heterocycloalkyl may be substituted with hydroxy, halo, $C_{1-5}$ alkyl, $C_{1-5}$ alcohol, $C_{1-5}$ alkoxy. $C_{2-8}$ alkoxyalkyl, $C_{6-20}$ aryl, $C_{7-20}$ arylcarboxyl or a combination thereof; the $C_{3-10}$ cycloalkenyl or heterocycloalkenyl may be substituted with hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, $C_{7-20}$ arylcarboxyl or a combination thereof; the aryl may be substituted with hydroxy, halo, $C_{1-5}$ alkyl, $C_{1-5}$ alcohol, $C_{1-5}$ alkoxy, $C_{2-8}$ alkoxyalkyl, nitro, cyano, $C_{2-8}$ alkylcarboxylnitro or a combination thereof; the aralkyl may be substituted with hydroxy, halo, $C_{1-5}$ alkyl, $C_{1-5}$ alcohol, $C_{1-5}$ alkoxy, $C_{2-8}$ alkoxyalkyl, nitro, cyano, $C_{2-8}$ alkylcarboxylnitro or a combination thereof; the heteroaryl may be substituted with hydroxy, halo, $C_{1-5}$ alkyl, $C_{1-5}$ alcohol, $C_{1-5}$ alkoxy, $C_{2-8}$ alkoxyalkyl, nitro, cyano, $C_{2-8}$ alkylcarboxylnitro or a combination thereof; and the arylcarbonyl may be substituted with hydroxy, halo, $C_{1-5}$ alkyl(alcohol, $C_{1-5}$ alkoxy, $C_{2-8}$ alkoxyalkyl, nitro, $C_{2-8}$ alkylcarboxylamino or a combination thereof.

In Chemical Formula 1, X may be oxygen or sulfur, specifically oxygen.

In one embodiment of the present disclosure, in Chemical Formula 1, X is oxygen; $R_1$ is hydrogen, halo, $C_{3-8}$ cycloalkyl, $C_{3-8}$ cycloalkenyl, $C_{2-8}$ heterocycloalkyl containing oxygen, sulfur or nitrogen as a heteroatom, $C_{3-10}$ heterocycloalkylalkyl containing oxygen, sulfur or nitrogen as a heteroatom, $C_{3-8}$ heterocycloalkenyl containing oxygen, sulfur or nitrogen as a heteroatom, $C_{6-10}$ aryl, $C_{6-15}$ aralkyl, $C_{6-15}$ alkaryl or $C_{3-15}$ heteroaryl containing oxygen, sulfur or nitrogen as a heteroatom; $R_2$ and $R_3$ are independently hydrogen or $C_{1-10}$ alkyl; $R_4$ is hydrogen, hydroxy or $C_{1-10}$ alkyl; $R_5$ is hydrogen, $C_{3-10}$ alkyl, $C_{3-8}$ cycloalkyl, $C_{2-10}$ alkenyl, $C_{3-8}$ cycloalkenyl, alkynyl, $C_{2-8}$ heterocycloalkyl containing oxygen, sulfur or nitrogen as a heteroatom, $C_{3-10}$ heterocycloalkylalkyl containing oxygen, sulfur or nitrogen as a heteroatom, $C_{2-20}$ alkoxyalkyl, $C_{3-20}$ alkoxyalkoxyalkyl, $C_{3-8}$ heterocycloalkenyl containing oxygen, sulfur or nitrogen as a heteroatom, $C_{1-10}$ alcohol, $C_{1-10}$ alkenol, $C_{2-20}$ acyl, $C_{1-5}$ amide, $C_{1-5}$ amine, $C_{2-10}$ ester, sulfate, carboxyl, $C_{3-10}$ carboxyalkyl, $C_{3-10}$ carboxyalkenyl, $C_{3-10}$ alkylcarboxyl, $C_{3-10}$ alkenylcarboxyl, $C_{3-10}$ alkylcarboxyalkyl, $C_{3-10}$ alkylcarboxyalkenyl, $C_{3-10}$ alkenylcarboxyalkyl, $C_{4-10}$ alkenylcarboxyalkenyl, $C_{6-20}$ aryl, $C_{6-20}$ aralkyl, $C_{6-20}$ alkaryl, $C_{3-20}$ heteroaryl containing oxygen, sulfur or nitrogen as a heteroatom or $C_{6-20}$ arylcarbonyl.

In one embodiment of the present disclosure, the ginsenoside Rk1 analog of the present disclosure is a compound represented by a chemical formula selected from the group consisting of Chemical Formulae 3 to 36, or a pharmaceutically acceptable salt thereof:

Chemical Formula 3
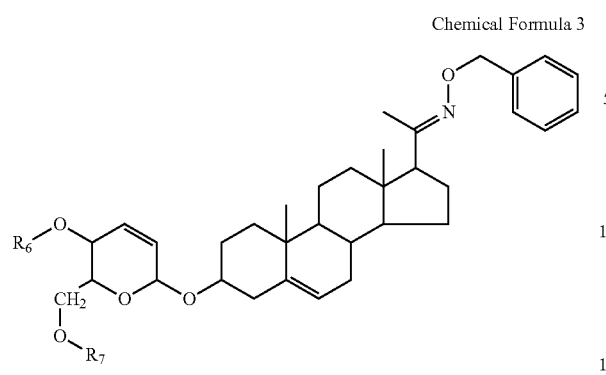
Chemical Formula 4
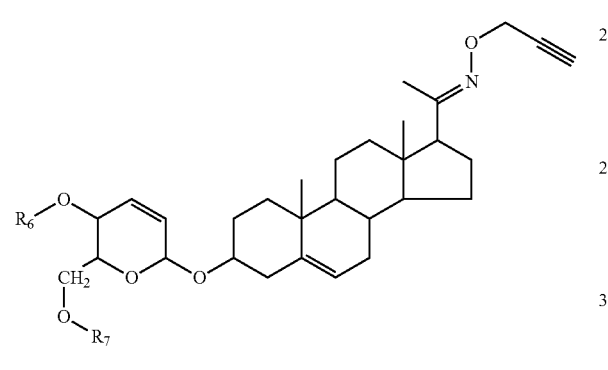
Chemical Formula 5
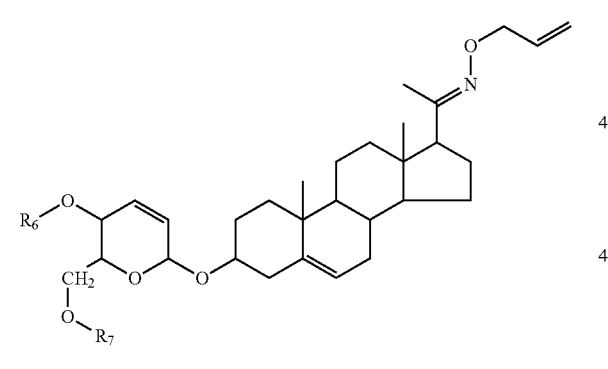
Chemical Formula 6
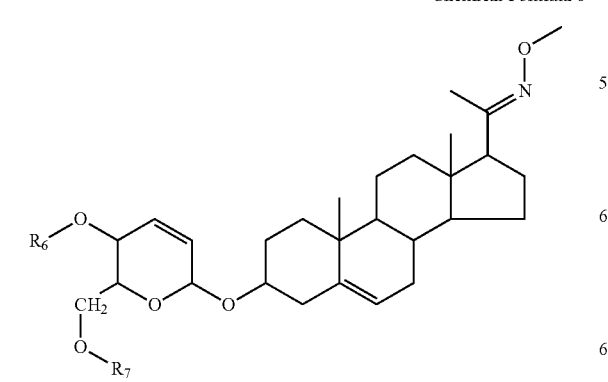
Chemical Formula 7
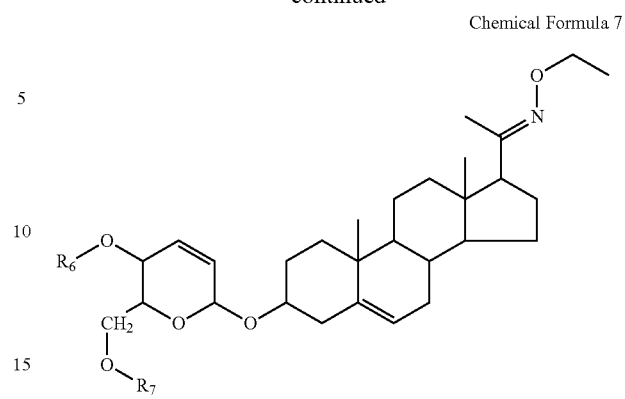
Chemical Formula 8
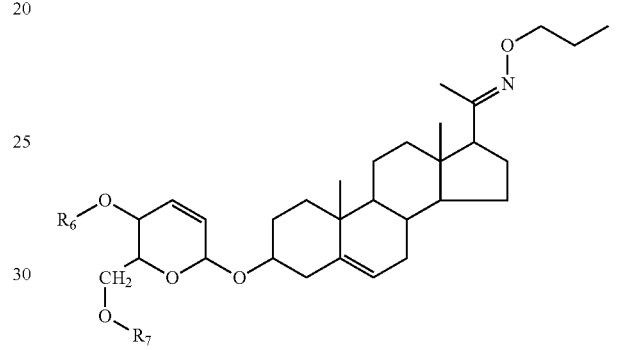
Chemical Formula 9
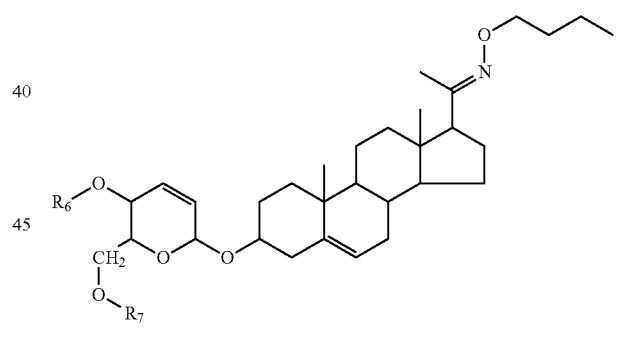
Chemical Formula 10
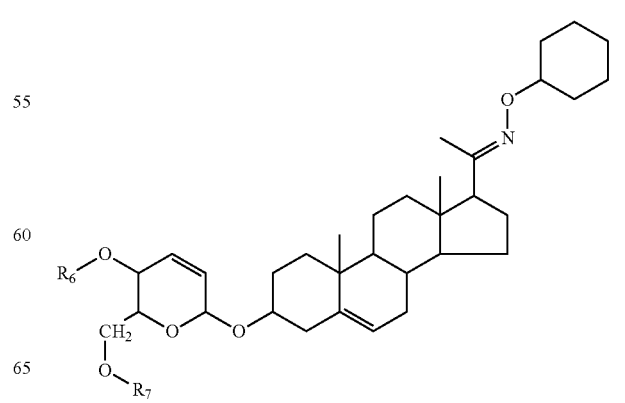

Chemical Formula 11
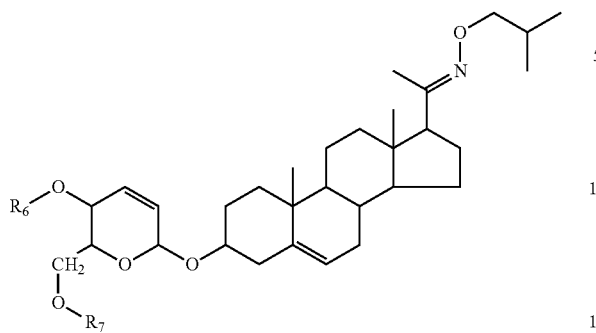
Chemical Formula 12
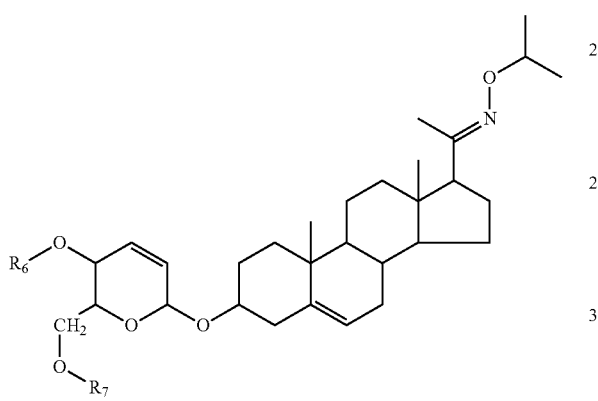
Chemical Formula 13
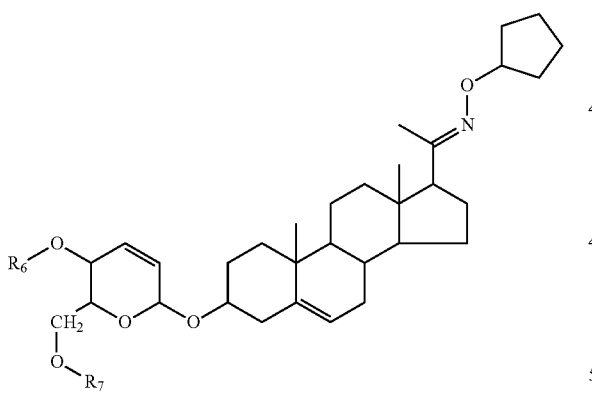
Chemical Formula 14
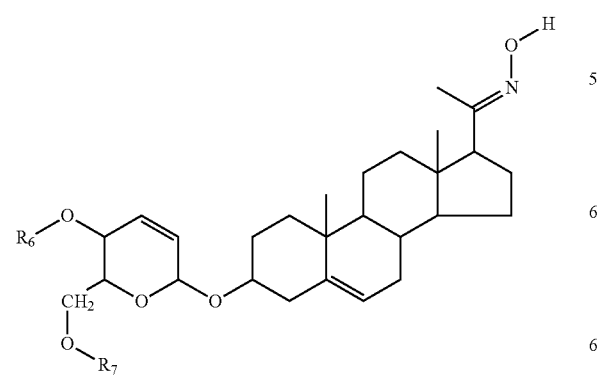
Chemical Formula 15
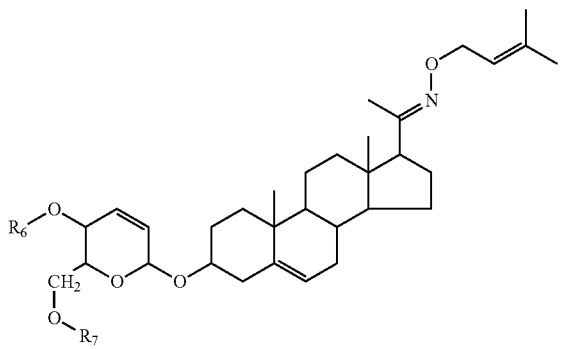
Chemical Formula 16
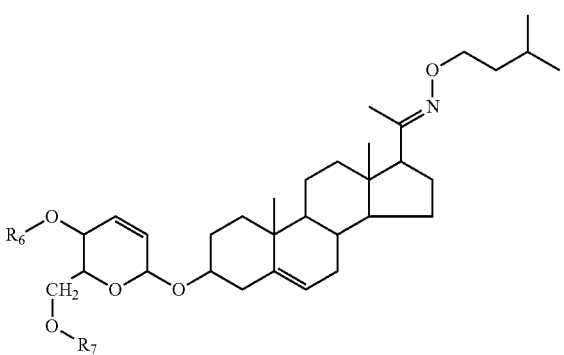
Chemical Formula 17
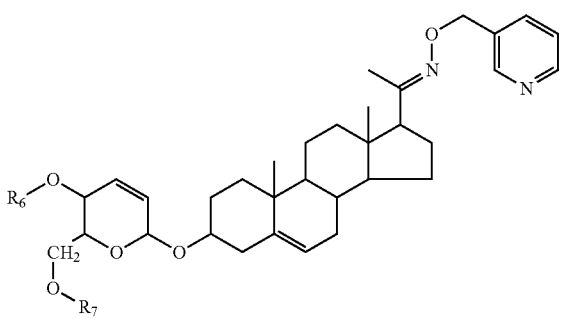
Chemical Formula 18
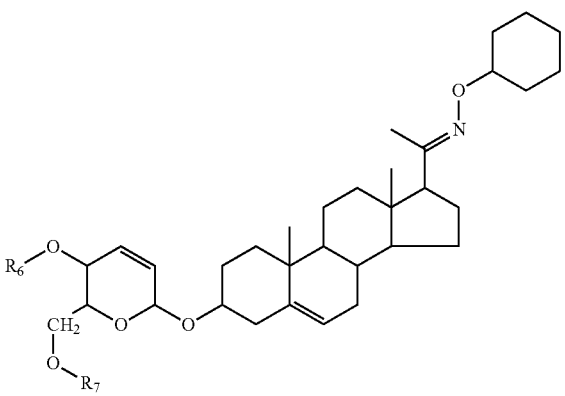

Chemical Formula 19
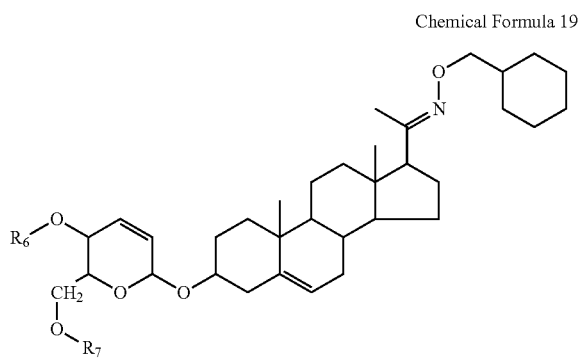
Chemical Formula 20
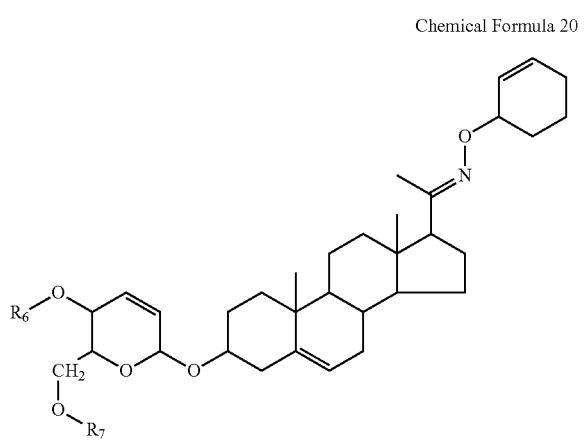
Chemical Formula 21
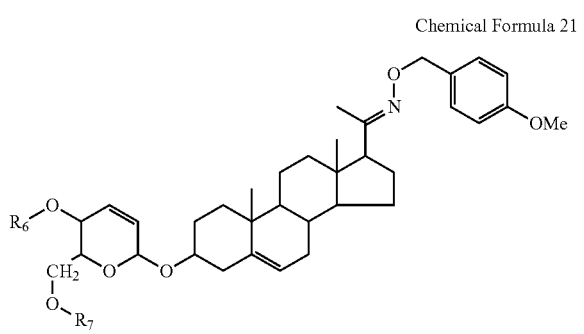
Chemical Formula 22
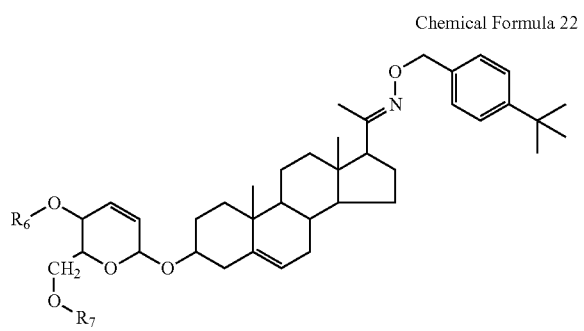
Chemical Formula 23
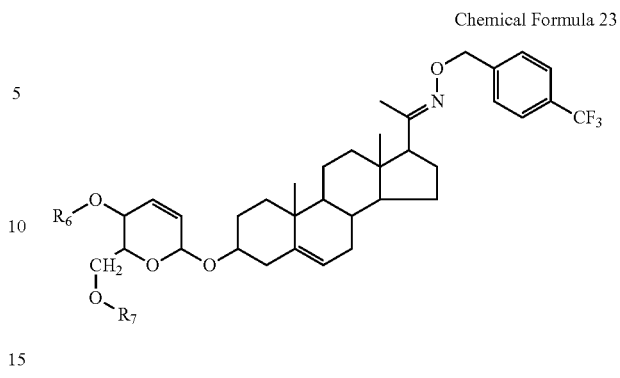
Chemical Formula 24
Chemical Formula 25
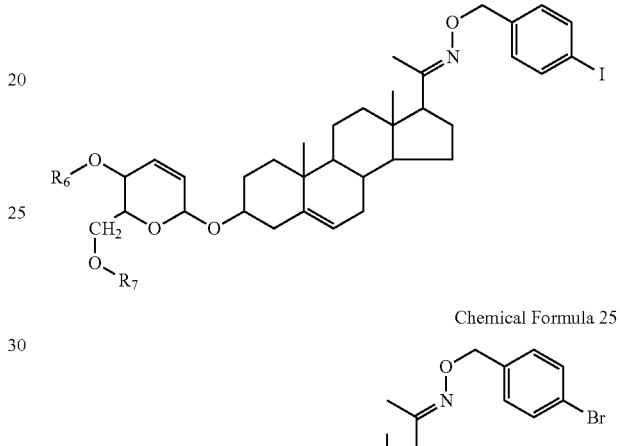
Chemical Formula 26
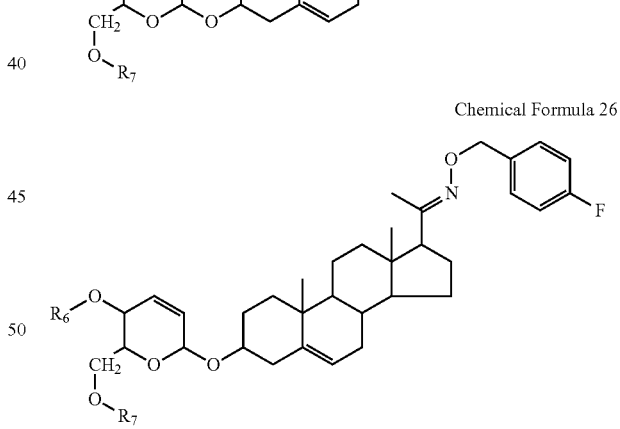
Chemical Formula 27
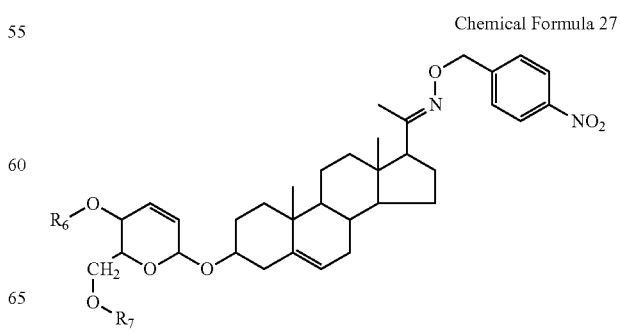

Chemical Formula 28
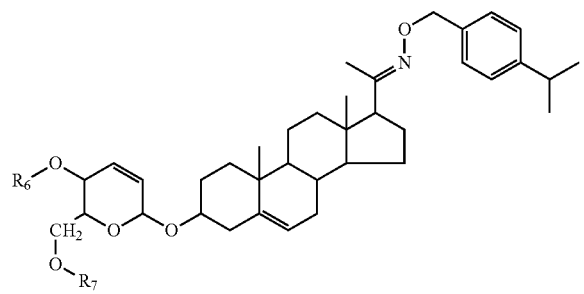
Chemical Formula 29
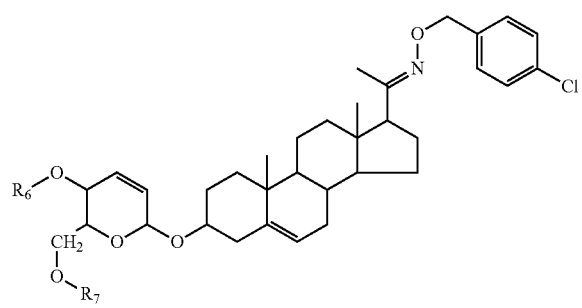
Chemical Formula 30
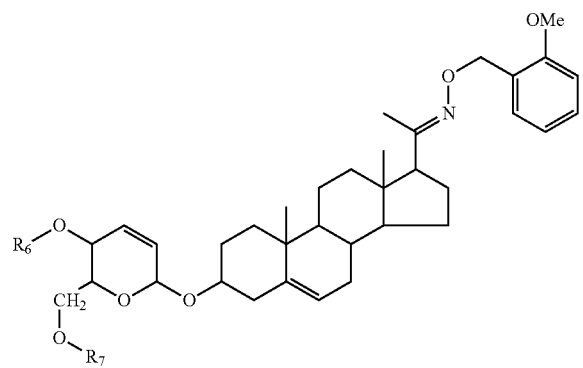
Chemical Formula 31
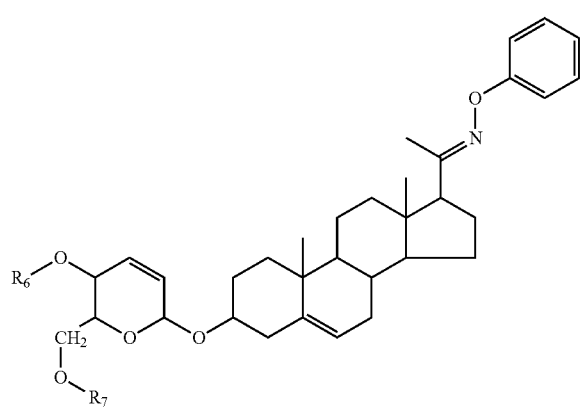
Chemical Formula 32
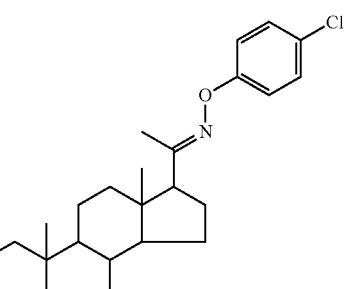
Chemical Formula 33
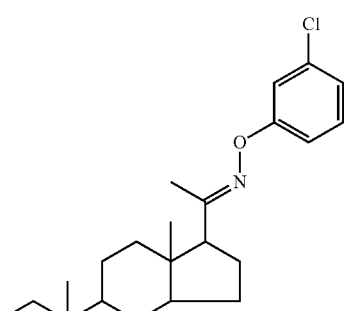
Chemical Formula 34
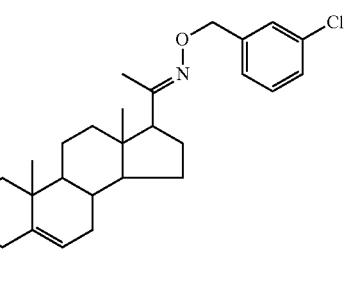
Chemical Formula 35
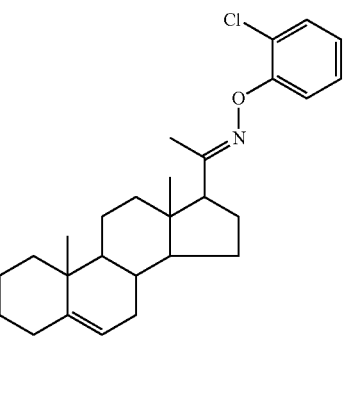

-continued

Chemical Formula 36

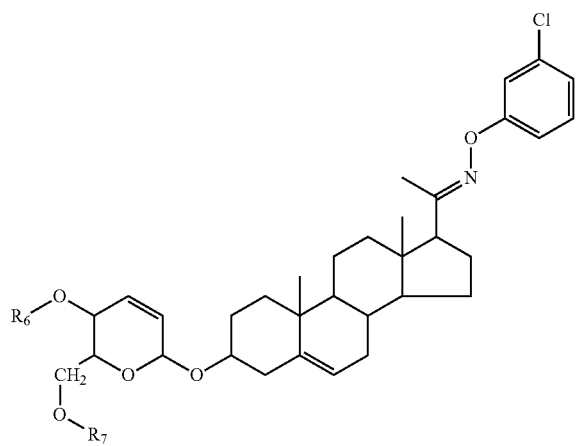

In the Chemical Formulae 3 to 36, $R_6$ and $R_7$ is independently hydrogen or $C_{1-10}$ alkyl.

In a specific embodiment of the present disclosure, the compound represented by Chemical Formulae 3 to 36 is represented by the following Chemical Formulae 37 to 70:

Chemical Formula 37

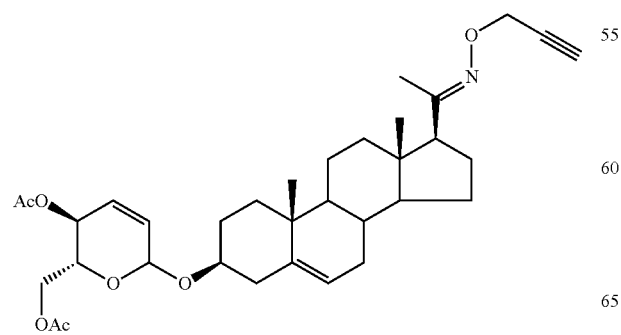

Chemical Formula 38

-continued

Chemical Formula 39

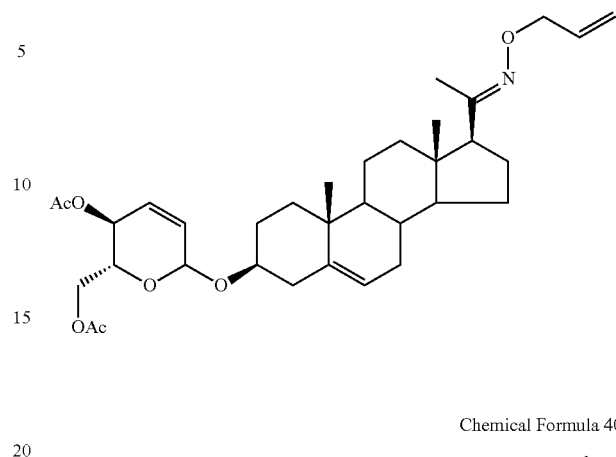

Chemical Formula 40

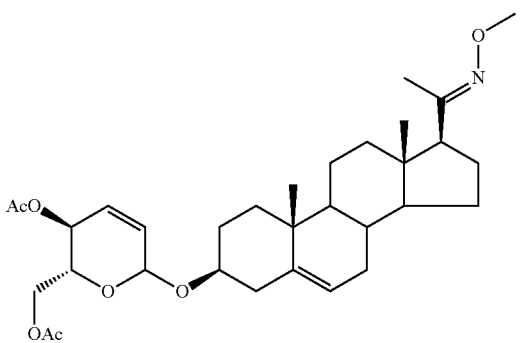

Chemical Formula 41

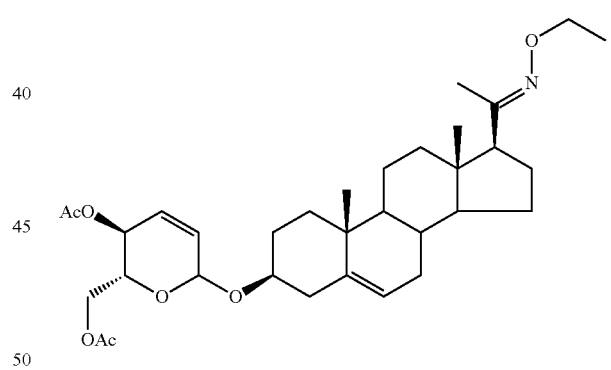

Chemical Formula 42

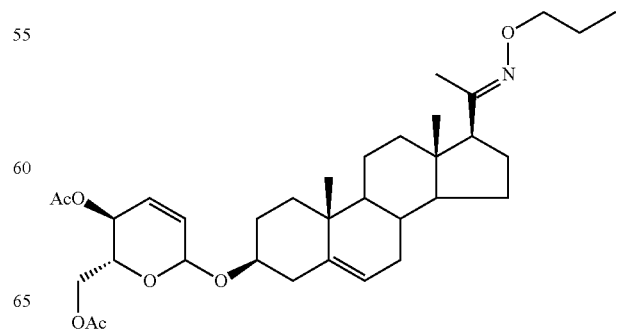

Chemical Formula 43
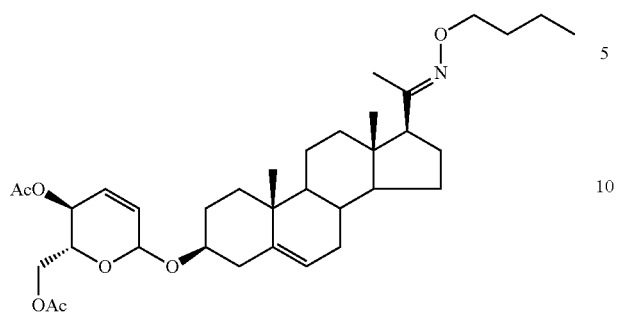
Chemical Formula 44
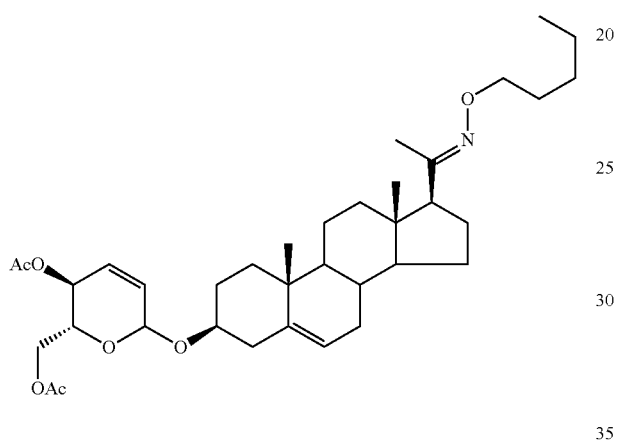
Chemical Formula 45
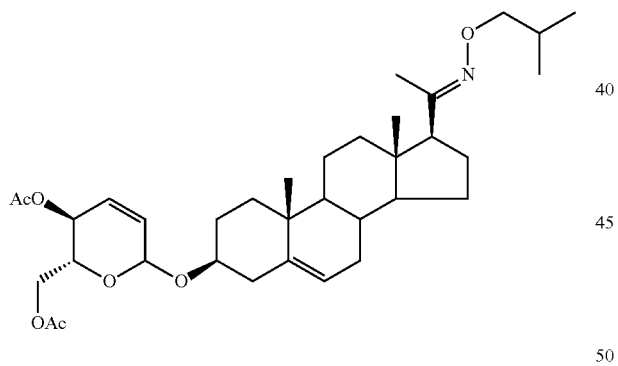
Chemical Formula 46
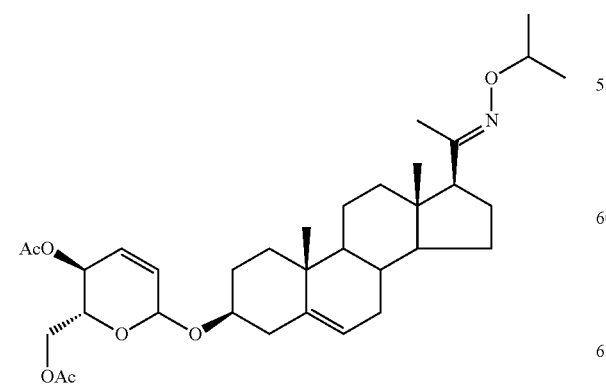
Chemical Formula 47
Chemical Formula 48
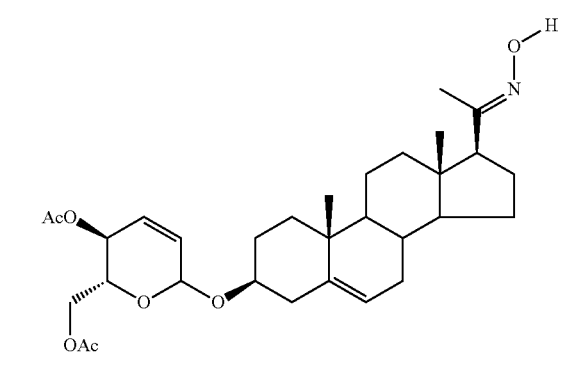
Chemical Formula 49
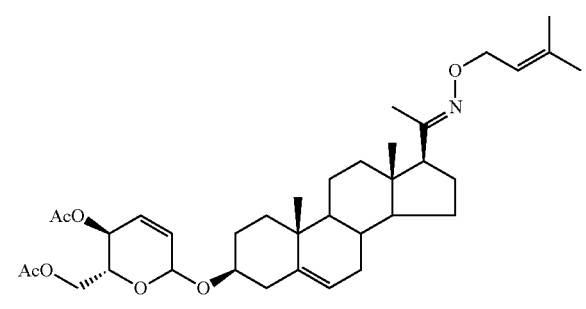
Chemical Formula 50
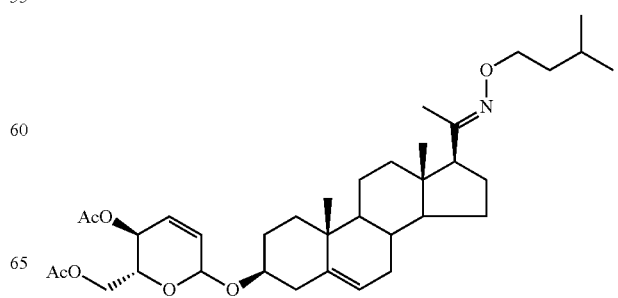

Chemical Formula 51
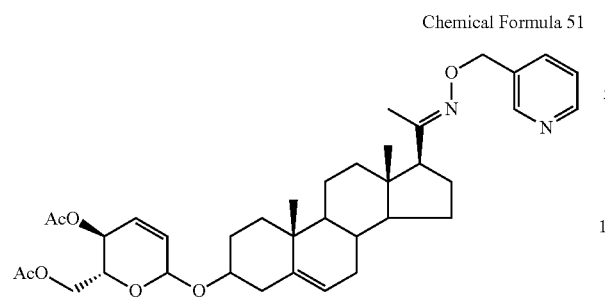
Chemical Formula 52
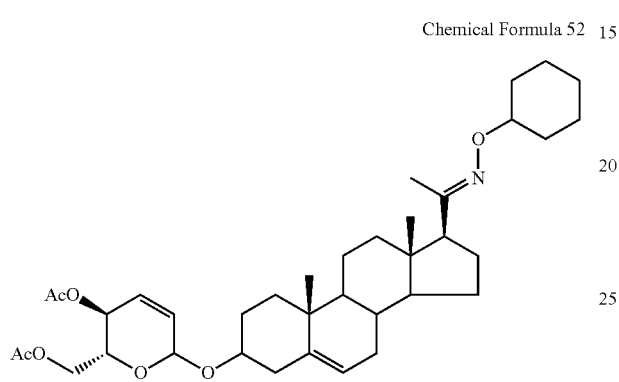
Chemical Formula 53
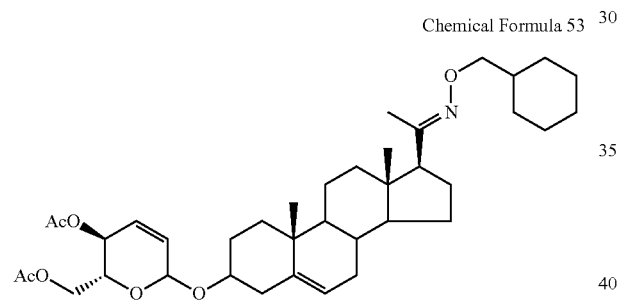
Chemical Formula 54
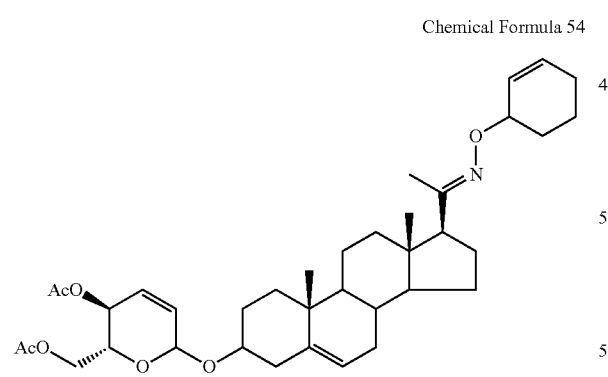
Chemical Formula 55
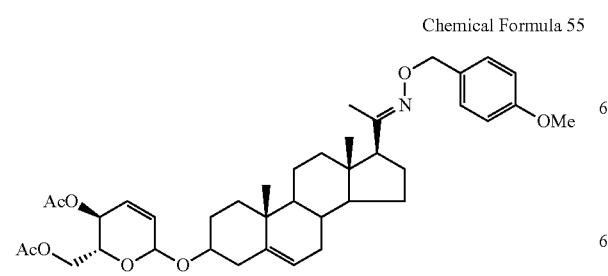
Chemical Formula 56
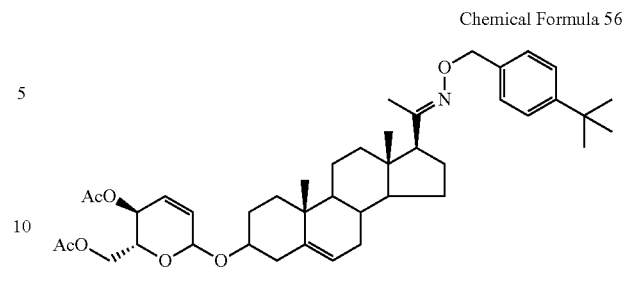
Chemical Formula 57
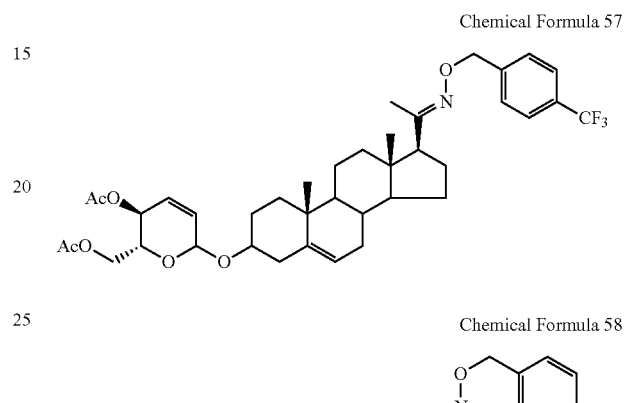
Chemical Formula 58
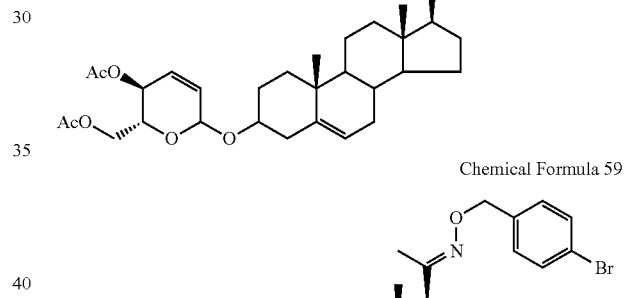
Chemical Formula 59
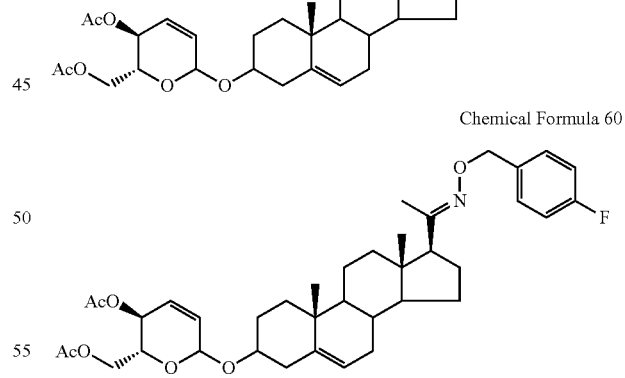
Chemical Formula 60
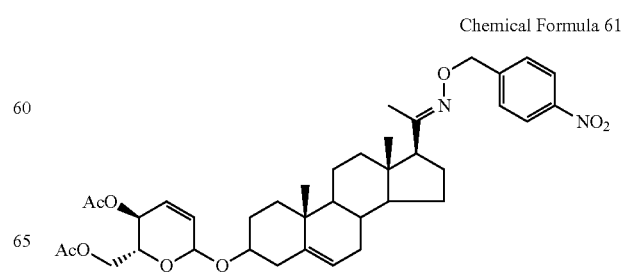
Chemical Formula 61
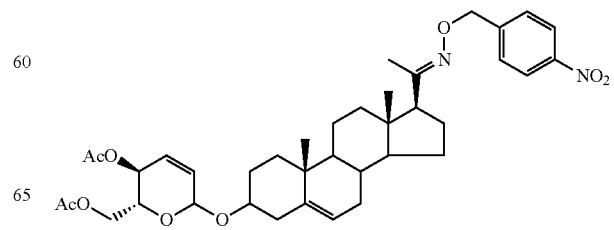

Chemical Formula 62

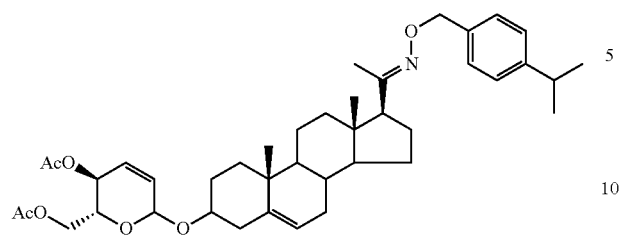

Chemical Formula 63

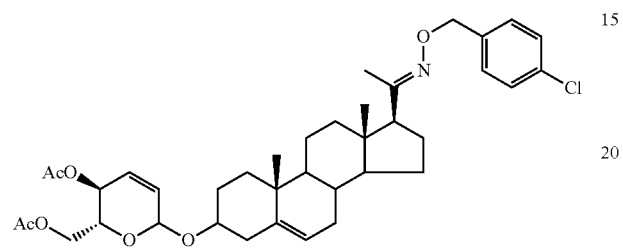

Chemical Formula 64

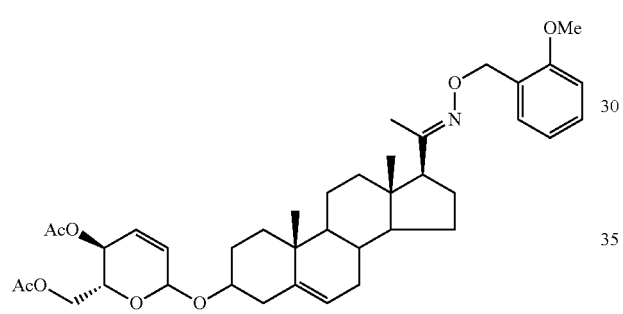

Chemical Formula 65

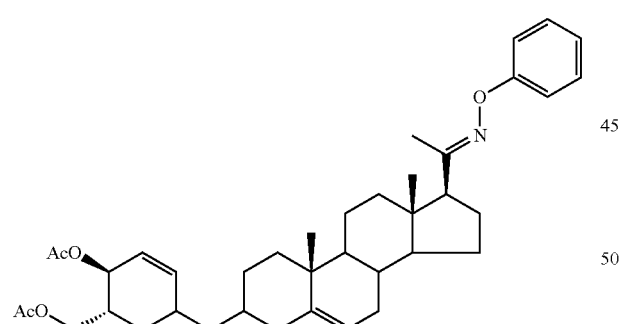

Chemical Formula 66

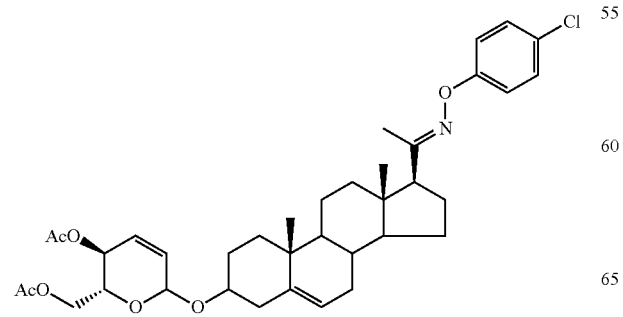

Chemical Formula 67

Chemical Formula 68

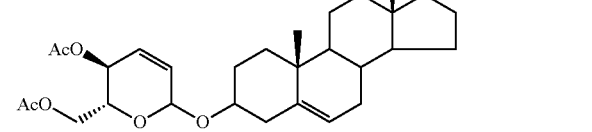

Chemical Formula 69

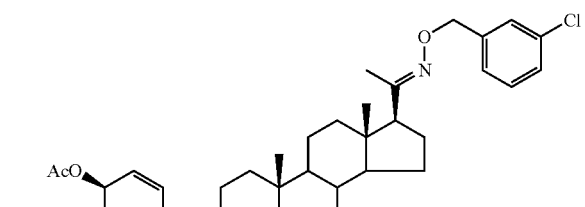

Chemical Formula 70

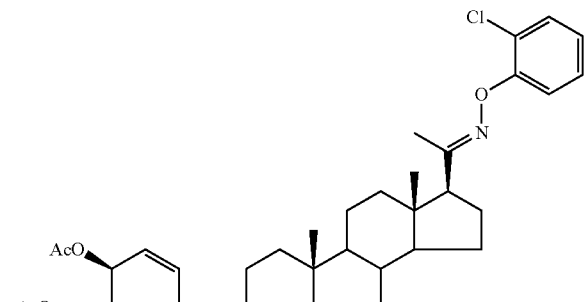

wherein Ac is acetyl.

The compounds of the present disclosure may have one or more chiral center and/or geometric isomeric center, and the present disclosure includes all stereoisomers, i.e., optical isomers, diastereoisomers and geometric isomers, of the compound represented by Chemical Formula 1. In addition, the present invention includes solvates and hydrates of the compound represented by Chemical Formula 1.

The term "pharmaceutically acceptable salt" refers to a formulation of a compound that does not cause significant irritation to an organism to which it is administered and does not abrogate the biological activity and properties of the compound. The pharmaceutically acceptable salt can be obtained by allowing the compound of the present invention to react with inorganic adds such as hydrochloric add, bromic add, sulfuric add, nitric add, phosphoric add; sulfonic adds such as methanesulfonic add, ethanesulfonic add, and p-toluenesulfonic add; or organic carbonic adds such as tartaric add, formic add, citric add, acetic add, trichloroacetic add, trifluoroacetic add, capric acid, isobutene add, malonic add, succinic add, phthalic acid, gluconic acid, benzoic add, lactic add, fumaric acid, maleic add and salicylic add; hydrobromic add and hydroiodic add. Also, the salts may be obtained by allowing the compound of the present invention with bases to form with alkali metal bases such as ammonium salt, sodium salt or potassium salt; alkaline earth metal bases such as calcium salt and magnesium salt; salts with organic bases such as dicyclohexylamine, N-methyl-D-glucamine and tris (hydroxymethyl)methylamine; or salts with amino adds such as arginine and lysine.

The Rk1 analog of the present disclosure is very effective in preventing or treating vascular leakage. The diseases associated with vascular leakage that may be prevented or treated by the Rk1 analog of the present disclosure include diabetes, inflammation, retinopathy, diabetic retinopathy, macular degeneration, glaucoma, stricture, restricture, arteriosclerosis, atherosclerosis, cerebral edema, arthritis, arthropathy, uveitis, inflammatory bowel disease, macular edema, cancer, hyperlipidemia, ischemic disease, diabetic foot ulcer, pulmonary hypertension, acute lung injury, myocardial ischemia, heart failure, acute limb ischemia, myocardial infarction, stroke, ischemia, reperfusion injury, vascular leakage syndrome (VLS), edema, transplant rejection, burn, acute or adult respiratory distress syndrome (ARDS), sepsis or autoimmune disease. For example, when the composition of the present disclosure is used for prevention or treatment of restricture, the composition of the present disclosure may be coated on a stent.

When the composition of the present disclosure is used for prevention or treatment of cancer, the composition of the present disclosure, it may be used either alone or in combination with other commonly used chemotherapies or radiation therapies. The combination therapy may be more effective in treating cancer. The chemotherapy agents that may be used together with the composition of the present disclosure include cisplatin, carboplatin, procarbazine, mechlorethamine, cyclophosphamide, ifosfamide, daunorubicin, doxorubicin, tamoxifen, taxol, 5-fluorouracil and methotrexate etc. The radiation therapies that may be used together with the composition of the present disclosure include X-ray radiation, γ-ray radiation, etc.

In one embodiment, the subject is a mammal. In a specific embodiment, the mammal is a human.

The Rk1 analog of the present disclosure may be provided as a pharmaceutical composition, a food composition or a cosmetic composition.

When the composition of the present disclosure is prepared into a pharmaceutical composition, the pharmaceutical composition of the present disclosure comprises a pharmaceutically acceptable carrier. The pharmaceutically acceptable carrier included in the pharmaceutical composition of the present disclosure may be a commonly used one, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present disclosure may be administered orally or parenterally. When administered parenterally, it may be administered intravenously, subcutaneously, intramuscularly, intraabdominally, transdermally, or the like.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-1000 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

When the composition of the present disclosure is prepared as a food composition, the composition of the present disclosure may comprise ingredients commonly added for preparation of food. For example, flavor or natural carbohydrate may be added. The natural carbohydrate may be, for example, a monosaccharide (e.g. glucose, fructose, etc., a disaccharide (e.g. maltose, sucrose, oligosaccharide, etc., an oligosaccharide, a polysaccharide (e.g. dextrin, cyclodextrin, etc. or a sugar alcohol (e.g. xylitol, sorbitol, erythritol, etc.). The flavor may be a natural flavor (e.g. thaumatin, *stevia* extract) or a synthetic flavor (e.g. saccharin, aspartame, etc.).

When the composition of the present disclosure is prepared as a cosmetic composition (in particular, a functional cosmetic composition), it may comprise ingredients commonly added for preparation of cosmetics.

The features and advantages of the present disclosure may be summarized as follows:

(a) The novel vascular leakage inhibitor of the present disclosure inhibits the apoptosis of vascular endothelial cells, inhibits the formation of actin stress fibers induced by VEGF, and enhances the cortical actin ring structure, thereby inhibiting vascular leakage.

(b) The vascular leakage inhibitor of the present disclosure can prevent or treat various diseases caused by vascular leakage.

(c) Since the vascular leakage inhibitor of the present disclosure is synthesized from commercially available or easily synthesizable pregnenolones, it has remarkably superior feasibility of commercial synthesis.

The present invention will now be described in further detail by examples. It would be obvious to those skilled in the at that these examples are intended to be more concretely illustrative and the scope of the present invention as set forth in the appended claims is not limited to or by the examples.

EXAMPLES

Compounds with various pseudosugar bioisosteres introduced at the 3-0H group of cholesterol were designed and synthesized.

Synthetic Example 1

Oxime Derivative Synthesis 1

Compounds were designed and synthesized, in which alkyl, cycloalkyl, cycloalkenyl, pyridinyl, and benzyl or phenyl having various substituents introduced thereinto are oxime-linked to the chain of compounds having tri-O-acetyl-D-glucan groups, which are cyclic ether groups exerting an important influence on biological activity, as bioesters at an alcohol site thereof.

Reaction Mechanism 1

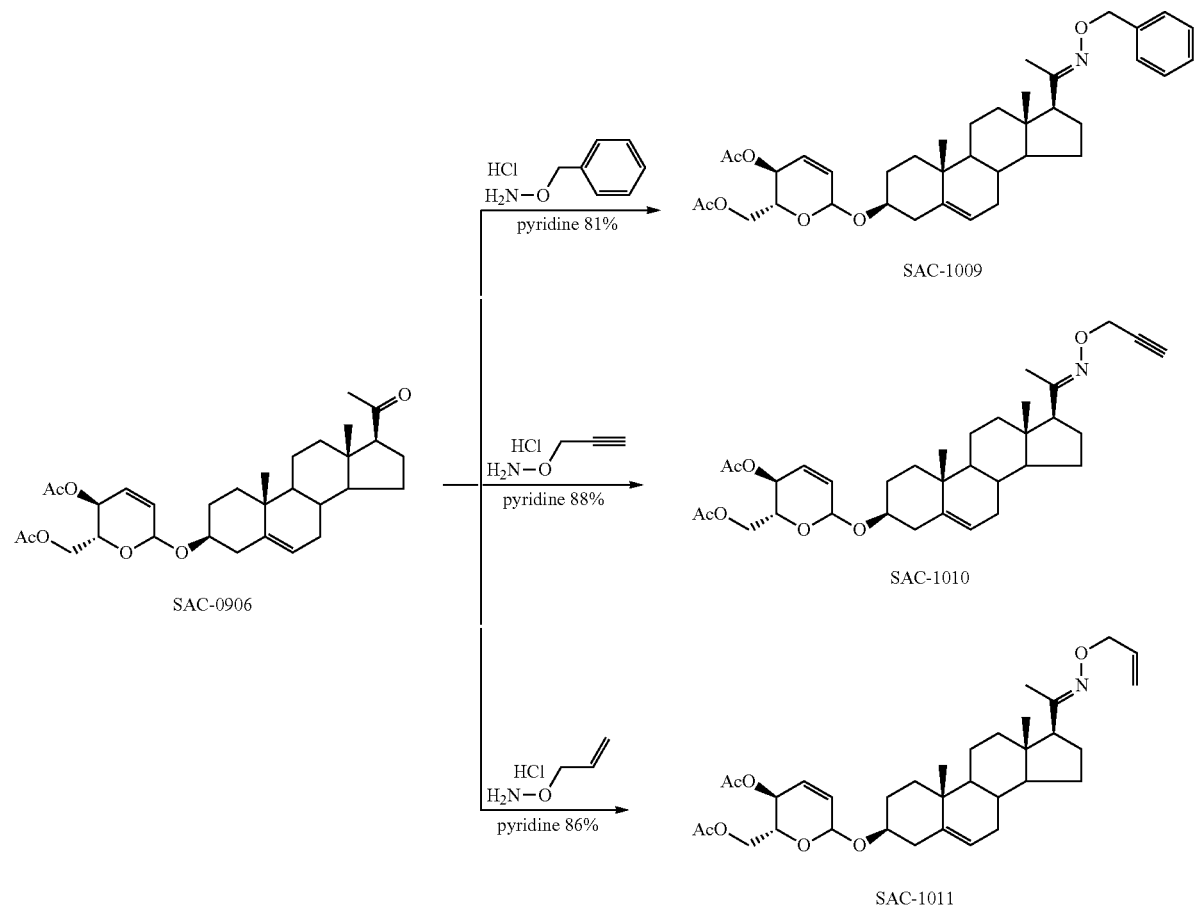

Synthetic Example 1-1

Preparation of SAC-1009

After 500 mg of pregnenolone (TCI) was dissolved in 13 ml of tetrahydrofurane under argon flow, 215 mg of tri-O-acetyl-D-glucan (Aldrich) and 0.2 ml of borontrifluoride diethyl etherate (Aldrich) were added at 0° C., followed by stirring at room temperature for 6 hours. The reaction liquid was diluted by adding 50 ml of diethyl ether and washed with an aqueous sodium hydrogen carbonate solution, followed by drying over magnesium sulfate and filtering. The filtrate was concentrated under reduced pressure, and the residue was subjected to silica gel column chromatography using ethyl acetate/hexane (1:10) as an eluent to obtain SAC-0906 (250 mg, yield: 60%). After 500 mg of hydroxyphthalimide (Aldrich) was dissolved in 5 ml of dimethylformamide under argon flow, 0.4 ml of benzyl bromide (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtering. The filtrate was concentrated under reduced pressure, and the residue was subjected to silica gel column chromatography using a mixed eluent of ethyl acetate/hexane (1:5) and then dried to obtain 338 mg of a white solid (yield: 50%). The white solid was dissolved in 5 ml of dichloromethane, and 0.11 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 171 mg of a solid (yield: 70%). 21 mg of the obtained solid and 59 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtering. The filtrate was concentrated under reduced pressure, and the residue was subjected to silica gel column chromatography using a mixed eluent of ethyl acetate/hexane (1:5) to obtain the target compound SAC-1009 (57 mg, yield: 81%). $^1$H-NMR (300 MHz, CDCl$_3$) δ7.30~7.17 (m, 5H), 5.88-5.72 (m, 2H), 5.30-5.28 (m, 1H), 5.24-5.21 (m, 1H), 5.10 (m, 1H), 5.01 (s, 2H), 4.24-4.01 (m, 3H), 3.59-3.44 (m, 1H), 2.38-0.51 (m, 35H).

Synthetic Example 1-2

Preparation of SAC-1010

After 500 mg of hydroxyphthalimide (Aldrich) was dissolved in 5 ml of dimethylformamide under argon flow, 501 mg of propargyl bromide (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtering. The filtrate was concentrated under reduced pressure, and the residue was subjected to silica gel column chromatography using a mixed eluent of ethyl acetate/hexane (1:5) and then dried to obtain 396 mg of a white solid (yield: 64%). The white solid was dissolved in 5 ml of dichloromethane, and 0.17 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 230 mg of a solid (yield: 100%). 13 mg of the obtained solid and 55 mg of SAC-0906 obtained as obtained above were dissolved in 1 ml of pyridine (Aldrich) under argon flow, followed by stirring at 80° C. for 2 hours. After the temperature was lowered to room temperature, the reaction liquid was acidified by adding a 2 N hydrochloric acid solution, followed by extraction with 20 ml of diethyl ether, drying over magnesium sulfate, and filtering. The filtrate was concentrated under reduced pressure, and the residue was subjected to silica gel column chromatography using a mixed eluent of ethyl acetate/hexane (1:5) to obtain the target compound SAC-1010 (53 mg, yield: 88%). $^1$H-NMR (300 MHz, CDCl$_3$) δ5.92-5.76 (m, 2H), 5.34-5.33 (m, 1H), 5.28-5.25 (m, 1H), 5.15 (m, 1H), 4.61 (d, J=2.4 Hz, 2H), 4.25-4.05 (m, 3H), 3.68-3.41 (m, 1H), 2.42-0.62 (m, 36H).

Synthetic Example 1-3

Preparation of SAC-1011

After 500 mg of hydroxyphthalimide (Aldrich) was dissolved in 5 ml of dimethylformamide under argon flow, 0.3 ml of allyl iodide (Aldrich) was added, and 0.5 ml of 1,8-diazabicyclo[5.4.0]undec-7-ene (Aldrich) was slowly added. After the mixture was stirred at room temperature for 1 hour and 20 minutes, the reaction was stopped by adding a 2 N hydrochloric acid solution. The reaction liquid was diluted by adding 20 ml of ethyl acetate, followed by drying over magnesium sulfate and then filtering. The filtrate was concentrated under reduced pressure, and the residue was subjected to silica gel column chromatography using a mixture eluent of ethyl acetate/hexane (1:5) and then dried to obtain 498 mg of a compound (yield: 80%). The compound was dissolved in 5 ml of dichloromethane, and 0.11 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 236 mg of a solid (yield: 88%). 16 mg of the obtained solid and 66 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtering. The filtrate was concentrated under reduced pressure, and the residue was subjected to silica gel column chromatography using a mixed eluent of ethyl acetate/hexane (1:5) to obtain the target compound SAC-1011 (63 mg, yield: 86%). $^1$H-NMR (300 MHz, CDCl$_3$) δ6.02-5.89 (m, 1H), 5.86-5.76 (m, 2H), 5.34-5.32 (m, 1H), 5.28-5.19 (m, 2H), 5.15-5.11 (m, 2H), 4.52-4.50 (m, 2H), 4.24-4.12 (m, 3H), 3.58-3.48 (m, 1H), 2.42-0.60 (m, 35H).

Reaction Mechanism 2

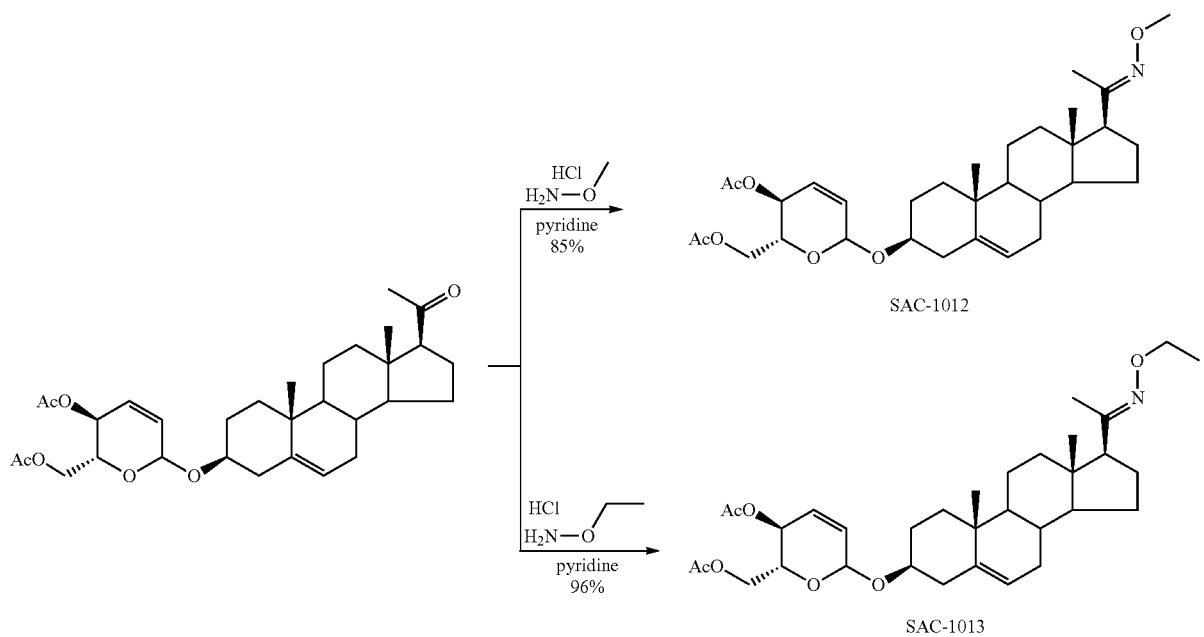

Synthetic Example 1-4

Preparation of SAC-1012

After 500 mg of hydroxyphthalimide (Aldrich) was dissolved in 5 ml of dimethylformamide under argon flow, 0.2 ml of iodinated methane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and filtration. The filtrate was concentrated under reduced pressure, and the residue was subjected to silica gel column chromatography using a mixture eluent of ethyl acetate/hexane (1:5) and then dried to obtain 407 mg of a compound (yield: 75%). The compound was dissolved in 5 ml of dichloromethane, and 0.11 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M hydrochloric acid dioxane solution (Aldrich) was added to the residual filtrate, followed by filtration and drying, to obtain 173 mg of a solid (yield: 90%). 10 mg of the obtained solid and 54 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1012 (48 mg, yield: 85%). $^1$H-NMR (300 MHz, CDCl$_3$) δ5.91-5.76 (m, 2H), 5.34-5.32 (m, 1H), 5.28-5.24 (m, 1H), 5.15 (m, 1H), 4.24-4.07 (m, 3H), 3.80 (s, 3H), 3.58-3.48 (m, 1H), 2.42-0.60 (m, 35H).

Synthetic Example 1-5

Preparation of SAC-1013

After 500 mg of hydroxyphthalimide (Aldrich) was dissolved in 5 ml of dimethylformamide under argon flow, 0.27 ml of iodinated ethane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixture eluent of ethyl acetate/hexane (1:5) and then dried to obtain 518 mg of a compound (yield: 88%). The compound was dissolved in 5 ml of dichloromethane, and 0.11 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 263 mg of a solid (yield: 100%). 10 mg of the obtained solid and 44 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1013 (46 mg, yield: 96%). $^1$H-NMR (300 MHz, CDCl$_3$) δ5.91-5.76 (m, 2H), 5.34-5.32 (m, 1H), 5.28-5.25 (m, 1H), 5.14 (m, 1H), 4.24-4.10 (m, 3H), 4.04 (q, J=20.9 Hz, 2H), 3.64-3.48 (m, 1H), 2.42-0.60 (m, 38H).

Reaction Mechanism 3

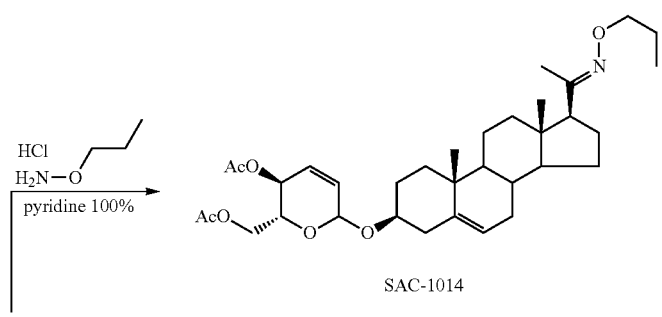

SAC-1014

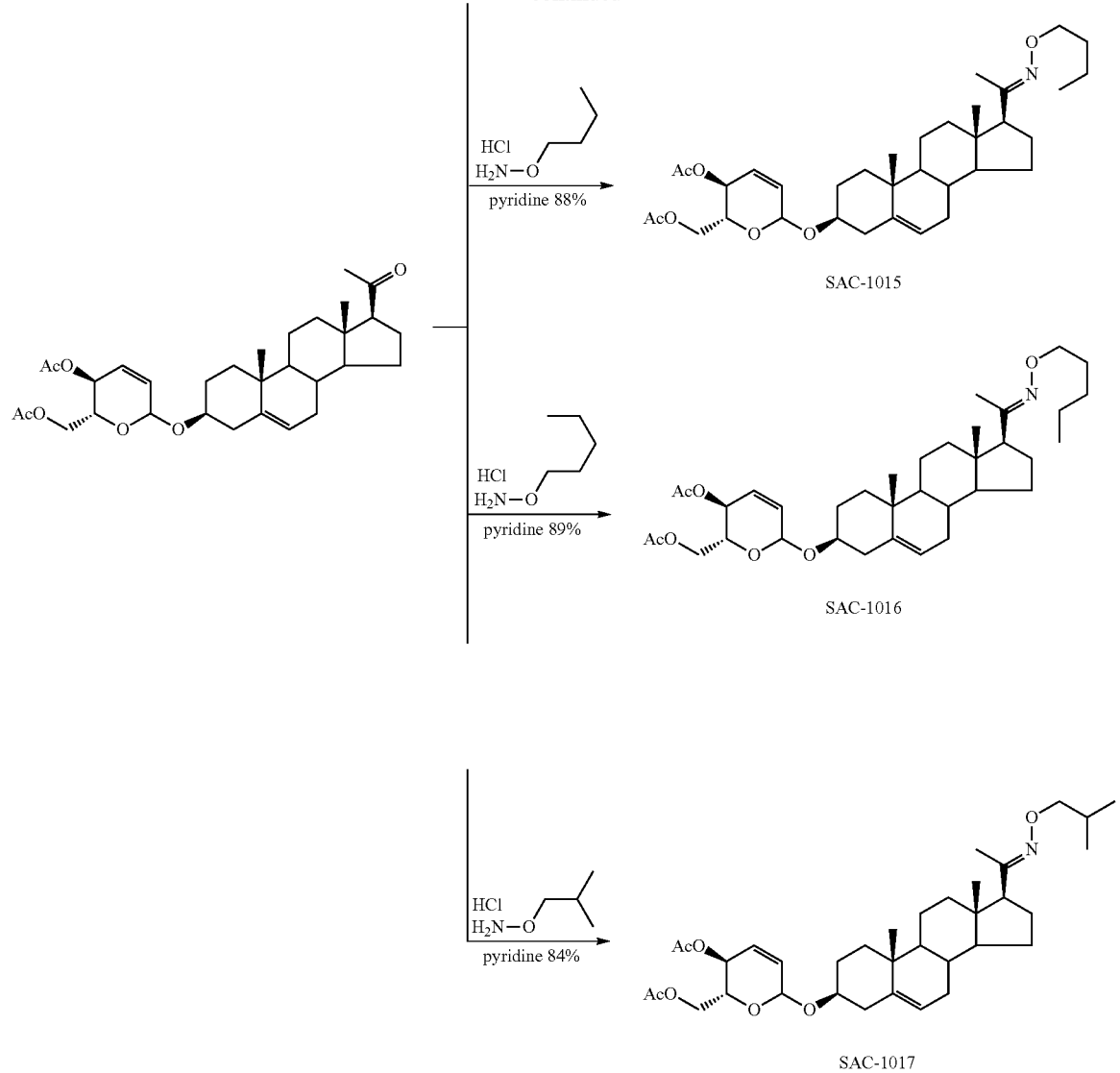

Synthetic Example 1-6

Preparation of SAC-1014

After 500 mg of hydroxyphthalimide (Aldrich) was dissolved in 5 ml of dimethylformamide under argon flow, 0.33 ml of iodinated propane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 459 mg of a compound (yield: 73%). The compound was dissolved in 5 ml of dichloromethane, and 0.11 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 125 mg of a solid (yield: 51%). 12 mg of the obtained solid and 48 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1014 (54 mg, yield: 100%). $^1$H-NMR (300 MHz, CDCl$_3$) δ5.91-5.76 (m, 2H), 5.34-5.32 (m, 1H), 5.28-5.25 (m, 1H), 5.15 (m, 1H), 4.25-4.10 (m, 3H), 3.99-3.88 (m, 2H), 3.59-3.48 (m, 1H), 2.42-0.60 (m, 40H).

Synthetic Example 1-7

Preparation of SAC-1015

After 500 mg of hydroxyphthalimide (Aldrich) was dissolved in 5 ml of dimethylformamide under argon flow, 0.38 ml of 1-iodinated butane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 635 mg of a compound (yield: 95%). The compound was dissolved in 5 ml of dichloromethane, and 0.12 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 257 mg of a solid (yield: 100%). 13 mg of the obtained solid and 44 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1015 (44 mg, yield: 88%). $^1$H-NMR (300 MHz, CDCl$_3$) δ5.91-5.76 (m, 2H), 5.34-5.33 (m, 1H), 5.28-5.25 (m, 1H), 5.15 (m, 1H), 4.25-4.10 (m, 3H), 4.02-3.97 (m, 2H), 3.59-3.48 (m, 1H), 2.42-0.60 (m, 42H).

Synthetic Example 1-8

Preparation of SAC-1016

After 500 mg of hydroxyphthalimide (Aldrich) was dissolved in 5 ml of dimethylformamide under argon flow, 0.44 ml of 1-iodinated pentane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 707 mg of a compound (yield: 99%). The compound was dissolved in 5 ml of dichloromethane, and 0.15 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 414 mg of a solid (yield: 98%). 16 mg of the obtained solid and 51 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1016 (53 mg, yield: 89%). $^1$H-NMR (300 MHz, CDCl$_3$) δ5.91-5.76 (m, 2H), 5.34-5.32 (m, 1H), 5.27-5.24 (m, 1H), 5.14 (m, 1H), 4.24-4.10 (m, 3H), 4.00-3.96 (m, 2H), 3.61-3.49 (m, 1H), 2.41-0.60 (m, 44H).

Synthetic Example 1-9

Preparation of SAC-1017

After 500 mg of hydroxyphthalimide (Aldrich) was dissolved in 5 ml of dimethylformamide under argon flow, 0.39 ml of 1-iodo-2-methyl propane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 529 mg of a compound (yield: 79%). The compound was dissolved in 5 ml of dichloromethane, and 0.1 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 303 mg of a solid (yield: 99%). 12 mg of the obtained solid and 43 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1017 (40 mg, yield: 84%). $^1$H-NMR (300 MHz, CDCl$_3$) δ5.91-5.76 (m, 2H), 5.34-5.33 (m, 1H), 5.28-5.25 (m, 1H), 5.15 (m, 1H), 4.25-4.10 (m, 3H), 3.85-3.71 (m, 2H), 3.59-3.48 (m, 1H), 2.42-0.60 (m, 42H).

Reaction Mechanism 4
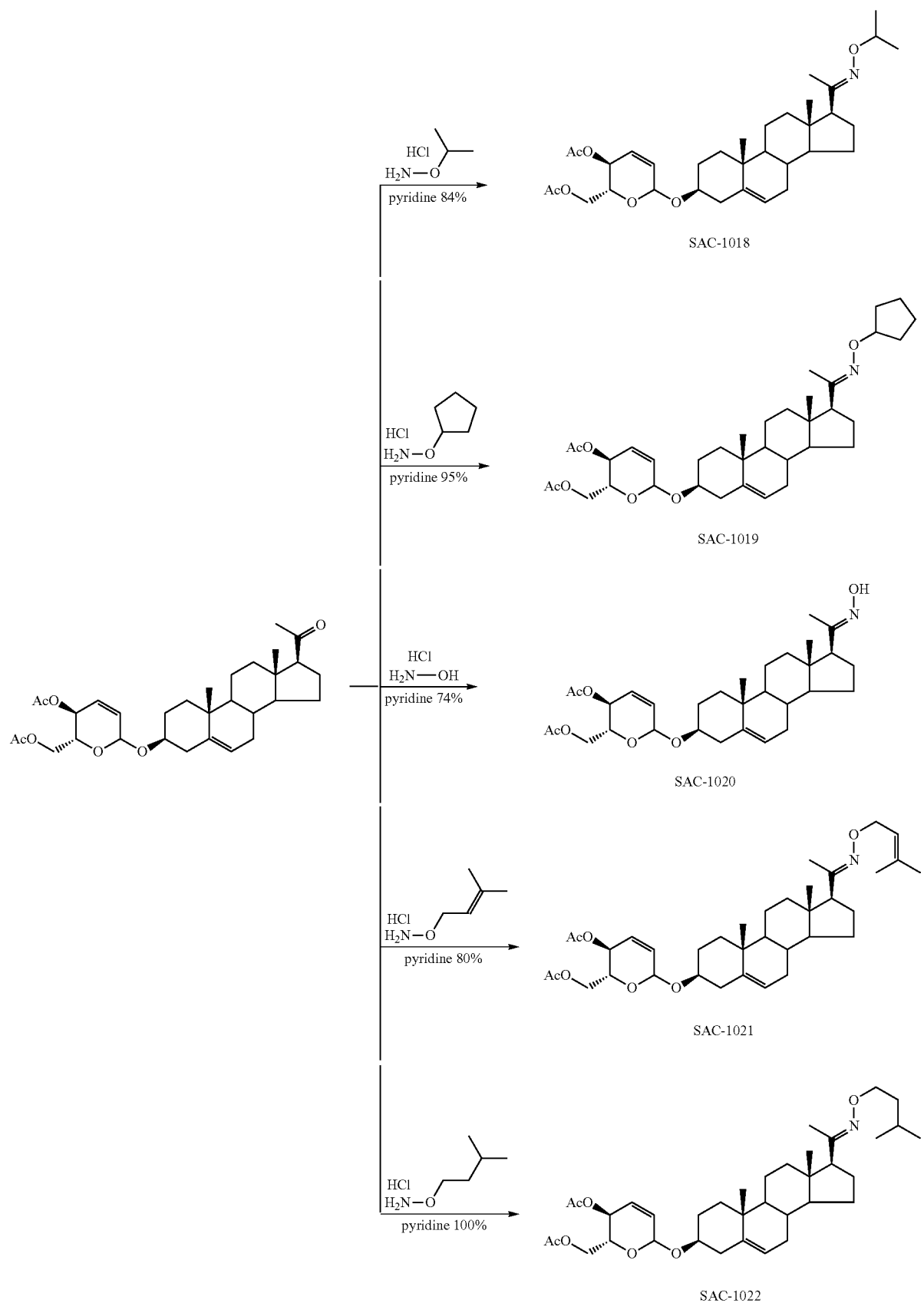

Synthetic Example 1-10

Preparation of SAC-1018

After 500 mg of hydroxyphthalimide (Aldrich) was dissolved in 5 ml of dimethylformamide under argon flow, 0.33 ml of isopropyl iodide (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 578 mg of a compound (yield: 92%). The compound was dissolved in 5 ml of dichloromethane, and 0.12 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 19 mg of a solid (yield: 6%). 9 mg of the obtained solid and 34 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1018 (32 mg, yield: 84%). $^1$H-NMR (300 MHz, CDCl$_3$) δ5.91-5.77 (m, 2H), 5.35-5.33 (m, 1H), 5.29-5.25 (m, 1H), 5.15 (m, 1H), 4.31-4.10 (m, 4H), 3.60-3.49 (m, 1H), 2.42-0.61 (m, 41H).

Synthetic Example 1-11

Preparation of SAC-1019

After 500 mg of hydroxyphthalimide (Aldrich) was dissolved in 5 ml of dimethylformamide under argon flow, 0.39 ml of cyclopentyl iodide (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 708 mg of a compound (yield: 100%). The compound was dissolved in 5 ml of dichloromethane, and 0.15 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 420 mg of a solid (yield: 99%). 11 mg of the obtained solid and 37 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1019 (40 mg, yield: 95%). $^1$H-NMR (300 MHz, CDCl$_3$) δ5.91-5.76 (m, 2H), 5.34-5.33 (m, 1H), 5.28-5.25 (m, 1H), 5.15 (m, 1H), 4.64-4.58 (m, 1H), 4.24-4.10 (m, 3H), 3.61-3.48 (m, 1H), 2.42-0.60 (m, 43H).

Synthetic Example 1-12

Preparation of SAC-1020

After 500 mg of hydroxyphthalimide (Aldrich) was dissolved in 5 ml of dimethylformamide under argon flow, 0.1 ml of methyl hydrazine (Aldrich) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 127 mg of a solid (yield: 60%). 7 mg of the obtained solid and 43 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1020 (43 mg, yield: 74%). $^1$H-NMR (300 MHz, CDCl$_3$) δ5.91-5.76 (m, 2H), 5.34-5.32 (m, 1H), 5.28-5.25 (m, 1H), 5.15 (m, 1H), 4.24-4.10 (m, 3H), 3.59-3.48 (m, 1H), 2.42-0.61 (m, 36H).

Synthetic Example 1-13

Preparation of SAC-1021

After 500 mg of hydroxyphthalimide (Aldrich) was dissolved in 5 ml of dimethylformamide under argon flow, 0.4 ml of 3,3-dimethyl allyl bromide (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 615 mg of a compound (yield: 87%). The compound was dissolved in 5 ml of dichloromethane, and 0.13 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 354 mg of a solid (yield: 97%). 17 mg of the obtained solid and 53 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1021 (49 mg, yield: 80%). $^1$H-NMR (300 MHz, CDCl$_3$) δ5.91-5.76 (m, 2H), 5.40-5.32 (m, 2H), 5.28-5.25 (m, 1H), 5.14 (m, 1H), 4.50 (d, J=7.0 Hz, 2H), 4.24-4.10 (m, 3H), 3.59-3.48 (m, 1H), 2.42-0.60 (m, 41H).

Synthetic Example 1-14

Preparation of SAC-1022

After 500 mg of hydroxyphthalimide (Aldrich) was dissolved in 5 ml of dimethylformamide under argon flow, 0.42 ml of 1-iodo-3-methyl butane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 692 mg of a compound (yield: 94%). The compound was dissolved in 5 ml of dichloromethane, and 0.14 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 363 mg of a solid (yield: 90%). 13 mg of the obtained solid and 41 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1022 (48 mg, yield: 100%). $^1$H-NMR (300 MHz, CDCl$_3$) δ5.91-5.76 (m, 2H), 5.34-5.32 (m, 1H), 5.28-5.25 (m, 1H), 5.14 (m, 1H), 4.28-4.12 (m, 3H), 4.02 (t, J=13.5 Hz, 2H), 3.59-3.48 (m, 1H), 2.42-0.60 (m, 44H).

Synthetic Example 2

Oxime Derivative Synthesis 2

Reaction Mechanism 5

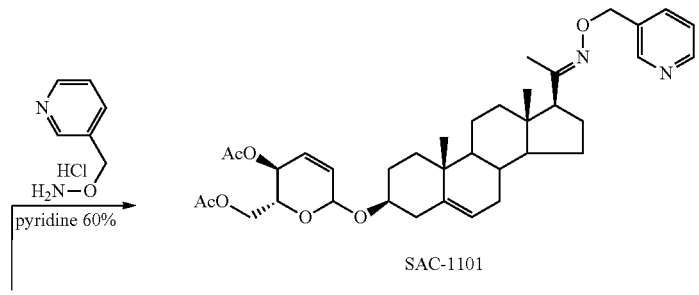

SAC-1101

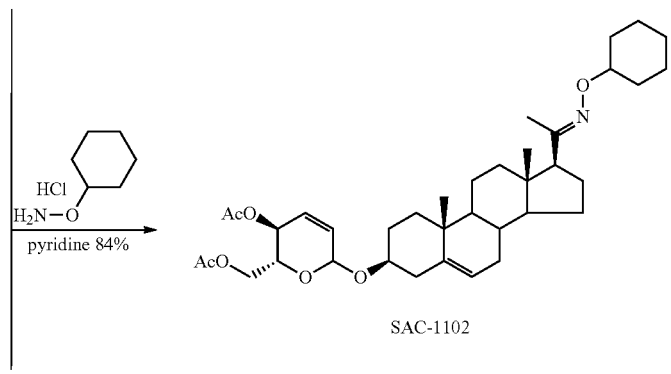

SAC-1102

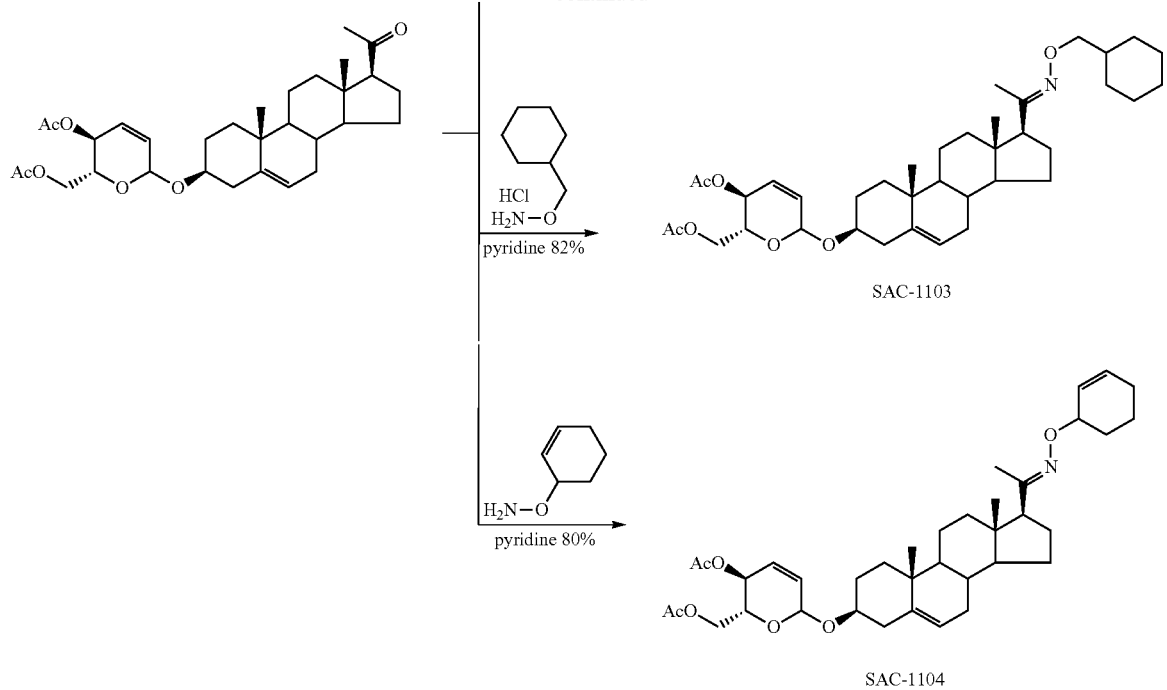

Synthetic Example 2-1

Preparation of SAC-1101

After 341 mg of hydroxyphthalimide (Aldrich), 0.2 ml of 3-pyrimidinemethanol (Aldrich), and 548 mg of triphenylphosphine (Aldrich) were dissolved in 7 ml of chloroform under argon flow, 0.5 ml of diisopropyl azodicarboxylate (Aldrich) was slowly added at 0° C. The mixture was stirred at room temperature for 1 hour, and the solvent was concentrated under reduced pressure. The reaction liquid was diluted by 20 ml of ethyl acetate, and extraction was conducted by adding a 2 N hydrochloric acid solution. The aqueous layer was collected, and neutralized with sodium carbonate, followed by drying over magnesium sulfate and then filtration. After the filtrate was concentrated under reduced pressure, the residue was subjected to silica gel column chromatography using a mixed eluent of benzene/ethyl acetate (1:1) to obtain 300 mg of a compound (yield: 56%) (*Organic Preparations and Procedures int.*, 26(1):111-127(1994)). The compound was dried, and then dissolved in 3 ml of ethanol, and 0.12 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 103 mg of a white solid (yield: 54%). The obtained white solid and 59 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1101 (195 mg, yield: 60%). $^1$H-NMR (300 MHz, CDCl$_3$) δ8.61 (s, 1H), 8.54 (d, J=4.4 Hz, 1H), 7.74 (d, J=7.7 Hz, 1H), 7.32 (dd, J=12.6 Hz, 1H), 5.90-5.80 (m, 2H), 5.36 (m, 1H), 5.31-5.28 (m, 1H), 5.18 (m, 1H), 5.10 (s, 2H), 4.27-4.10 (m, 3H), 3.59-3.52 (m, 1H), 2.40-0.54 (m, 35H).

Synthetic Example 2-2

Preparation of SAC-1102

After 500 mg of hydroxyphthalimide (Aldrich) was dissolved in 5 ml of dimethylformamide under argon flow, 0.43 ml of 3-bromocyclohexene (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 745 mg of a compound (yield: 100%). 120 mg of the compound was dissolved in 3 ml of methanol and 0.5 ml of ethyl acetate, and 10 mg of palladium 10%-carbon (Aldrich) was added. The reaction liquid was stirred for 2 hours while a hydrogen gas was injected thereinto, and then subjected to silica gel column chromatography. The generated solid was filtered out, and the residual filtrate was dried to obtain 95 mg of a solid (yield: 78%). 92 mg of the obtained solid was dissolved in 5 ml of dichloromethane, and 0.036 ml of hydrazine hydrate (Aldrich) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 30 mg of a solid (yield: 53%). 19 mg of the obtained solid and 50 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1102 (58 mg, yield: 98%). $^1$H-NMR (400 MHz, CDCl$_3$) δ 5.89-5.79 (m, 2H), 5.34 (m, 1H), 5.29-5.26 (m, 1H), 5.15 (m, 1H), 4.24-4.15 (m, 3H), 4.02-3.97 (m, 1H), 3.57-3.52 (m, 1H), 2.41-0.61 (m, 45H).

Synthetic Example 2-3

Preparation of SAC-1103

After 500 mg of hydroxyphthalimide (Aldrich) was dissolved in 5 ml of dimethylformamide under argon flow, 0.47 ml of (bromomethyl)cyclohexane (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 787 mg of a compound (yield: 99%). 400 mg of the obtained compound was dissolved in 5 ml of dichloromethane, and 0.14 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 240 mg of a solid (yield: 94%). 21 mg of the obtained solid and 50 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtering. The filtrate was concentrated under reduced pressure, and the residue was subjected to silica gel column chromatography using a mixed eluent of ethyl acetate/hexane (1:5) to obtain the target compound SAC-1103 (50 mg, yield: 82%). $^1$H-NMR (400 MHz, CDCl$_3$) δ 5.87-5.78 (m, 2H), 5.35-5.34 (m, 1H), 5.29-5.26 (m, 1H), 5.16 (m, 1H), 4.24-4.14 (m, 3H), 3.86-3.76 (m, 2H), 3.58-3.51 (m, 1H), 2.41-0.61 (m, 46H).

Synthetic Example 2-4

Preparation of SAC-1104

After 500 mg of hydroxyphthalimide (Aldrich) was dissolved in 5 ml of dimethylformamide under argon flow, 0.43 ml of 3-bromocyclohexene (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 745 mg of a compound (yield: 100%). 95 mg of the obtained compound was dissolved in 4 ml of dichloromethane, and 0.12 ml of hydrazine hydrate (Aldrich) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 151 mg of a solid (yield: 83%). 19 mg of the obtained solid and 50 mg of SAC-0906 obtained as obtained above were dissolved in 1 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtering. The filtrate was concentrated under reduced pressure, and the residue was subjected to silica gel column chromatography using a mixed eluent of ethyl acetate/hexane (1:5) to obtain the target compound SAC-1104 (59 mg, yield: 100%). $^1$H-NMR (400 MHz, CDCl$_3$) δ 5.90-5.79 (m, 4H), 5.35-5.34 (m, 1H), 5.29-5.26 (m, 1H), 5.15 (m, 1H), 4.56 (m, 1H), 4.24-4.11 (m, 3H), 3.58-3.50 (m, 1H), 2.42-0.62 (m, 41H).

Reaction Mechanism 6

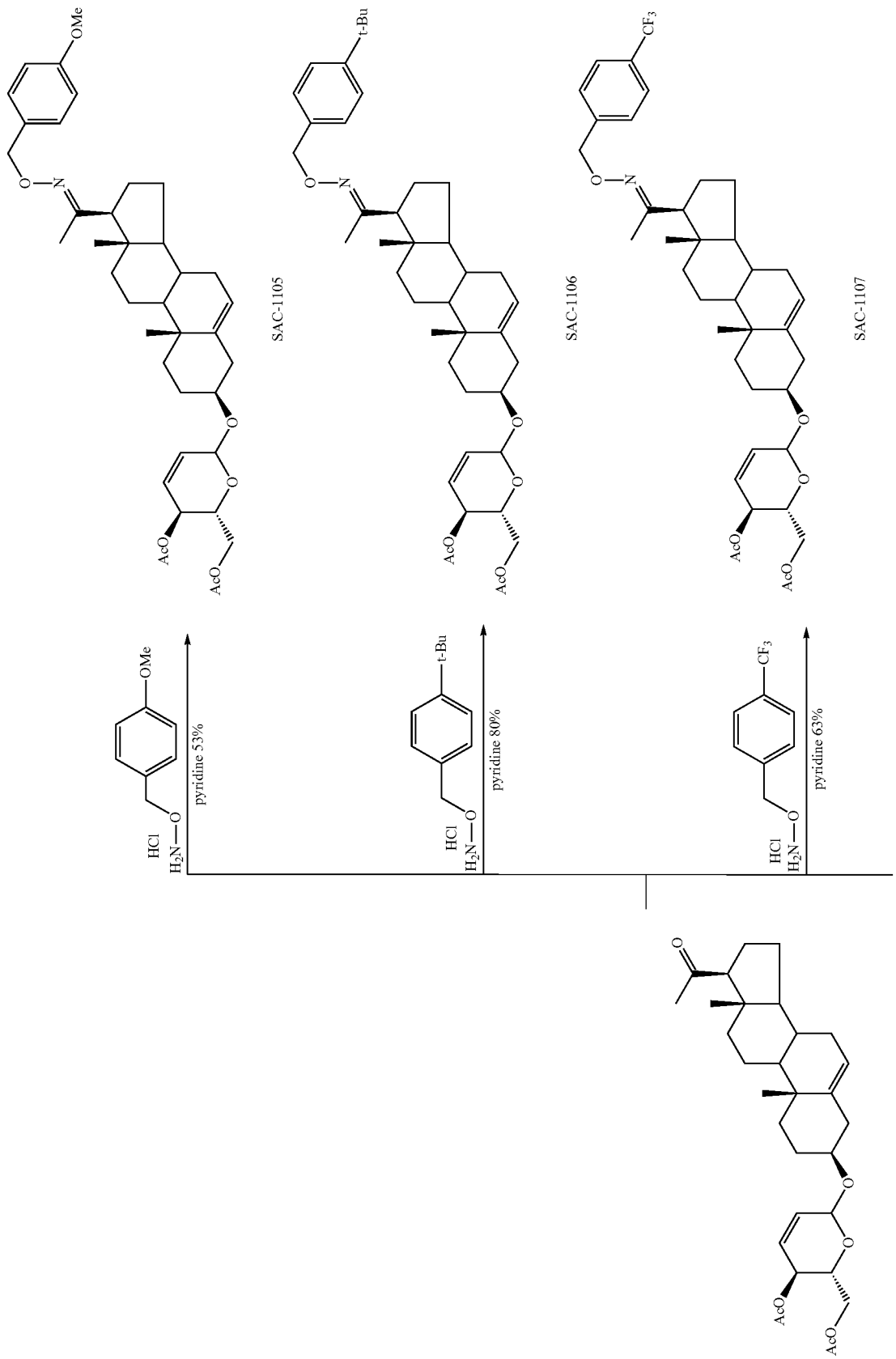

-continued
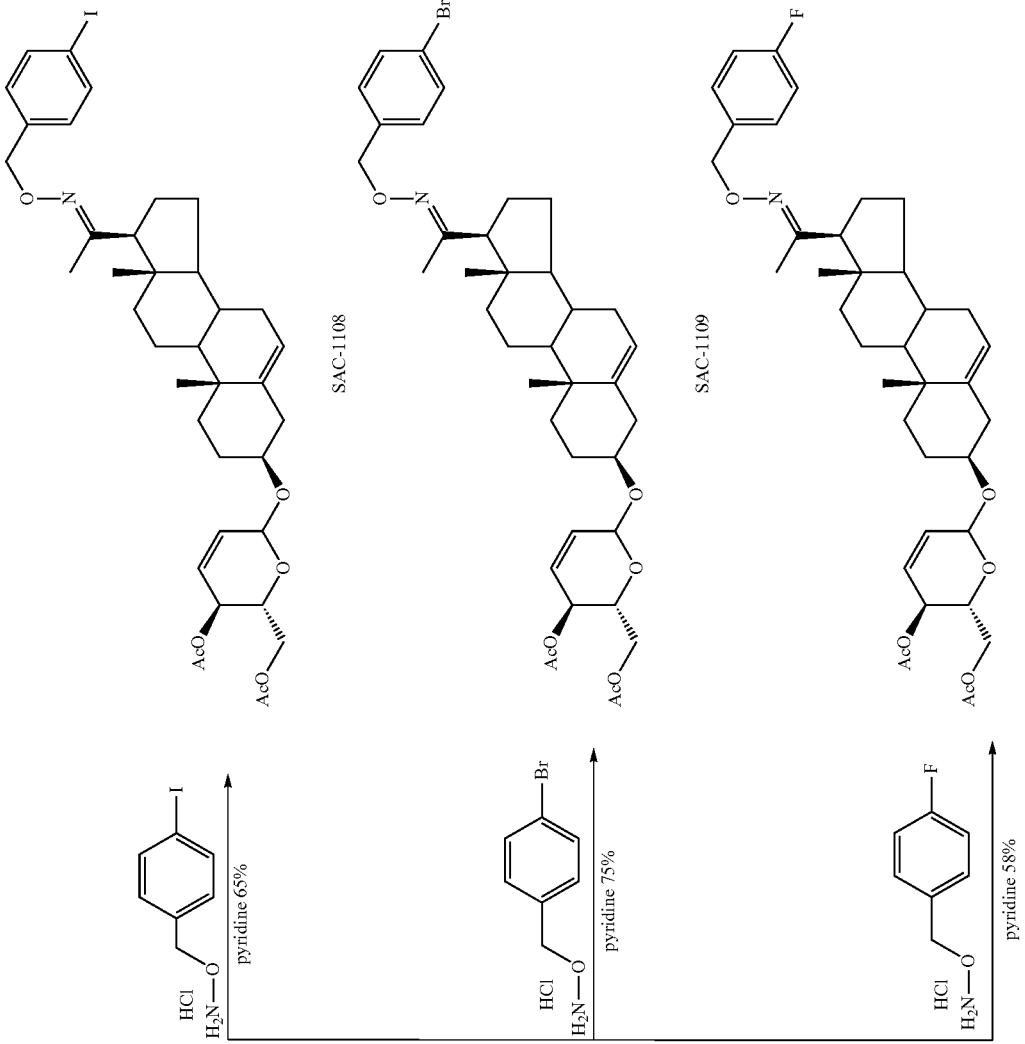

Synthetic Example 2-5

Preparation of SAC-1105

After 489 mg of hydroxyphthalimide (Aldrich) was dissolved in 5 ml of dimethylformamide under argon flow, 0.45 ml of 4-methoxybenzyl chloride (Aldrich) was added, and 0.5 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding an aqueous 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5). The compound was dried, and then dissolved in 5 ml of dichloromethane, and 0.5 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 550 mg of a solid (yield: 31%). 55 mg of the obtained solid and 151 mg of SAC-0906 obtained as obtained above were dissolved in 3 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1105 (101 mg, yield: 53%). $^1$H-NMR (300 MHz, CDCl$_3$) δ7.28 (d, J=8.4 Hz, 2H), 6.86-6.83 (d, J=8.6 Hz, 2H), 5.88-5.78 (m, 2H), 5.35 (m, 1H), 5.29-5.26 (m, 1H), 5.16 (m, 1H), 4.99 (s, 2H), 4.24-4.11 (m, 3H), 3.78 (s, 3H), 3.54 (m, 1H), 2.36-0.57 (m, 35H).

Synthetic Example 2-6

Preparation of SAC-1106

After 326 mg of hydroxyphthalimide (Aldrich) was dissolved in 5 ml of dimethylformamide under argon flow, 0.4 ml of 4-(t-butyl)benzyl bromide (Aldrich) was added, and 0.33 ml of 1,8-diazabicyclo[5.4.0]undec-7-ene (Aldrich) was slowly added. After the mixture was stirred at 60° C. for 2 hours, the temperature was again lowered to room temperature, and then the reaction was stopped by adding a 2 N hydrochloric acid solution. The reaction liquid was diluted by adding 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) and then dried to obtain 854 mg of a compound (yield: 62%). The compound was dissolved in 8 ml of dichloromethane, and 0.2 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 536 mg of a solid (yield: 90%). 49 mg of the obtained solid and 100 mg of SAC-0906 obtained as obtained above were dissolved in 3 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1106 (103 mg, yield: 79%). $^1$H-NMR (500 MHz, CDCl$_3$) δ7.34 (d, J=8.3 Hz, 2H), 7.28 (d, J=8.2 Hz, 2H), 5.87-5.78 (m, 2H), 5.35-5.34 (m, 1H), 5.29-5.25 (m, 1H), 5.16 (m, 1H), 5.04 (s, 2H), 4.24-4.14 (m, 3H), 3.58-3.51 (m, 1H), 2.41-0.57 (m, 44H).

Synthetic Example 2-7

Preparation of SAC-1107

After 463 mg of hydroxyphthalimide (Aldrich), 0.4 ml of 4-(trifluoromethyl)benzyl alcohol (Aldrich), and 745 mg of triphenylphosphine (Aldrich) were dissolved in 8 ml of tetrahydrofurane under argon flow, 0.67 ml of diisopropyl azodicarboxylate (Aldrich) was slowly added at 0° C. The mixture was stirred at room temperature for 1 hour, and the solvent was concentrated under reduced pressure. The reaction liquid was diluted by 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (1:5) to obtain a compound. The obtained compound was dried and then dissolved in 8 ml of dichloromethane, and 0.16 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 165 mg of a white solid (yield: 26%). 52 mg of the obtained white solid and 100 mg of SAC-0906 obtained as obtained above were dissolved in 3 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1107 (100 mg, yield: 63%). $^1$H-NMR (300 MHz, CDCl$_3$) δ7.58 (d, J=8.0 Hz, 2H), 7.44 (d, J=8.0 Hz, 2H), 5.89-5.79 (m, 2H), 5.36-5.34 (m, 1H), 5.30-5.27 (m, 1H), 5.17 (m, 1H), 5.12 (s, 2H), 4.27-4.13 (m, 3H), 3.59-3.52 (m, 1H), 2.40-0.56 (m, 35H).

Synthetic Example 2-8

Preparation of SAC-1108

After 348 mg of hydroxyphthalimide (Aldrich), 500 mg of 4-iodobenzyl alcohol (Aldrich), and 560 mg of triphenylphosphine (Aldrich) were dissolved in 7 ml of tetrahydrofurane under argon flow, 0.5 ml of diisopropyl azodicarboxylate (Aldrich) was slowly added at 0° C. The mixture was stirred at room temperature for 1 hour, and the solvent was concentrated under reduced pressure. The reaction liquid was diluted by 20 ml of ethyl acetate, and a 2 N hydrochloric acid solution was added to generate a solid, which was then removed. The filtrate was again concentrated under reduced pressure, and then dissolved in 10 ml of hexane and 10 ml of diethyl ether to again obtain a solid (700 mg, yield: 87%). This compound was dried, and then dissolved in 8 ml of dichloromethane, and 0.2 ml of methyl hydrazine (TCI) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 465 mg of a white solid (yield: 88%). 65 mg of the obtained white solid and 100 mg of SAC-0906 obtained as obtained above were dissolved in 3 ml of pyridine (Aldrich) under argon flow, followed by stirring at 80° C. for 4 hours. After the temperature was lowered to room temperature, the reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1108 (94 mg, yield: 65%). $^1$H-NMR (400 MHz, CDCl$_3$) δ7.63 (d, J=8.1 Hz, 2H), 7.43 (d, J=8.3 Hz, 2H), 5.87-5.78 (m, 2H), 5.35-5.33 (m, 1H), 5.29-5.26 (m, 1H), 5.15 (m, 1H), 4.99 (s, 2H), 4.24-4.13 (m, 3H), 3.58-3.50 (m, 1H), 2.42-0.56 (m, 35H).

Synthetic Example 2-9

Preparation of SAC-1109

After 595.4 mg of hydroxyphthalimide (Aldrich) was dissolved in 6 ml of dimethylformamide under argon flow, 1003.5 ml of 4-bromobenzyl bromide (Aldrich) was added, and 0.6 ml of 1,8-diazabicyclo[5.4.0]undec-7-ene (Aldrich) was slowly added. The mixture was stirred at 60° C. for 2 hours, and the temperature was lowered to room temperature. The reaction was stopped by adding a 2 N hydrochloric acid solution, followed by filtration with ethyl acetate. The solid was again dissolved in ethanol and then recrystallized, followed by filtration and drying, to obtain 932 mg of a white solid (yield: 77%). 500 mg of the obtained white solid was dissolved in 10 ml of dichloromethane, and 0.07 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 241 mg of a solid (yield: 67%). 27 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1109 (50 mg, yield: 75%). $^1$H-NMR (300 MHz, CDCl$_3$) δ7.44-7.40 (m, 2H), 7.21-7.18 (m, 2H), 5.88-5.77 (m, 2H), 5.35-5.33 (m, 1H), 5.29-5.26 (m, 1H), 5.16 (m, 1H), 5.00 (s, 2H), 4.24-4.13 (m, 3H), 3.58-3.49 (m, 1H), 2.41-0.55 (m, 35H).

Synthetic Example 2-10

Preparation of SAC-1110

After 595 mg of hydroxyphthalimide (Aldrich) was dissolved in 6 ml of dimethylformamide under argon flow, 0.5 ml of 4-fluorobenzyl bromide (Aldrich) was added, and 0.6 ml of 1,8-diazabicyclo[5.4.0]undec-7-ene (Aldrich) was slowly added. The mixture was stirred at room temperature for 1 hour, and the reaction was stopped by adding a 2 N hydrochloric acid solution, followed by filtration with ethyl acetate. The solid was again dissolved in ethanol and then recrystallized, followed by filtration and drying, to obtain 785 mg of a white solid (yield: 79%). 600 mg of the obtained white solid was dissolved in 10 ml of dichloromethane, and 0.1 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 392 mg of a solid (yield: 100%). 20 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1110 (36 mg, yield: 58%). $^1$H-NMR (400 MHz, CDCl$_3$) δ7.32-7.28 (m, 2H), 7.01-6.97 (m, 2H), 5.87-5.78 (m, 2H), 5.35-5.33 (m, 1H), 5.29-5.26 (m, 1H), 5.15 (m, 1H), 5.01 (s, 2H), 4.24-4.14 (m, 3H), 3.58-3.50 (m, 1H), 2.42-0.55 (m, 35H).

Reaction Mechanism 7

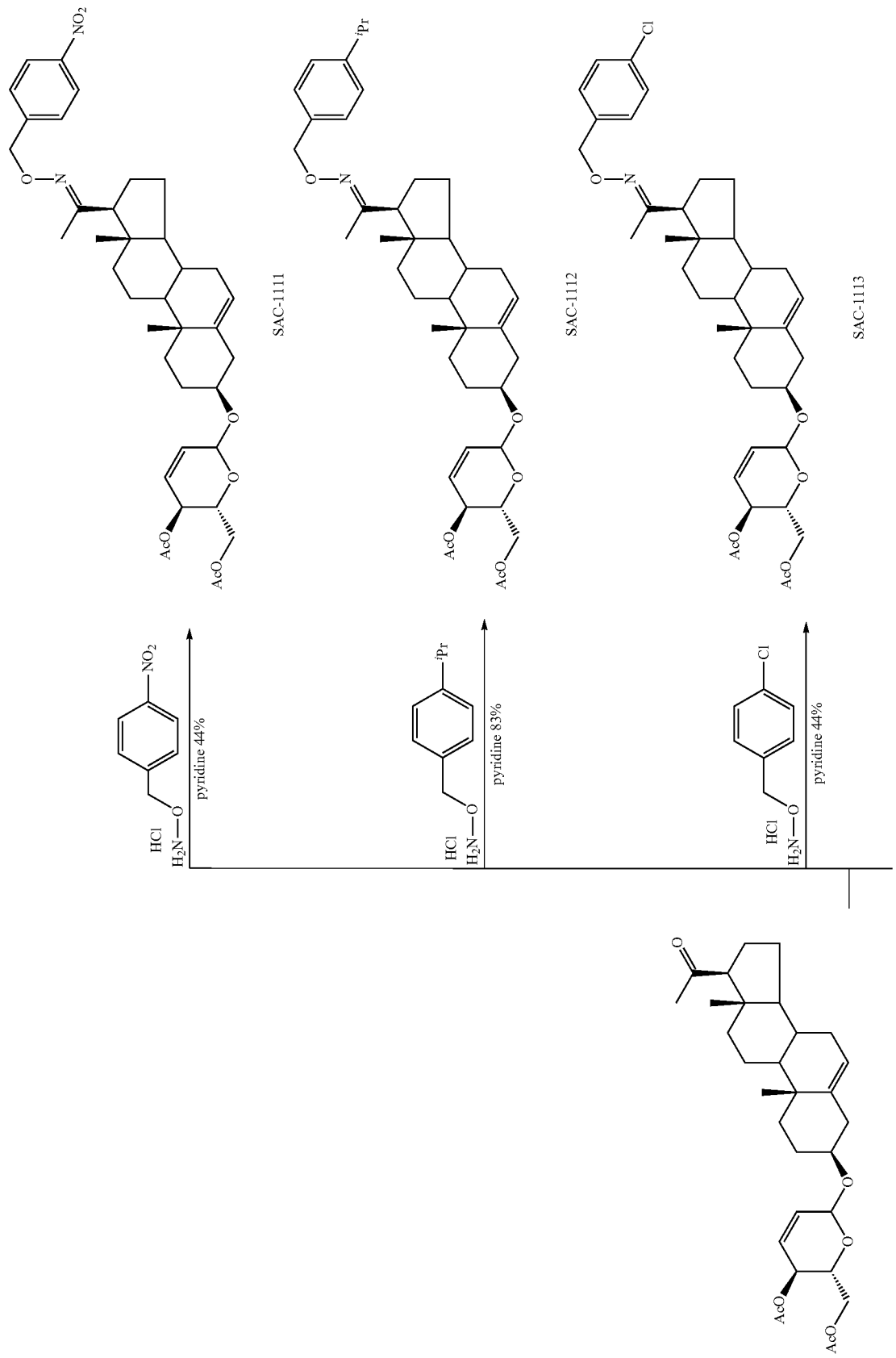

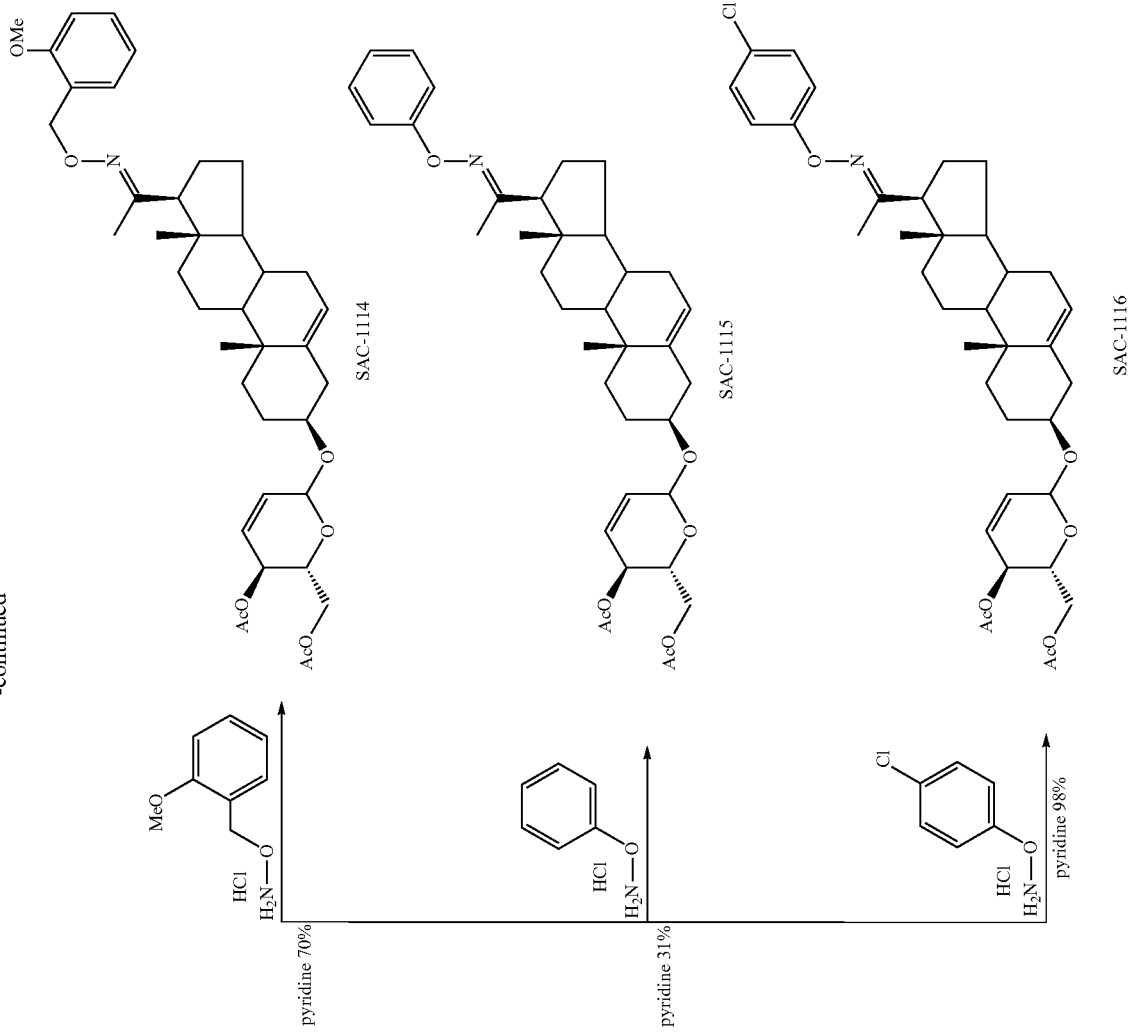

Synthetic Example 2-11

Preparation of SAC-1111

After 686 mg of hydroxyphthalimide (Aldrich) was dissolved in 10 ml of dimethylformamide under argon flow, 1 g of 4-nitrobenzyl chloride (Aldrich) was added, and 0.7 ml of 1,8-diazabicyclo[5.4.0]undec-7-ene (Aldrich) was slowly added. The mixture was stirred at room temperature for 1 hour, and the reaction was stopped by adding a 2 N hydrochloric acid solution, followed by filtration with ethyl acetate. The solid was again dissolved in ethanol and then recrystallized, followed by filtration and drying, to obtain 1.19 g of a white solid (yield: 87%). 500 mg of the obtained white solid was dissolved in 15 ml of acetonitrile, and 0.06 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 139 mg of a solid (yield: 41%). 23 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1111 (28 mg, yield: 44%). $^1$H-NMR (400 MHz, CDCl$_3$) δ8.17 (d, J=8.7 Hz, 2H), 7.46 (d, J=8.6 Hz, 2H), 5.90-5.78 (m, 2H), 5.34-5.33 (m, 1H), 5.29-5.26 (m, 1H), 5.15 (m, 3H), 4.24-4.13 (m, 3H), 3.58-3.50 (m, 1H), 2.41-0.54 (m, 35H).

Synthetic Example 2-12

Preparation of SAC-1112

After 500 mg of hydroxyphthalimide (Aldrich), 0.47 ml of 4-isopropylbenzyl alcohol (Aldrich), and 804 mg of triphenylphosphine (Aldrich) were dissolved in 12 ml of tetrahydrofurane under argon flow, 0.72 ml of diisopropyl azodicarboxylate (Aldrich) was slowly added at 0° C. The mixture was stirred at room temperature for 1 hour, and the solvent was concentrated under reduced pressure. The reaction liquid was diluted by 20 ml of ethyl acetate, followed by drying over magnesium sulfate and then filtration. The filtrate was concentrated under reduced pressure, and the residue was subjected to silica gel column chromatography using a mixed eluent of ethyl acetate/hexane (5:1) and then dried to obtain 855 mg of a compound (yield: 94%). 600 mg of the obtained compound was dissolved in 12 ml of dichloromethane, and 0.09 ml of hydrazine hydrate (Aldrich) was slowly added at 0° C. After the reaction liquid was stirred at room temperature for 2 hours, the temperature was again lowered to 0° C. The generated solid was then filtered out, and 1 ml of a 4 M-hydrochloric acid dioxane solution (Aldrich) was added to the residual filtrate, followed by filtration and drying, to obtain 346 mg of a white solid (yield: 85%). 23 mg of the obtained white solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1112 (53 mg, yield: 83%). $^1$H-NMR (400 MHz, CDCl3) δ7.27 (d, J=7.9 Hz, 2H), 7.17 (d, J=7.9 Hz, 2H), 5.87-5.79 (m, 2H), 5.35-5.34 (m, 1H), 5.29-5.26 (m, 1H), 5.16 (m, 1H), 5.03 (s, 2H), 4.24-4.14 (m, 3H), 3.58-3.51 (m, 1H), 2.93-2.83 (m, 1H), 2.42-0.57 (m, 41H).

Synthetic Example 2-13

Preparation of SAC-1113

500 mg of 4-chlorobenzyl aldehyde (Aldrich) was dissolved in 15 ml of methanol, and 161.5 mg of sodium borohydride (Aldrich) was slowly added at 0° C. The mixture was stirred at room temperature for 1 hour, and acidified with an aqueous ammonium chloride solution and an aqueous 1 N hydrochloric acid solution, followed by extraction with 20 ml of diethyl ether. The filtrate was concentrated under reduced pressure, and the residue was subjected to silica gel column chromatography using a mixed eluent of ethyl acetate/hexane (1:5) to obtain 442 mg of a compound (yield: 87%). After 435 mg of the obtained compound, 498 mg of hydroxyphthalimide (Aldrich), and 800 mg of triphenylphosphine (Aldrich) were dissolved in 12 ml of tetrahydrofurane under argon flow, 0.72 mg of diisopropyl azodicarboxylate (Aldrich) was slowly added at 0° C. The mixture was stirred at room temperature for 1 hour, and the solvent was concentrated under reduced pressure. The reaction liquid was diluted by 20 ml of ethyl acetate, followed by drying over magnesium sulfate and then filtration. The filtrate was concentrated under reduced pressure, and the residue was subjected to silica gel column chromatography using a mixed eluent of hexane/ethyl acetate (5:1) and then dried to obtain 490 mg of a solid (yield: 56%). 478 mg of the obtained solid was dissolved in 10.5 ml of dichloromethane, and 0.078 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 193 mg of a solid (yield: 60%). 22 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1113 (57 mg, yield: 90%). $^1$H-NMR (400 MHz, CDCl3) δ7.26-7.23 (m, 4H), 5.85-5.76 (m, 2H), 5.31 (m, 1H), 5.26-5.24 (m, 1H), 5.13 (m, 1H), 4.99 (s, 2H), 4.22-4.11 (m, 3H), 3.55-3.49 (m, 1H), 2.40-0.53 (m, 35H).

Synthetic Example 2-14

Preparation of SAC-1114

After 533 mg of hydroxyphthalimide (Aldrich) was dissolved in 6 ml of dimethylformamide under argon flow, 0.5 ml of 2-methoxybenzyl chloride (Aldrich) was added, and 0.54 ml of 1,8-diazabicyclo[5.4.0]undec-7-ene (Aldrich) was slowly added. The mixture was stirred at room temperature for 1 hour, and the reaction was stopped by adding a 2 N hydrochloric acid solution, followed by filtration with ethyl acetate. The solid was again dissolved in ethanol and then recrystallized, followed by filtration and drying, to obtain 926 mg of a white solid (yield: 100%). 500 mg of the obtained solid was dissolved in 10 ml of dichloromethane, and 0.082 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 166 mg of a solid (yield: 49%). 21 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1114 (44 mg, yield: 70%). $^1$H-NMR (400 MHz, CDCl3) δ7.32-7.20 (m, 2H), 6.92-6.82 (m, 2H), 5.86-5.78 (m, 2H), 5.34 (m, 1H), 5.28-5.26 (m, 1H), 5.15 (m, 1H), 5.13 (s, 2H), 4.24-4.13 (m, 3H), 3.80 (s, 3H), 3.57-3.51 (m, 1H), 2.42-0.58 (m, 35H).

Synthetic Example 2-15

Preparation of SAC-1115

After 163 mg of hydroxyphthalimide (Aldrich), 99 mg of copper chloride (Aldrich), 230 mg of molecular sieve 4 (Aldrich), and 244 mg of phenyl boronic acid (Aldrich) were sequentially dissolved in 5 ml of dichloroethane (Aldrich) under argon flow, 0.09 ml of pyridine (Aldrich) was added, followed by stirring for 5 hours. The reaction liquid was exposed to air, followed by stirring for 14 hours, and then the molecular sieve was filtered out, followed by dilution with ethyl acetate. The solution was concentrated under reduced pressure, and the residue was subjected to silica gel column chromatography using a mixed eluent of ethyl acetate/hexane (1:2) to obtain a compound (161 mg, yield: 67%). The compound was dissolved in 3 ml of dichloromethane, and 0.10 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 0.3 ml of a 4 M-hydrochloric acid dioxane solution (Aldrich) was added to the solution, followed by filtration and drying, to obtain 103 mg of a solid (yield: 99%). 21 mg of the obtained solid and 50 mg of SAC-0906 obtained as obtained above were dissolved in 1 ml of pyridine (Aldrich) under argon flow, followed by stirring at 70° C. for 1 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1115 (18 mg, yield: 31%). $^1$H-NMR (300 MHz, CDCl3) δ7.30-7.24 (m, 2H), 7.17-7.12 (m, 2H), 6.98-6.93 (m, 1H), 5.89-5.78 (m, 2H), 5.37-5.35 (m, 1H), 5.30-5.27 (m, 1H), 5.17 (m, 1H), 4.27-4.14 (m, 3H), 3.59-3.52 (m, 1H), 2.43-0.70 (m, 35H).

Synthetic Example 2-16

Preparation of SAC-1116

After 300 mg of hydroxyphthalimide (Aldrich), 182 mg of copper chloride (Aldrich), 750 mg of molecular sieve 4 (Aldrich), and 575 mg of 4-chlorophenyl boronic acid (Aldrich) were sequentially dissolved in 8 ml of dichloroethane (Aldrich) under argon flow, 0.17 ml of pyridine (Aldrich) was added, followed by stirring for 5 hours. The reaction liquid was exposed to air, followed by stirring for 14 hours, and then the molecular sieve was filtered out, followed by dilution with ethyl acetate. The solution was concentrated under reduced pressure, and the residue was subjected to silica gel column chromatography using a mixed eluent of ethyl acetate/hexane (1:2) to obtain a compound (246 mg, yield: 49%). 150 mg of the obtained compound was dissolved in 3 ml of dichloromethane, and 0.05 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 81 mg of a solid (yield: 78%). 20 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1116 (57 mg, yield: 98%). $^1$H-NMR (400 MHz, CDCl3) δ7.21 (d, J=8.6 Hz, 2H), 7.07 (d, J=8.6 Hz, 2H), 5.87-5.79 (m, 2H), 5.36-5.35 (m, 1H), 5.29-5.27 (m, 1H), 5.16 (m, 1H), 4.25-4.16 (m, 3H), 3.58-3.52 (m, 1H), 2.42-0.69 (m, 35H).
Reaction Mechanism 8
Synthetic Example 2-17
Preparation of SAC-1117
After 500 mg of hydroxyphthalimide (Aldrich) was dissolved in 6 ml of dimethylformamide under argon flow, 0.4 ml of 2-chlorobenzyl bromide (Aldrich) was added, and 0.5 ml
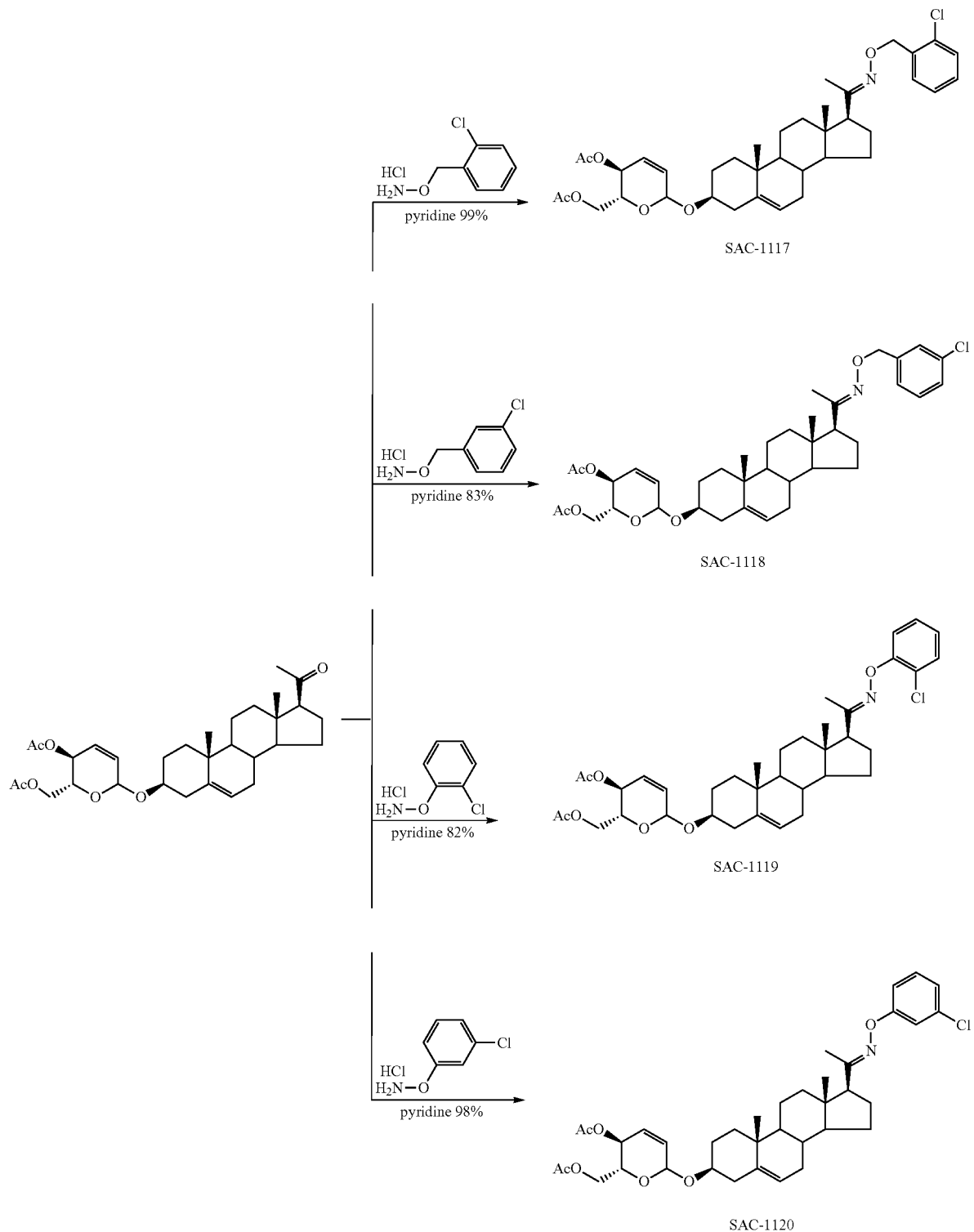

of 1,8-diazabicyclo[5.4.0]undec-7-ene (Aldrich) was slowly added. The mixture was stirred at room temperature for 1 hour, and the reaction was stopped by adding a 2 N hydrochloric acid solution, followed by filtration with ethyl acetate. The solid was again dissolved in ethanol and then recrystallized, followed by filtration and drying, to obtain 833 mg of a white solid (yield: 94%). 400 mg of the obtained white solid was dissolved in 10 ml of dichloromethane, and 0.065 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 227 mg of a solid (yield: 84%). 22 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1117 (62 mg, yield: 98%). $^1$H-NMR (400 MHz, CDCl3) $\delta$7.38-7.31 (m, 2H), 7.22-7.16 (m, 2H), 5.86-5.78 (m, 2H), 5.34 (m, 1H), 5.28-5.26 (m, 1H), 5.17 (s, 2H), 5.15 (m, 1H), 4.24-4.15 (m, 3H), 3.56-3.51 (m, 1H), 2.40-0.56 (m, 35H).

Synthetic Example 2-18

Preparation of SAC-1118

After 500 mg of hydroxyphthalimide (Aldrich) was dissolved in 6 ml of dimethylformamide under argon flow, 0.44 ml of 3-chlorobenzyl bromide (Aldrich) was added, and 0.5 ml of 1,8-diazabicyclo[5.4.0]undec-7-ene (Aldrich) was slowly added. The mixture was stirred at room temperature for 1 hour, and the reaction was stopped by adding a 2 N hydrochloric acid solution, followed by filtration with ethyl acetate. The solid was again dissolved in ethanol and then recrystallized, followed by filtration and drying, to obtain 655 mg of a white solid (yield: 74%). 400 mg of the obtained white solid was dissolved in 10 ml of dichloromethane, and 0.065 ml of hydrazine hydrate (Aldrich) was slowly added at 0° C. The reaction liquid was stirred at room temperature for 2 hours, and the temperature was again lowered to 0° C. The generated solid was filtered out, and the residual filtrate was concentrated under reduced pressure, followed by addition of an aqueous sodium carbonate solution and then extraction with 20 ml of diethyl ether. 3 ml of a 4 M-hydrochloric acid dioxane solution (Aldrich) was added to the solution, followed by filtration and drying, to obtain 166 mg of a solid (yield: 62%). 22 mg of the obtained solid and 50 mg of SAC-0906 obtained as obtained above were dissolved in 2 ml of pyridine (Aldrich) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1118 (52 mg, yield: 83%). $^1$H-NMR (400 MHz, CDCl3) $\delta$7.34 (s, 1H), 7.27-7.22 (m, 3H), 5.89-5.81 (m, 2H), 5.37-5.36 (m, 1H), 5.31-5.29 (m, 1H), 5.18 (m, 1H), 5.05 (s, 2H), 4.26-4.13 (m, 3H), 3.59-3.54 (m, 1H), 2.44-0.59 (m, 35H).

Synthetic Example 2-19

Preparation of SAC-1119

After 163 mg of hydroxyphthalimide (Aldrich), 99 mg of copper chloride (Aldrich), 230 mg of molecular sieve 4 (Aldrich), and 313 mg of 2-chlorophenyl boronic acid (Aldrich) were sequentially dissolved in 5 ml of dichloroethane (Aldrich) under argon flow, 0.09 ml of pyridine (Aldrich) was added, followed by stirring for 5 hours. The reaction liquid was exposed to air, followed by stirring for 14 hours, and then the molecular sieve was filtered out, followed by dilution with ethyl acetate. The solution was concentrated under reduced pressure, and the residue was subjected to silica gel column chromatography using a mixed eluent of ethyl acetate/hexane (1:2) to obtain a compound (38 mg, yield: 14%). After 30 mg of the obtained compound was dissolved in 5 ml of a methanol/chloroform (1:9) solution, 0.065 ml of hydrazine hydrate (Aldrich) was slowly added. The reaction liquid was stirred at room temperature for 2 hours, and the temperature was again lowered to 0° C. The generated solid was filtered out, and the residual filtrate was concentrated under reduced pressure. Then, the residue was subjected to silica gel column chromatography using a mixed eluent of ethyl acetate/hexane (1:2) to obtain 12 mg of a compound (yield: 14%). The compound and 35 mg of SAC-0906 obtained as above were dissolved in 3 ml of ethanol/water/dichloromethane (1:1:1), followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1119 (44 mg, yield: 82%). $^1$H-NMR (400 MHz, CDCl3) $\delta$7.48-7.45 (m, 1H), 7.31-7.29 (m, 1H), 7.20-7.16 (m, 1H), 6.89-6.85 (m, 1H), 5.87-5.78 (m, 2H), 5.36-5.35 (m, 1H), 5.29-5.26 (m, 1H), 5.15 (m, 1H), 4.24-4.14 (m, 3H), 3.58-3.51 (m, 1H), 2.43-0.70 (m, 35H).

Synthetic Example 2-20

Preparation of SAC-1120

After 163 mg of hydroxyphthalimide (Aldrich), 99 mg of copper chloride (Aldrich), 230 mg of molecular sieve 4 (Aldrich), and 313 mg of 3-chlorophenyl boronic acid (Aldrich) were sequentially dissolved in 5 ml of dichloroethane (Aldrich) under argon flow, 0.09 ml of pyridine (Aldrich) was added, followed by stirring for 5 hours. The reaction liquid was exposed to air, followed by stirring for 14 hours, and then the molecular sieve was filtered out, followed by dilution with ethyl acetate. The solution was concentrated under reduced pressure, and the residue was subjected to silica gel column chromatography using a mixed eluent of ethyl acetate/hexane (1:2) to obtain a compound (194 mg, yield: 71%). After 48 mg of the obtained compound was dissolved in 7 ml of a methanol/chloroform (1:9) solution, 0.016 ml of hydrazine hydrate (Aldrich) was slowly added. The reaction liquid was stirred at room temperature for 2 hours, and the temperature was again lowered to 0° C. The generated solid was filtered out, and the residual filtrate was concentrated under reduced pressure. Then, the residue was subjected to silica gel column chromatography using a mixed eluent of ethyl acetate/hexane (1:2) to obtain 18 mg of a compound (yield: 70%). The compound and 35 mg of SAC-0906 obtained as above were dissolved in 2 ml of ethanol/water (1:1) under argon flow, followed by stirring at room temperature for 14 hours. The reaction liquid was acidified by adding a 2 N hydrochloric acid solution, followed by extraction with 20 ml of diethyl ether, drying over magnesium sulfate, and filtration. The filtrate was concentrated under reduced pressure, and the residue was subjected to silica gel column chromatography using a mixed eluent of ethyl acetate/hexane (1:5) to obtain the target compound SAC-1120 (43 mg, yield: 98%). $^1$H-NMR (300 MHz, CDCl3) δ7.30-7.20 (m, 2H), 7.07-6.96 (m, 2H), 5.94-5.84 (m, 2H), 5.42-5.40 (m, 1H), 5.35-5.32 (m, 1H), 5.22 (m, 1H), 4.31-4.19 (m, 3H), 3.64-3.57 (m, 1H), 2.49-0.74 (m, 35H).

Test Examples

Culturing Example

Culturing of Vascular Endothelial Cells

Human retinal endothelial cells (HRECs) purchased from Cell Systems (USA) were seeded on a 100 mm culture dish containing EGM medium (Life Technologies, USA) containing 20% (w/v) fetal bovine serum (FBS, HyClone, Canada), 100 units/mL penicillin (Invitrogen, USA), 100 μg/mL streptomycin (Invitrogen, USA), 3 ng/mL fibroblast growth factor (Upstate Biotechnology, USA) and 5 units/mL heparin and cultured in a 5% $CO_2$ incubator at 37° C.

Test Example 1

Figure 1B:
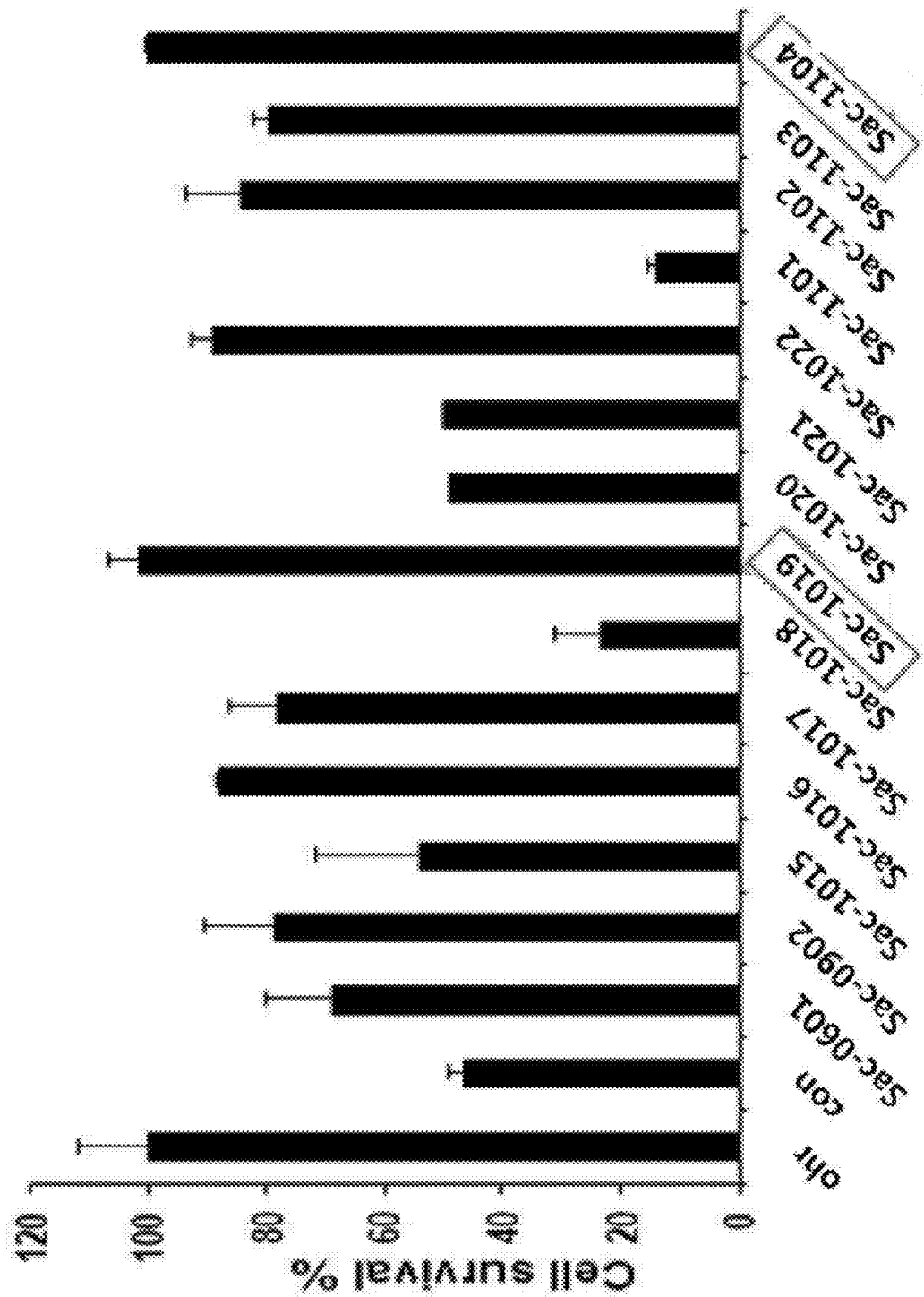
Figure 1C:
Figure 2A:
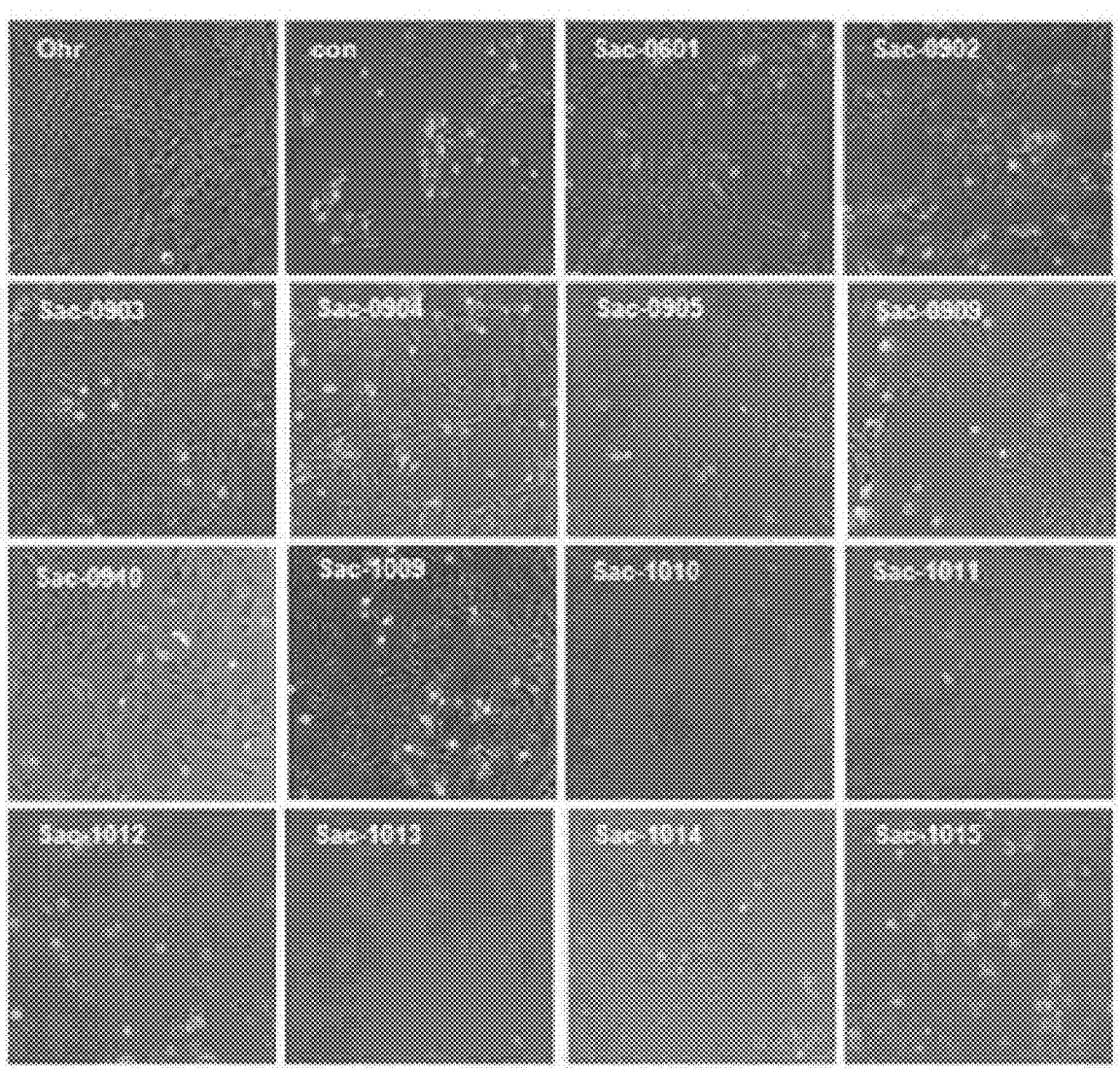
Figure 2B:
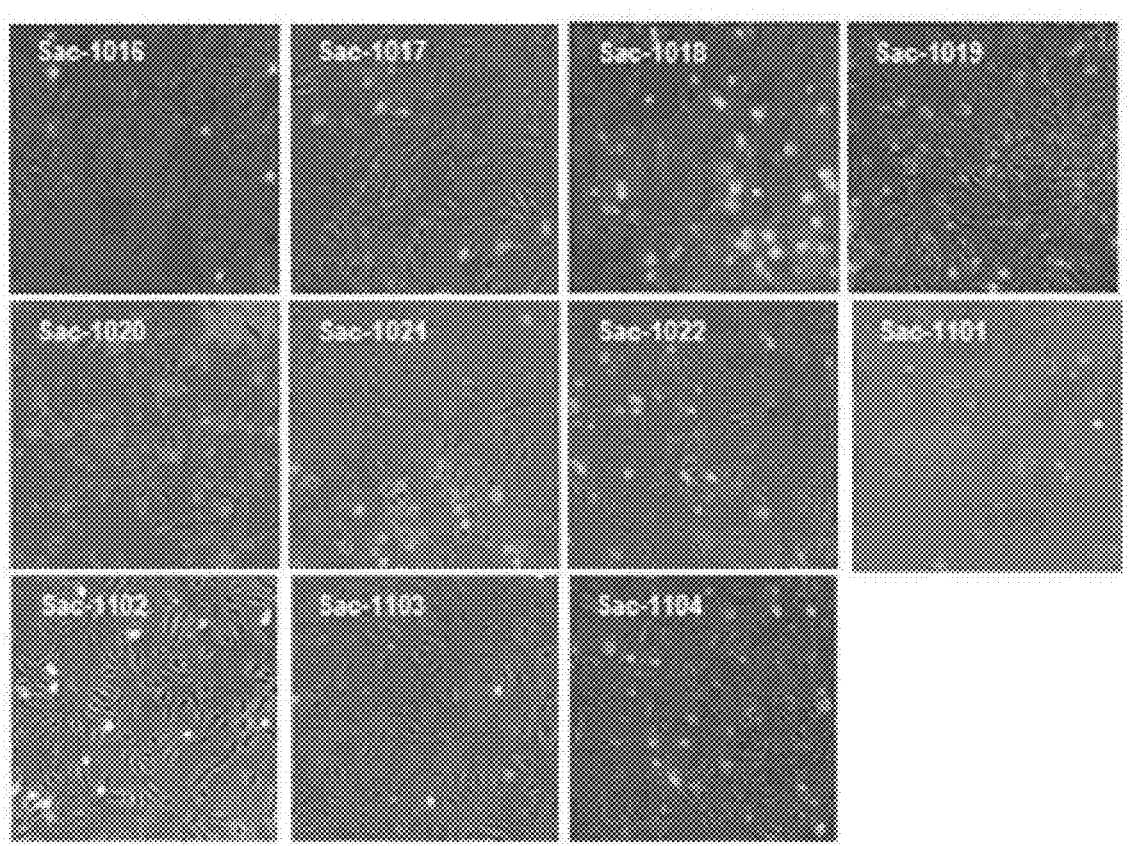
Figure 2C:
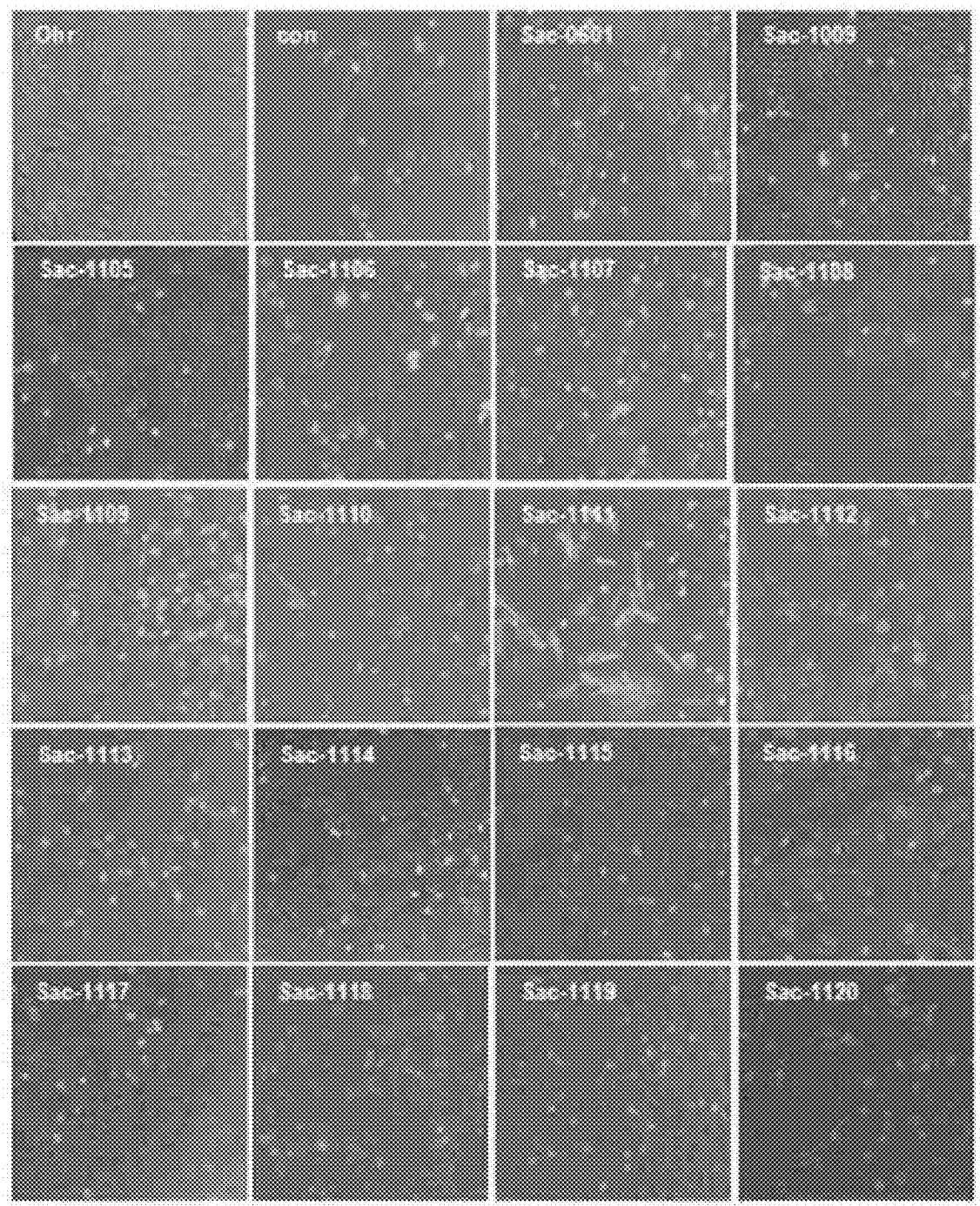

Screening of Synthesized Derivatives Based on Ability to Inhibit Vascular Endothelial Cell Apoptosis Based on the previous researches conducted by the present inventors, synthesized derivatives of Rk1 having a steroid backbone and having an ability to inhibit vascular endothelial cell apoptosis were screened. Vascular endothelial cells HRECs (3×10$^5$ cells/well) were plated on a 24-well plate in which 1 ml of EGM medium containing 20% fetal bovine serum was present. The next day, the cells were transferred to serum-free EGM media containing 10 μg/ml of the compounds synthesized in Synthetic Examples 1 and 2. After 24 hours, cell viability was determined by MTT assay (Mosmann T, *Journal of Immunological Methods* 65(1-2):5563 (1983); Cory A H, et al., Cancer Communications 3(7):20712 (1991)). As a result of test, it was confirmed that the synthesized derivatives Sac-1009, Sac-1016, Sac-1017, Sac-1019, Sac-1022, Sac-1102, Sac-1103, Sac-1104, Sac-1106 to Sac-1115, Sac-1117, Sac-1118, and Sac-1119 had an ability to inhibit apoptosis (FIGS. 1a, 1b, and 1c). Sac-0601, Sac-0902, Sac-0903, Sac-0904, Sac-0905, Sac-0909, Sac-0910, Sac-1004 in FIGS. 1 and 2 are synthesized derivatives having an ability to inhibit apoptosis, which were obtained in the previous researches by the present inventors, and were used as control groups for measuring effects of the synthesized derivatives of the present invention (Korean Patent Application Publication No. 2011-0047170). Among the control groups, Sac-0601 showed an ability to inhibit apoptosis equivalent to that of Rk1, and Sac-1004 is a synthesized derivative showing the most excellent ability to inhibit apoptosis in the previous researches. As a result of comparison of the ability to inhibit apoptosis between the synthetic derivatives of the present invention and the control groups, it was confirmed that the inhibitory abilities of Sac-1009, Sac-1104, and Sac-1019 were the most excellent, and it was confirmed that Sac-1009, Sac-1104, and Sac-1019 had an ability to inhibit apoptosis equivalent to that of Sac-1004 obtained in the previous researches. Meanwhile, the observation results of cell morphology change also showed that the synthesized derivatives had an ability to protect vascular endothelial cells (FIGS. 2a, 2b, and 2c).

Test Example 2

Measurement on Ability to Inhibit Apoptosis of Sac-1009, Sac-1104, and Sac-1019

Figure 3:
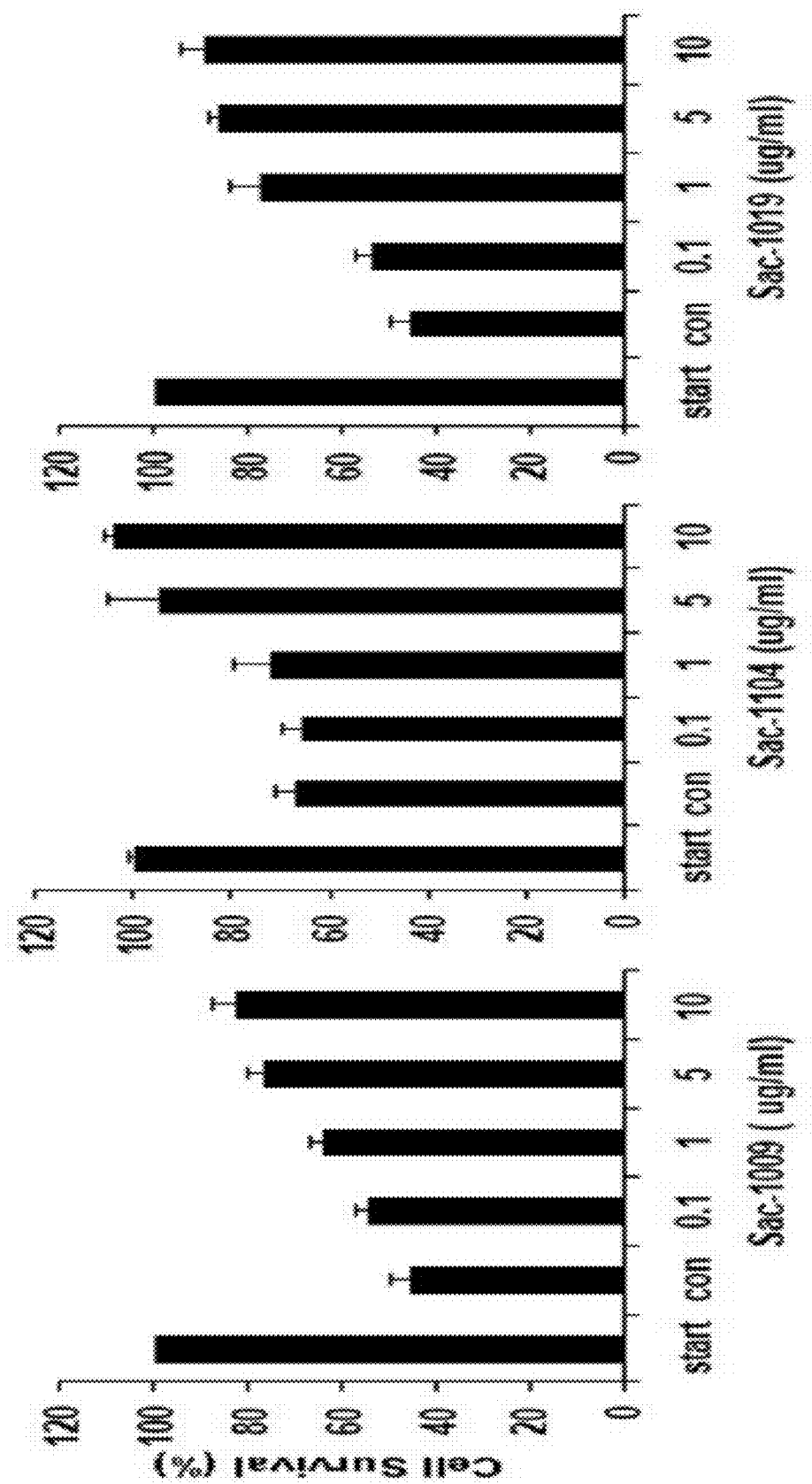
FIG. 3 shows inhibition effects of Sac-1009, Sac-1104 and Sac-1019 on apoptosis. HRECs (3×105 cells/well) were seeded on a 24-well plate in EGM medium containing 20% fetal bovine serum. The next day, the cells were transferred to a serum depletion EGM medium containing Sac-1009, Sac-1104 or Sac-1019. Sac-1009, Sac-1104 and Sac-1019 were added into the medium at a concentration of 0, 0.1, 1, 5 or 10 μg/mL, respectively. Cell viability was determined by MTT assay 48 hours later. Each synthesized compound shows the most effective ability to inhibit apoptosis at a concentration of 10 μg/mL.

Among the synthesized derivatives of test example 1, Sac-1009, Sac-1104, and Sac-1019, which had the most excellent ability to inhibit apoptosis, were selected, and then applied to cells according to concentrations to measure the ability to inhibit apoptosis. After apoptosis was induced by removing serum from the medium of vascular endothelial cells, Sac-1009, Sac-1104, and Sac-1019 were applied to cells to measure the ability to inhibit apoptosis. Vascular endothelial cells HRECs (3×10$^5$ cells/well) were plated on a 24-well plate in which 1 ml of EGM medium containing 20% fetal bovine serum was present. The next day, the cells were transferred to serum-free EGM media containing Sac-1009, Sac-1104, and Sac-1019. Sac-1009, Sac-1104, and Sac-1019 were added at concentrations of 0, 0.1, 1, 5, and 10 μg/ml. After 48 hours, cell viability was determined by MTT assay. As a result, the respective synthesized materials inhibited apoptosis of HRECs in a concentration-dependent manner, and in particular, Sac-1009, Sac-1104, and Sac-1019 showed the most effective ability to inhibit apoptosis at 10 μg/ml (FIG. 3).

Test Example 3

Screening of Synthesized Derivatives Based on Change in Cytoskeleton

Figure 4:
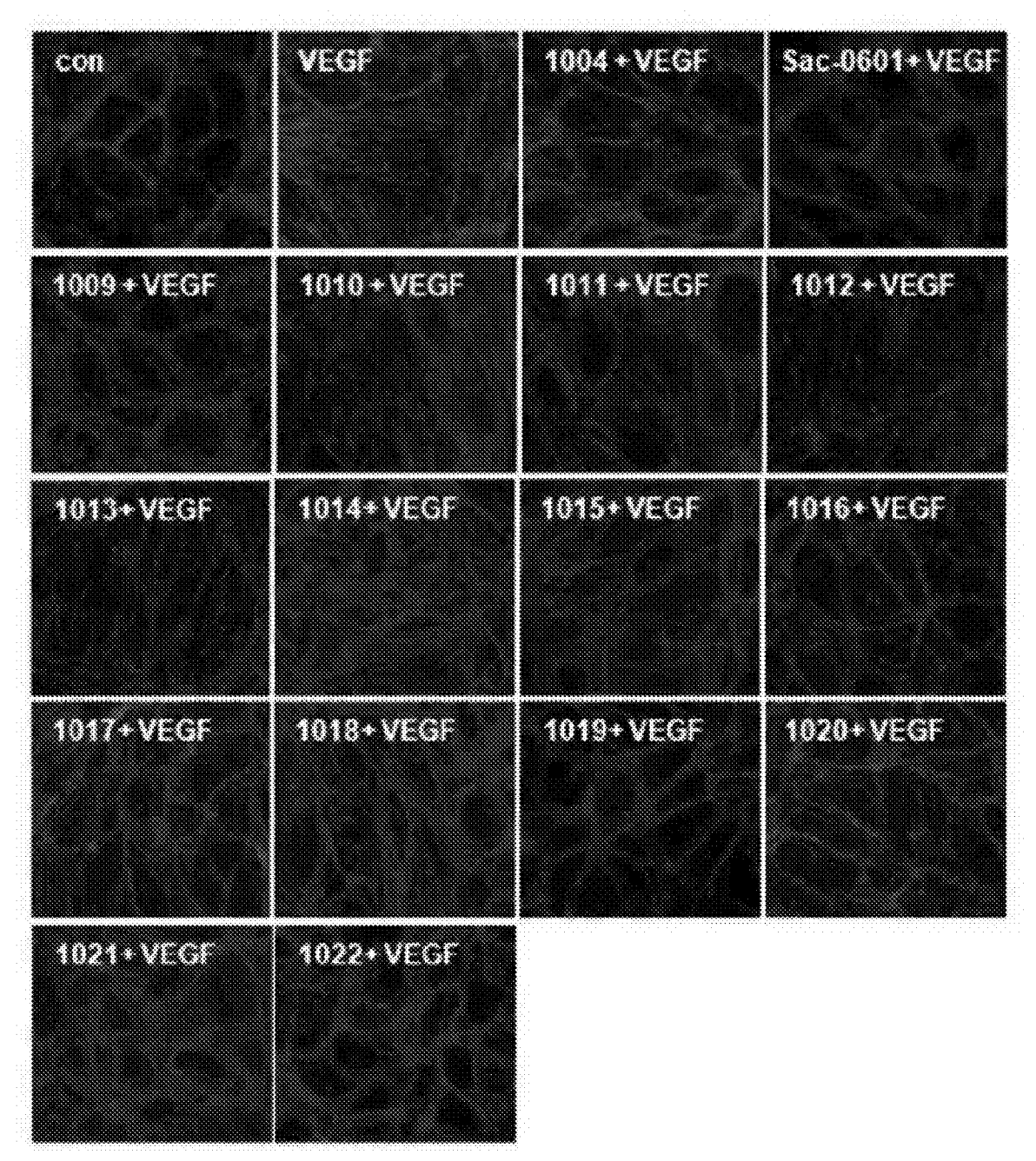
Figure 5:
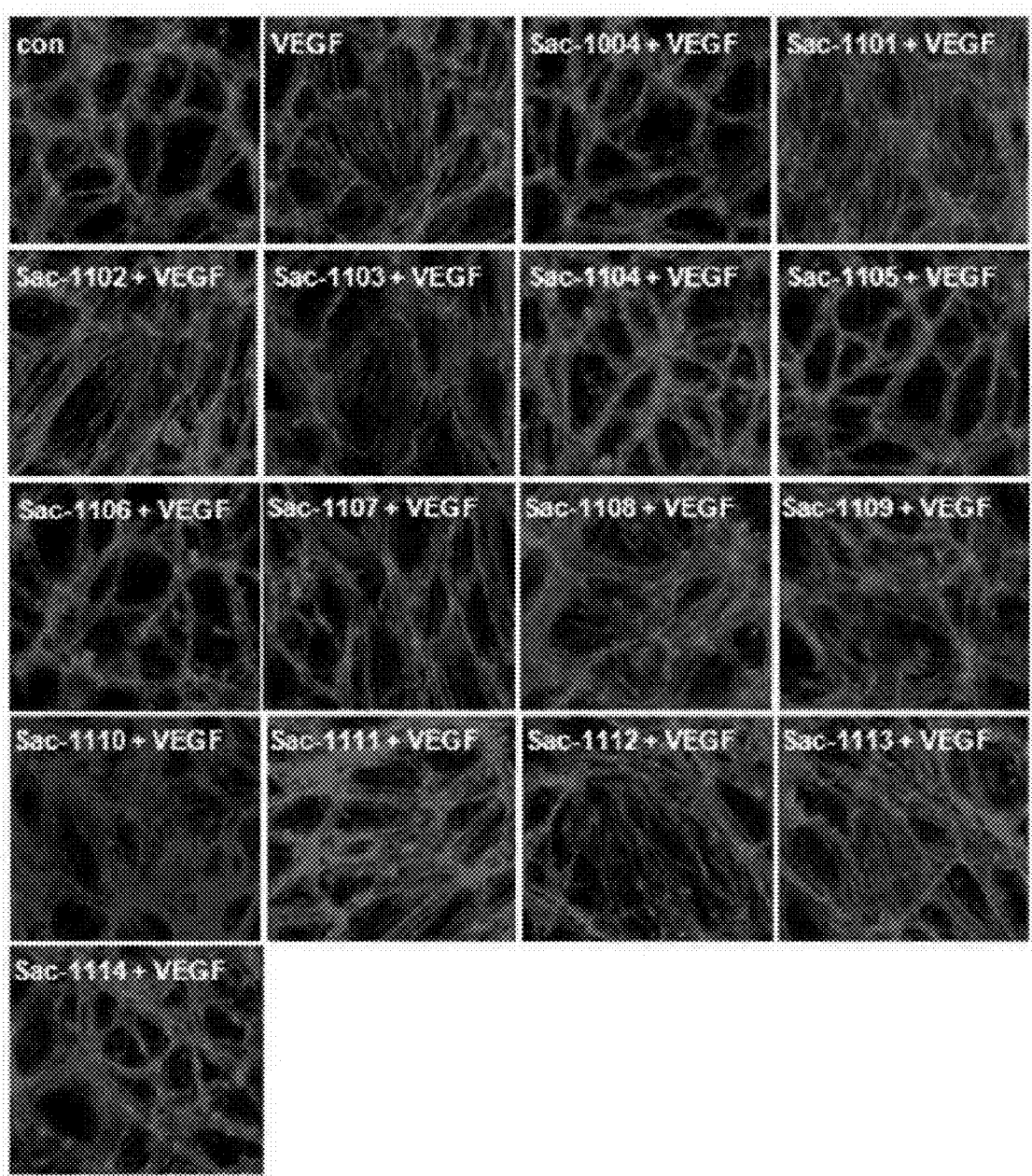

As results of test examples 1 and 2, Sac-1009, Sac-1104, and Sac-1019 were confirmed to increase cell viability of HRECs in a serum depletion environment. In addition, it was confirmed whether the synthesized derivatives had an ability to inhibit actin stress fibers by VEGF. It is known that the change in the actin structure of the cytoskeleton is closely related with the permeability of vascular endothelial cells. Increased permeability of vascular endothelial cells leads to an increase in actin stress fibers and a decrease in cortical actin ring structures. Based on this, the ability to inhibit vascular endothelial permeability of the synthesized derivatives of Rk1 was screened. Confluent HRECs were pretreated with 10/ml the synthesized compounds for 1 hour before the treatment with 20 ng/ml VEGF (Upstate Biotechnology). Then, the cells were fixed with 4% paraformaldehyde for 20 minutes at room temperature, and washed 3 times with PBS (pH 7.4). Then, the cells were permeabilized with 0.1% Triton X-100/PBS, and reacted with 0.1 mg/ml rhodamine phalloidin (Molecular Probes) for 1 hour. Then, the cells were observed under a fluorescence microscope (Olympus). As a result, it was confirmed that the synthesized derivatives Sac-1009, Sac-1011 to Sac-1013, Sac-1015, Sac-1016, Sac-1019, Sac-1020, Sac-1022, Sac-1103 to Sac-1107, and Sac-1114 had an ability to inhibit the formation of actin stress fibers (FIGS. 4 and 5). Further, it was confirmed that, similarly to the results of screening the ability to inhibit vascular cell apoptosis, Sac-1009, Sac-1104, and Sac-1019 were the most excellent in abilities to inhibit the formation of actin stress fibers induced by VEGF and maintain the cortical actin ring structure.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A compound represented by Chemical Formula 1 or a pharmaceutically acceptable salt thereof:

Chemical Formula 1

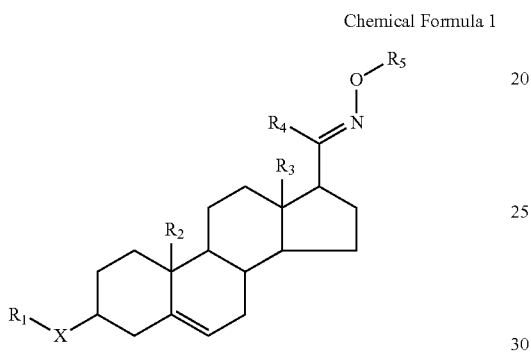

wherein X is oxygen or sulfur;

$R_1$ is halo; $C_{3-10}$ cycloalkyl; $C_{3-10}$ cycloalkenyl; $C_{3-15}$ heterocycloalkylalkyl containing oxygen; sulfur or nitrogen as a heteroatom; $C_{3-10}$ heterocycloalkenyl containing oxygen, sulfur or nitrogen as a heteroatom optionally substituted with one or more substituents independently selected from the group consisting of $C_{2-8}$ alkylcarboxyl, $C_{3-8}$alkylcarboxylalkyl, —O—$R_6$, and —CH$_2$—O—$R_7$; $C_{6-10}$ aryl; $C_{6-15}$ aralkyl; $C_{6-15}$ alkaryl; or $C_{3-15}$ heteroaryl containing oxygen, sulfur or nitrogen as a heteroatom;

$R_2$ and $R_3$ are independently hydrogen or $C_{1-10}$ alkyl;

$R_4$ is hydrogen, hydroxy or $C_{1-10}$ alkyl;

$R_5$ is hydrogen; hydroxyl; $C_{1-30}$ alkyl; $C_{3-10}$ cycloalkyl optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-30}$ alkenyl; $C_{3-10}$ cycloalkenyl optionally substituted with one or more substituents independently selected from the group consisting of hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-30}$ alkynyl; $C_{2-10}$ heterocycloalkyl containing oxygen, sulfur or nitrogen as a heteroatom optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{3-15}$ heterocycloalkylalkyl containing oxygen, sulfur or nitrogen as a heteroatom; $C_{2-30}$ alkoxyalkyl; $C_{3-30}$ alkoxyalkoxyalkyl; $C_{3-10}$ heterocycloalkenyl containing oxygen, sulfur or nitrogen as a heteroatom optionally substituted with one or more substituents independently selected from the group consisting of hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{1-20}$ alcohol, $C_{1-20}$ alkenol; $C_{2-30}$ acyl; $C_{1-10}$ amide; $C_{1-10}$ amine; $C_{2-15}$ ester; sulfate; carboxyl; $C_{3-20}$ carboxyalkyl; $C_{3-20}$ carboxyalkenyl; $C_{3-20}$ alkylcarboxyl; $C_{3-20}$ alkenylcarboxyl; $C_{3-20}$ alkylcarboxyalkyl; $C_{3-20}$ alkylcarboxyalkenyl; $C_{3-20}$ alkenylcarboxyalkenyl; $C_{4-20}$ alkenylcarboxyalkenyl; $C_{6-30}$ aryl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{6-30}$ aralkyl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{6-30}$ alkaryl;

$C_{3-30}$ heteroaryl containing oxygen, sulfur or nitrogen as a heteroatom optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; or $C_{6-30}$ arylcarbonyl; and $R_6$ and $R_7$ are independently hydrogen or $C_{1-10}$ alkyl.

2. The compound of claim 1 or a pharmaceutically acceptable salt thereof, which is represented by Chemical Formula 2:

Chemical Formula 2

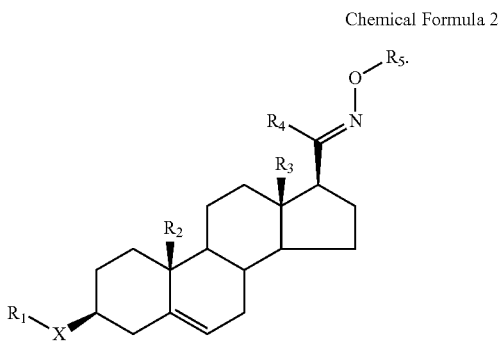

3. The compound of claim 1 or a pharmaceutically acceptable salt thereof, wherein X is oxygen.

4. The compound of claim 1 or a pharmaceutically acceptable salt thereof, wherein $R_1$ is halo; $C_{3-8}$ cycloalkyl; $C_{3-8}$ cycloalkenyl; $C_{3-10}$ heterocycloalkylalkyl containing oxygen, sulfur or nitrogen as a heteroatom; $C_{3-8}$ heterocycloalkenyl containing oxygen, sulfur or nitrogen as a heteroatom optionally substituted with one or more substituents independently selected from the group consisting of $C_{2-8}$ alkylcarboxyl, $C_{3-8}$ alkylcarboxylalkyl, —O—$R_6$, and —CH$_2$—O—$R_7$; $C_{6-10}$ aryl; $C_{6-15}$ aralkyl; $C_{6-15}$ alkaryl; or $C_{3-15}$ heteroaryl containing oxygen, sulfur or nitrogen as a heteroatom.

5. The compound of claim 1 or a pharmaceutically acceptable salt thereof, wherein $R_1$ is $C_{5-8}$ heterocycloalkenyl containing oxygen, sulfur or nitrogen as a heteroatom optionally substituted with one or more substituents independently selected from the group consisting of $C_{2-8}$ alkylcarboxyl, $C_{3-8}$ alkylcarboxylalkyl, —O—$R_6$, and —CH$_2$—O—$R_7$.

6. The compound of claim 1 or a pharmaceutically acceptable salt thereof, wherein $R_5$ is hydrogen; $C_{1-10}$ alkyl; $C_{3-8}$ cycloalkyl optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-10}$ alkenyl; $C_{3-8}$ cycloalkenyl optionally substituted with one or more substituents independently selected from the group consisting of hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-10}$ alkynyl; $C_{2-8}$ heterocycloalkyl containing oxygen, sulfur or nitrogen as a heteroatom optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{3-10}$ heterocycloalkylalkyl containing oxygen, sulfur or nitrogen as a heteroatom; $C_{2-20}$ alkoxyalkyl; $C_{3-20}$ alkoxyalkoxyalkyl; $C_{3-8}$ heterocycloalkenyl containing oxygen, sulfur or nitrogen as a heteroatom optionally substituted with one or more substituents independently selected from the group consisting of hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{1-10}$ alcohol; $C_{1-10}$ alkenol; $C_{2-20}$ acyl; $C_{1-5}$ amide; $C_{1-5}$ amine; $C_{2-10}$ ester; sulfate; carboxyl; $C_{3-10}$ carboxyalkyl; $C_{3-10}$ carboxyalkenyl; $C_{3-10}$ alkylcarboxyl; $C_{3-10}$ alkenylcarboxyl; $C_{3-10}$ alkylcarboxyalkyl; $C_{3-10}$ alkylcarboxyalkenyl; $C_{3-10}$ alkenylcarboxyalkyl; $C_{4-10}$ alkenylcarboxyalkenyl; $C_{6-20}$ aryl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{6-20}$ aralkyl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{6-20}$ alkaryl optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{3-20}$ heteroaryl containing oxygen, sulfur or nitrogen as a heteroatom optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; or $C_{6-20}$ arylcarbonyl.

7. The compound of claim 1 or a pharmaceutically acceptable salt thereof, wherein $R_5$ is $C_{1-6}$ alkyl; $C_{6-8}$ cycloalkyl optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-6}$ alkenyl; $C_{6-8}$ cycloalkenyl optionally substituted with one or more substituents independently selected from the group consisting of hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-8}$ alkoxyalkyl, $C_{6-20}$ aryl, and $C_{7-20}$ arylcarboxyl; $C_{2-5}$ alkynyl; $C_{6-15}$ aryl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; $C_{6-15}$ aralkyl optionally substituted with one or more substituents independently selected from the group consisting of hydroxy, halo, halomethyl, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro; or $C_{3-15}$ heteroaryl containing oxygen, sulfur or nitrogen as a heteroatom optionally substituted with one or more substituents independently selected from the group consisting of hydroxy, halo, $C_{1-5}$ alkyl, $C_{1-5}$ alcohol, $C_{1-5}$ alkoxy, $C_{2-8}$ alkoxyalkyl, nitro, cyano, and $C_{2-8}$ alkylcarboxylnitro.

8. The compound of claim 1 or a pharmaceutically acceptable salt thereof, which is selected from the group consisting of Chemical Formulae 3 to 36:

Chemical Formula 3

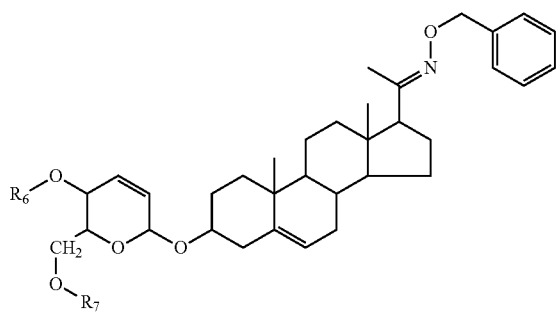

Chemical Formula 4

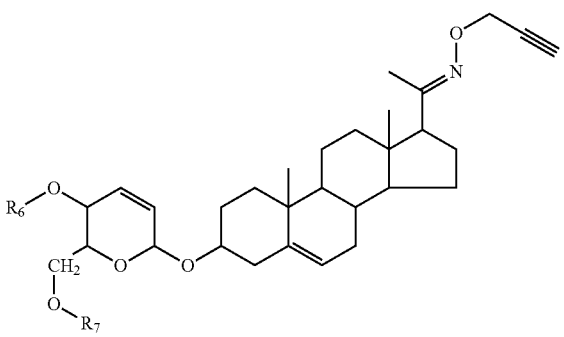

Chemical Formula 5

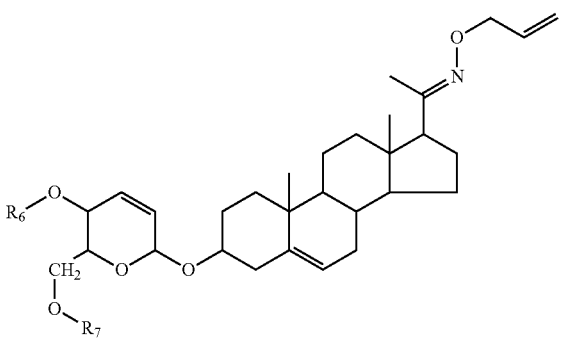

Chemical Formula 6

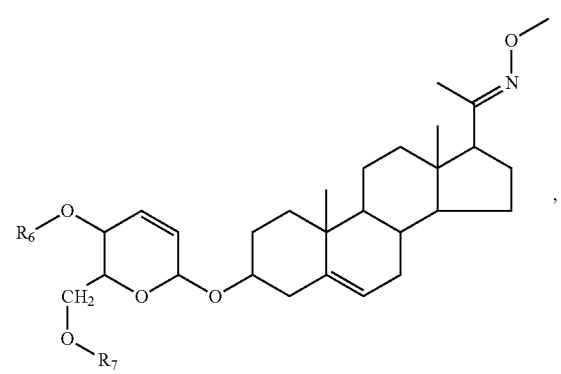

75
-continued
Chemical Formula 7
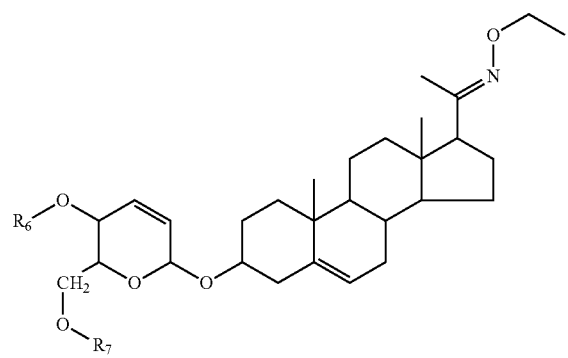
,
Chemical Formula 8
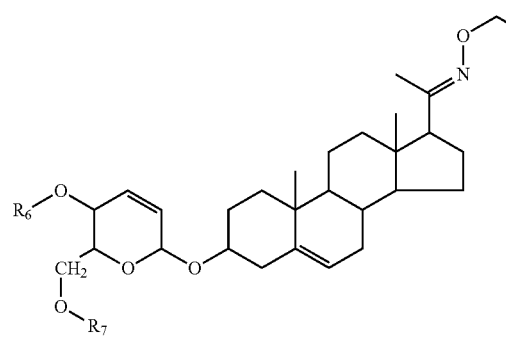
,
Chemical Formula 9
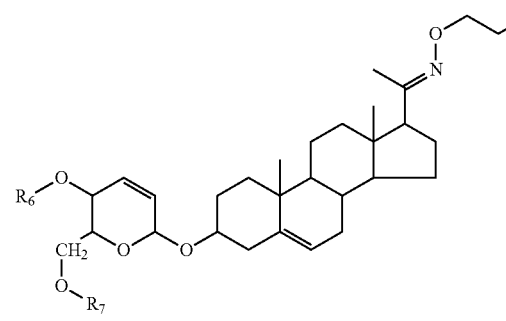
,
Chemical Formula 10
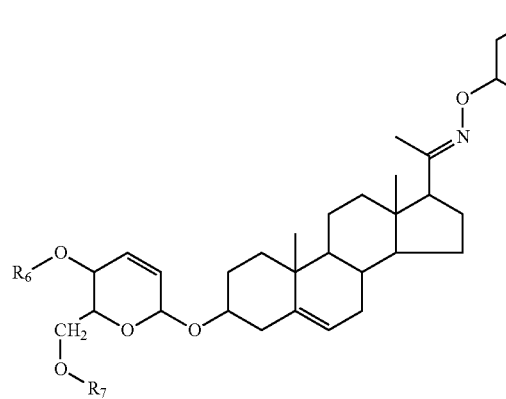
,
76
-continued
Chemical Formula 11
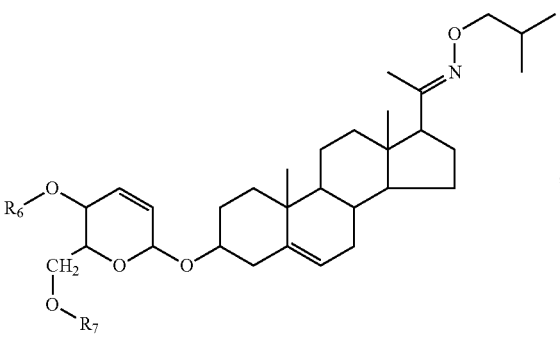
,
Chemical Formula 12
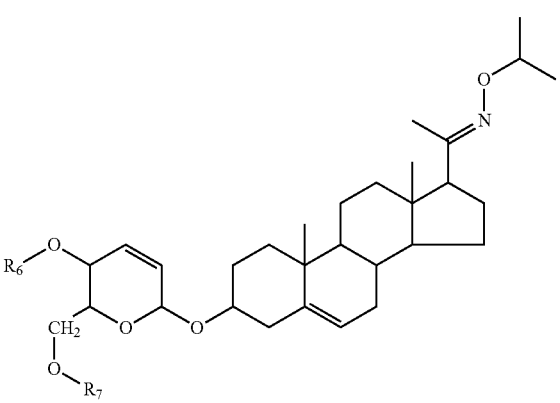
,
Chemical Formula 13
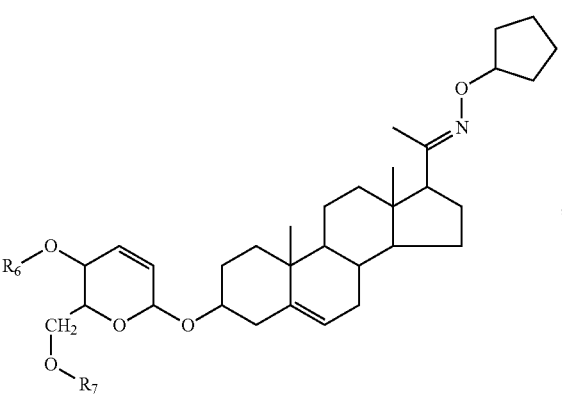
,
Chemical Formula 14
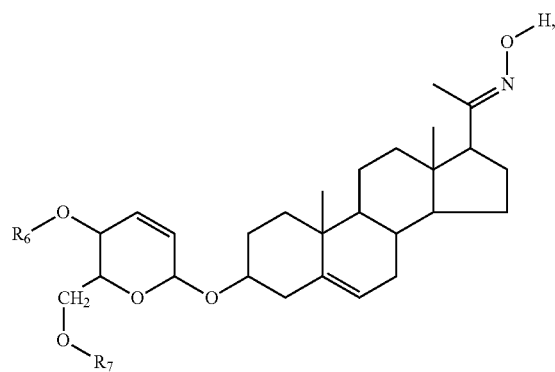
,

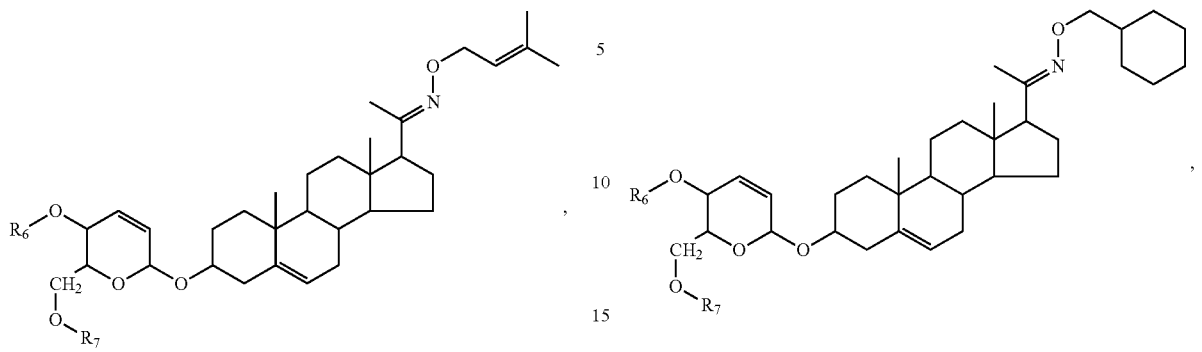

-continued
Chemical Formula 23
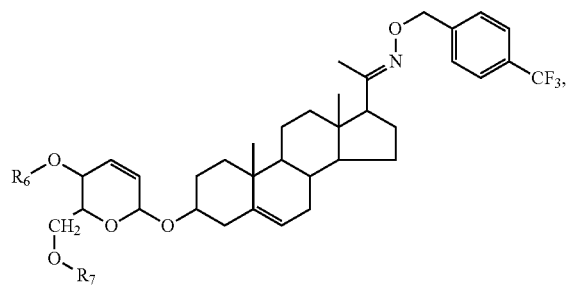
Chemical Formula 24
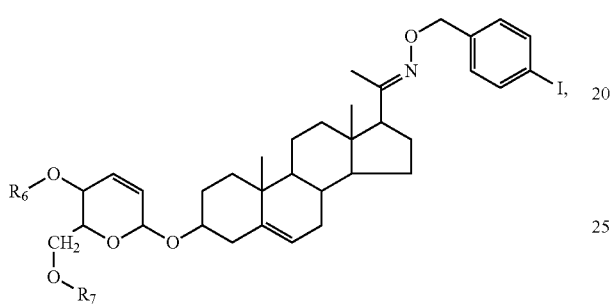
Chemical Formula 25
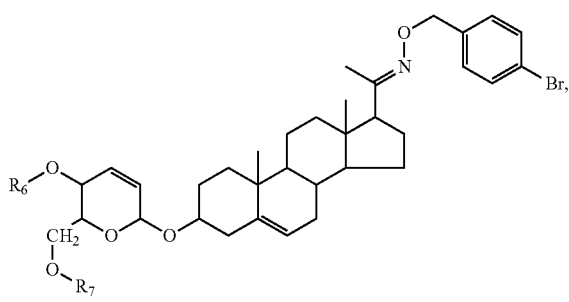
Chemical Formula 26
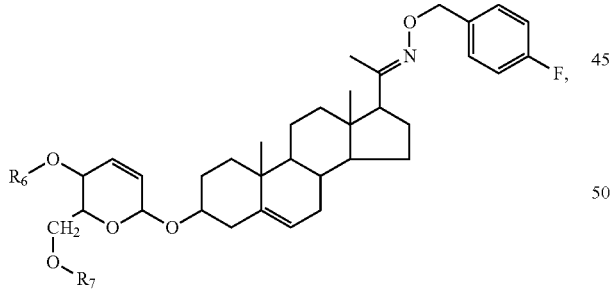
Chemical Formula 27
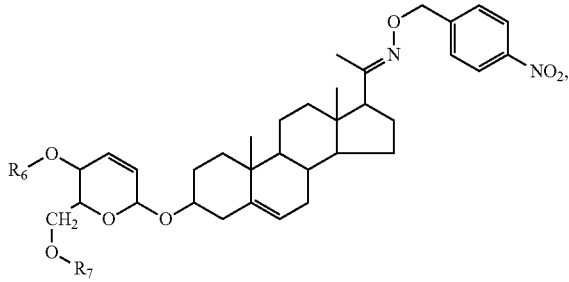
-continued
Chemical Formula 28
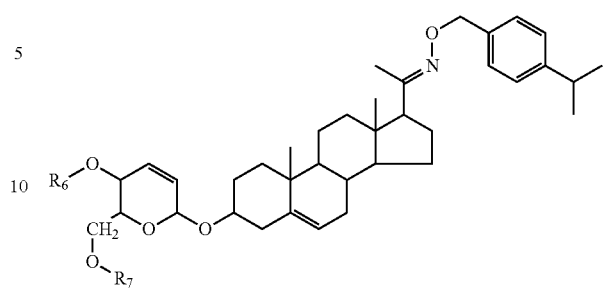
Chemical Formula 29
Chemical Formula 30
Chemical Formula 31
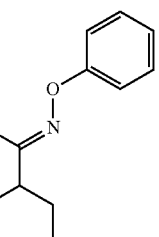

Chemical Formula 32
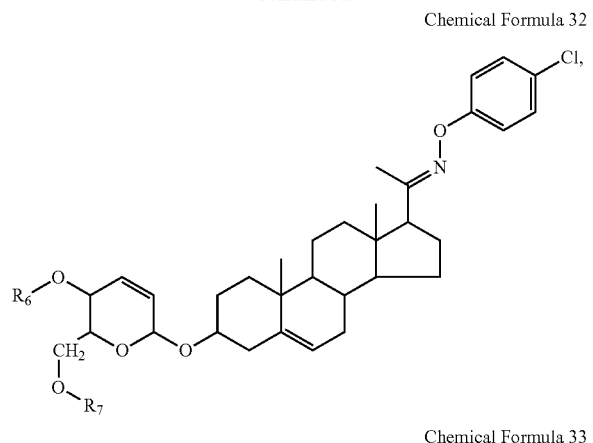
Chemical Formula 33
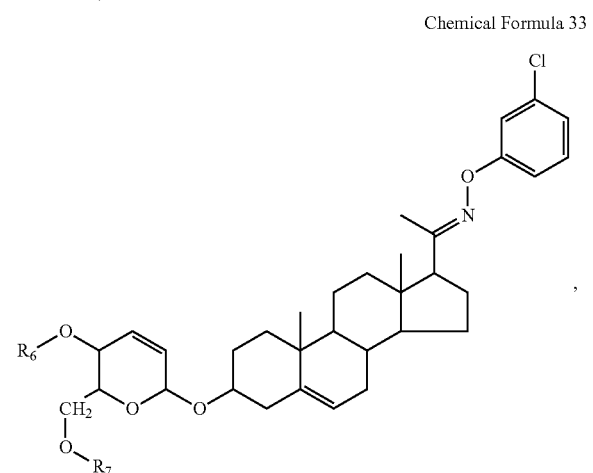
Chemical Formula 34
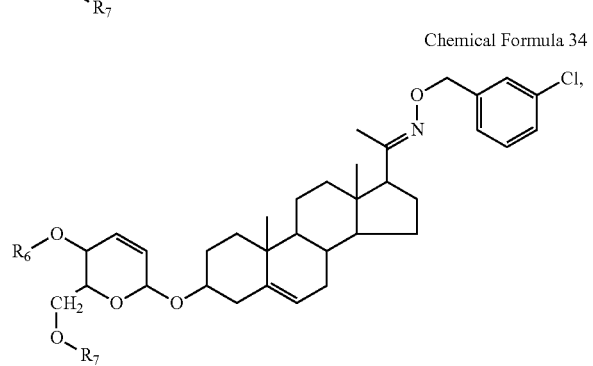
Chemical Formula 35
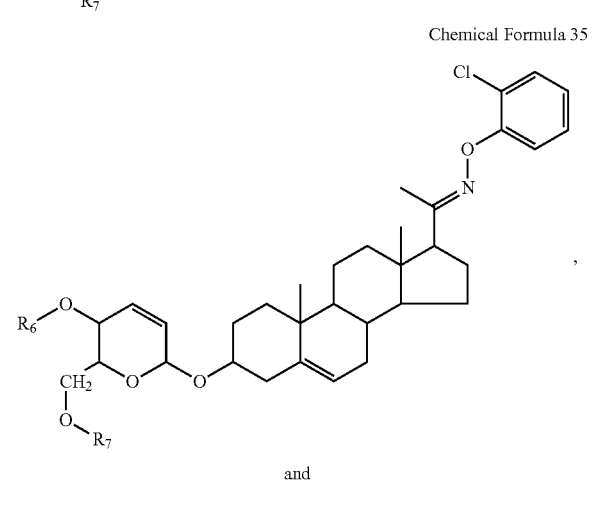
and
Chemical Formula 36
wherein $R_6$ and $R_7$ are independently hydrogen or $C_{1-10}$ alkyl.
9. The compound of claim 1 or a pharmaceutically acceptable salt thereof, which is selected from the group consisting of Chemical Formulae 37 to 70:
Chemical Formula 37
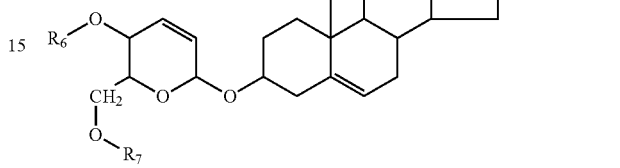
Chemical Formula 38
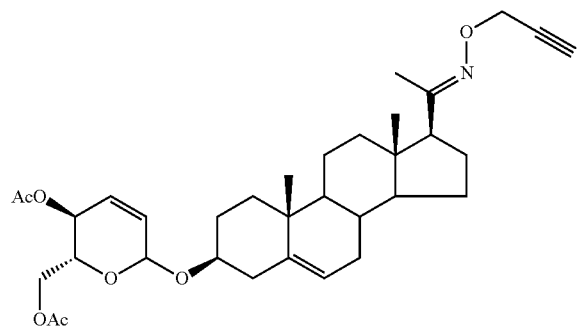

-continued
Chemical Formula 39
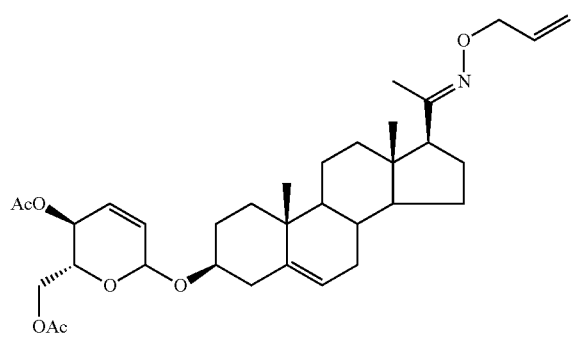
Chemical Formula 40
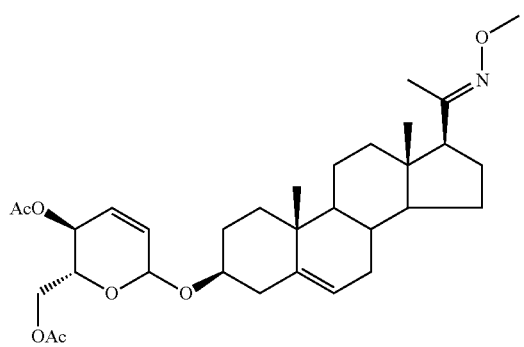
Chemical Formula 41
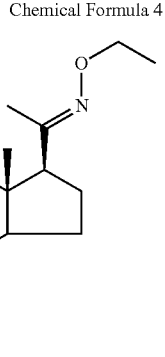
Chemical Formula 42
-continued
Chemical Formula 43
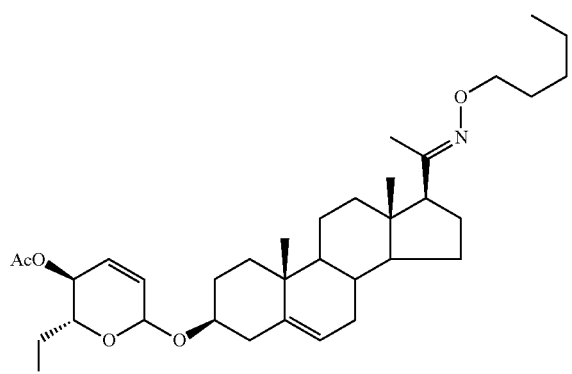
Chemical Formula 44
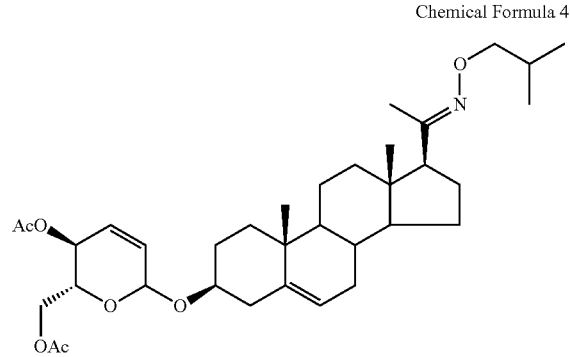
Chemical Formula 45
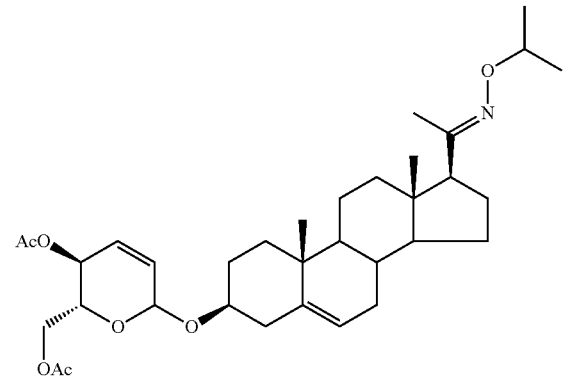
Chemical Formula 46

Chemical Formula 47
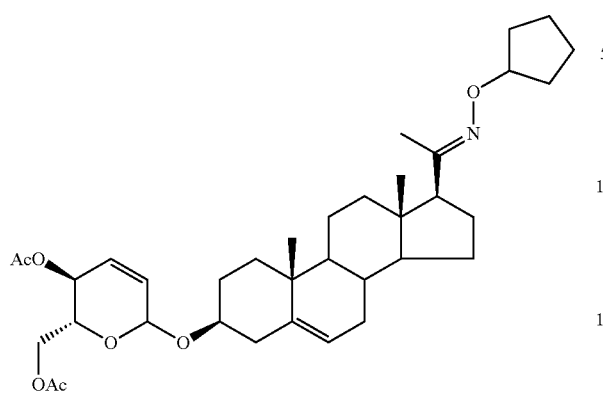
Chemical Formula 48
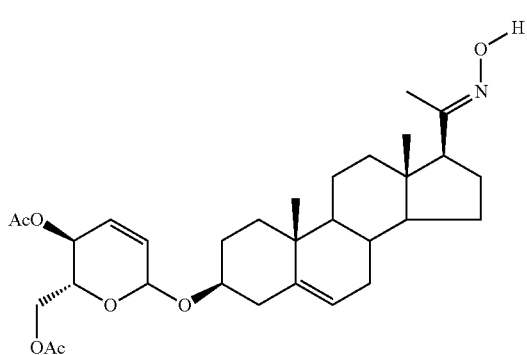
Chemical Formula 49
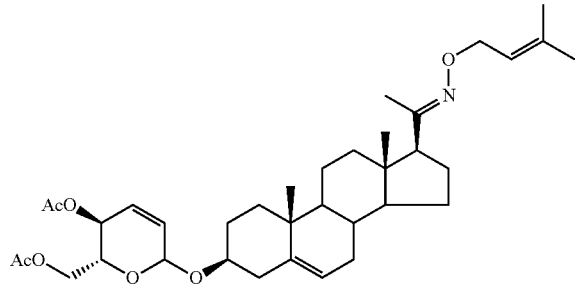
Chemical Formula 50
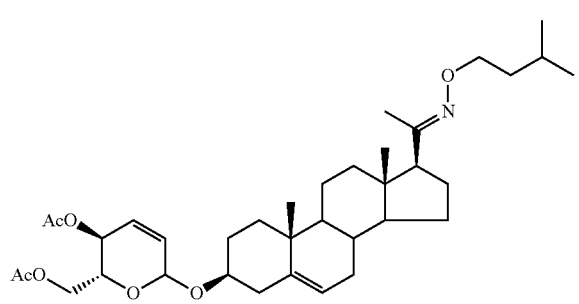
Chemical Formula 51
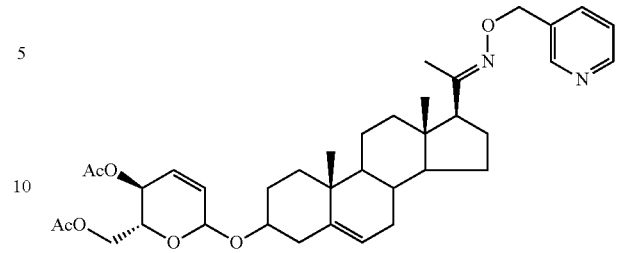
Chemical Formula 52
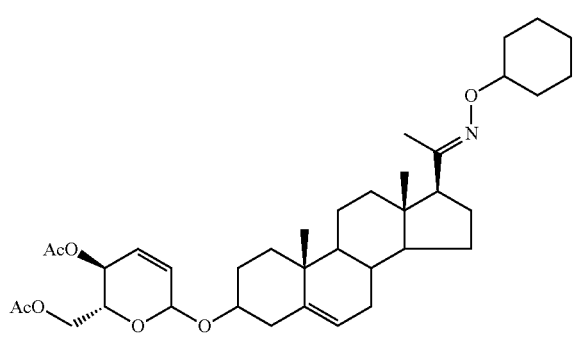
Chemical Formula 53
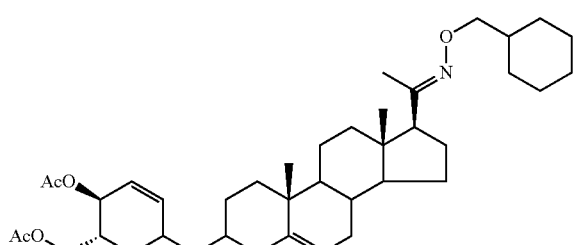
Chemical Formula 54
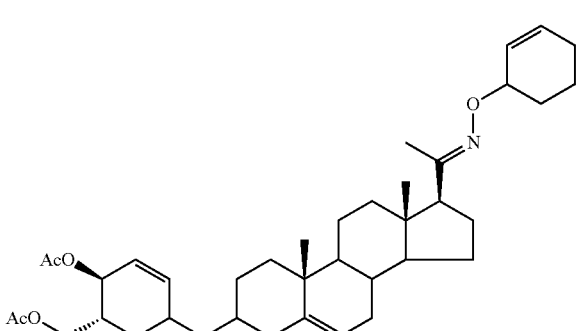
Chemical Formula 55
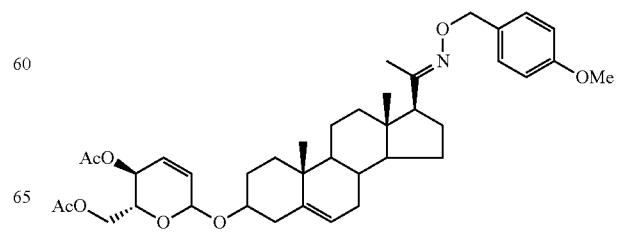

Chemical Formula 56
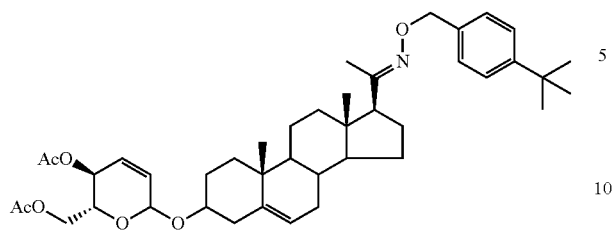
Chemical Formula 57
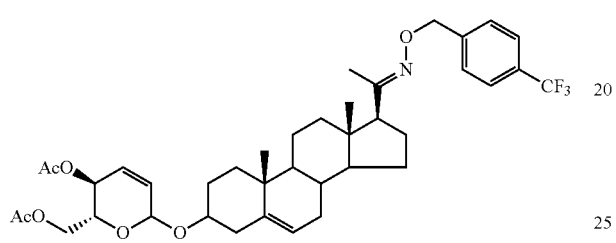
Chemical Formula 58
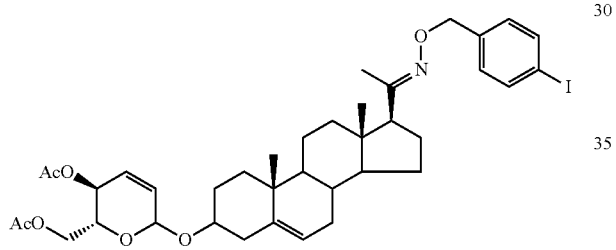
Chemical Formula 59
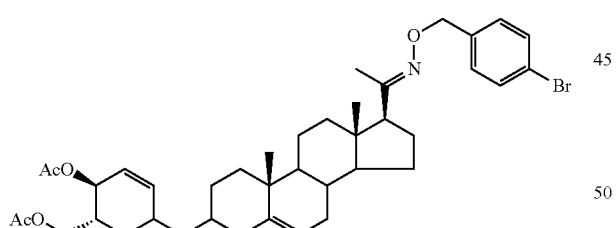
Chemical Formula 60
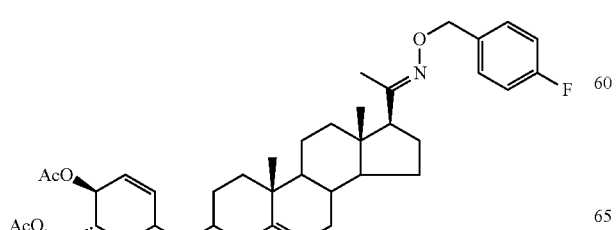
Chemical Formula 61
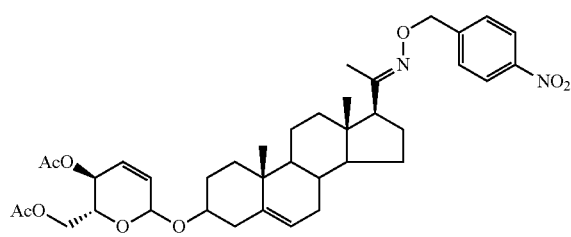
Chemical Formula 62
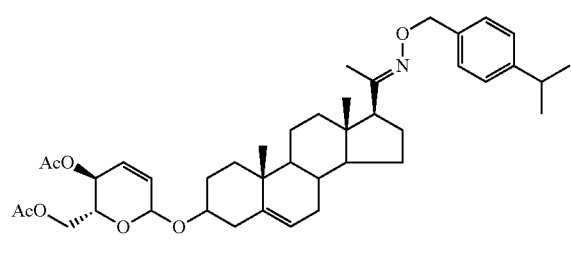
Chemical Formula 63
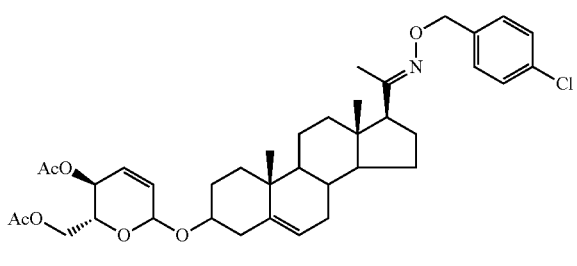
Chemical Formula 64
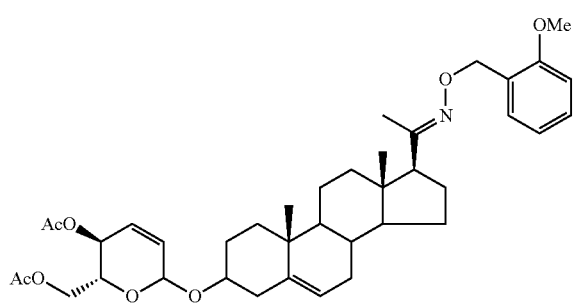
Chemical Formula 65
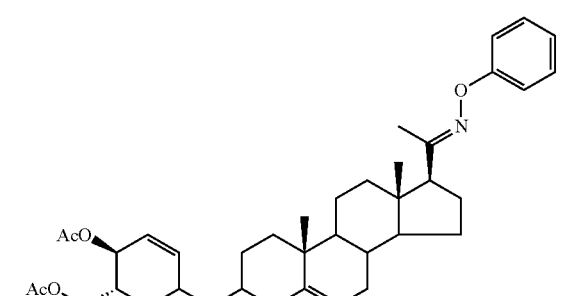

Chemical Formula 66

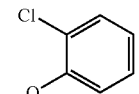

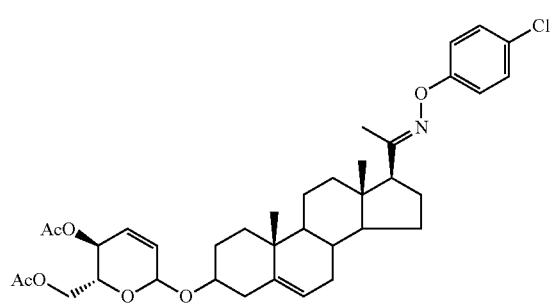

Chemical Formula 67

Chemical Formula 68

Chemical Formula 69

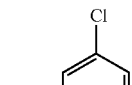

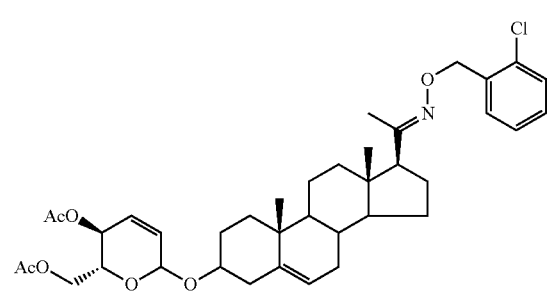

Chemical Formula 70

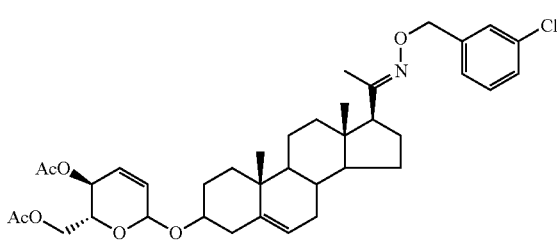

10. A pharmaceutical composition comprising: (a) a pharmaceutically effective amount of the compound of claim 1 or a pharmaceutically acceptable salt thereof; and (b) a pharmaceutically acceptable carrier.

11. A food composition comprising the compound of claim 1 or a salt thereof.

12. A method for inhibiting vascular leakage comprising: administering the pharmaceutical composition of claim 10 to a subject in need thereof.

* * * * *